US007160682B2

(12) United States Patent
Hackett et al.

(10) Patent No.: US 7,160,682 B2
(45) Date of Patent: *Jan. 9, 2007

(54) NUCLEIC ACID TRANSFER VECTOR FOR THE INTRODUCTION OF NUCLEIC ACID INTO THE DNA OF A CELL

(75) Inventors: Perry B. Hackett, Shoreview, MN (US); Karl J. Clark, Ramsey, MN (US); Zoltan Ivics, Berlin (DE); Zsuzsanna Izsvak, Berlin (DE); Scott C. Fahrenkrug, St. Paul, MN (US)

(73) Assignee: Regents of the University of Minnesota, Minneapolis, MN (US)

( * ) Notice: Subject to any disclaimer, the term of this patent is extended or adjusted under 35 U.S.C. 154(b) by 521 days.

This patent is subject to a terminal disclaimer.

(21) Appl. No.: 10/191,698

(22) Filed: Jul. 9, 2002

(65) Prior Publication Data

US 2003/0154500 A1 Aug. 14, 2003

Related U.S. Application Data

(63) Continuation of application No. 09/191,572, filed on Nov. 13, 1998, now abandoned.

(51) Int. Cl.
*C12Q 1/68* (2006.01)
*C12N 5/00* (2006.01)
*C07H 21/02* (2006.01)
*C12H 21/04* (2006.01)

(52) U.S. Cl. .................. 435/6; 536/23.1; 536/23.4; 536/23.5; 536/24.1; 435/325

(58) Field of Classification Search .................. None
See application file for complete search history.

(56) References Cited

U.S. PATENT DOCUMENTS

| 4,631,259 | A | 12/1986 | Clewell et al. |
|---|---|---|---|
| 5,464,758 | A | 11/1995 | Gossen et al. |
| 5,595,889 | A | 1/1997 | Richaud et al. |
| 5,677,170 | A | 10/1997 | Devine et al. |
| 5,719,055 | A | 2/1998 | Cooper |
| 5,814,618 | A | 9/1998 | Bujard et al. |
| 5,879,933 | A | 3/1999 | Hodgson |
| 5,928,888 | A | 7/1999 | Whitney |
| 5,948,681 | A | 9/1999 | Scanlin et al. |
| 6,013,240 | A | 1/2000 | Behr et al. |
| 6,051,430 | A | 4/2000 | Plasterk et al. |
| 6,225,121 | B1 | 5/2001 | Savakis et al. |
| 6,489,458 | B1 | 12/2002 | Hackett et al. |
| 2002/0016975 | A1 | 2/2002 | Hackett et al. |
| 2002/0103152 | A1 | 8/2002 | Kay et al. |
| 2005/0003542 | A1 | 1/2005 | Kay et al. |

FOREIGN PATENT DOCUMENTS

| EP | 0 485 701 A1 | 5/1992 |
|---|---|---|
| EP | 0 756 007 A2 | 1/1997 |
| WO | WO 88/01646 | 3/1988 |
| WO | WO 93/04701 | 3/1993 |
| WO | WO 93/25239 | 12/1993 |
| WO | WO 95/01095 | 1/1995 |
| WO | WO 96/01313 | 1/1996 |
| WO | WO 96/40892 | 12/1996 |
| WO | WO 97/15679 | 5/1997 |
| WO | WO 97/29202 | 8/1997 |
| WO | WO 98/24479 | 6/1998 |
| WO | WO 98/40510 | 9/1998 |
| WO | WO 98/56903 | 12/1998 |
| WO | WO 99/25817 | 5/1999 |
| WO | WO 99/59546 | 11/1999 |
| WO | WO 00/30687 | 6/2000 |
| WO | WO 00/68399 | 11/2000 |
| WO | WO 01/30965 A2 | 5/2001 |
| WO | WO 02/13602 A1 | 6/2001 |
| WO | WO 01/81565 A2 | 11/2001 |
| WO | WO 01/89579 A2 | 11/2001 |
| WO | WO 01/91802 A1 | 12/2001 |
| WO | WO 01/89579 A3 | 8/2002 |

OTHER PUBLICATIONS

Aldaz et al., "The Interwoven Architecture of the Mu Transposase Couples DNA Synapsis to Catalysis," *Cell*, 1996;85:257-269.
Baker et al., "Division of Labor among Monomers withtin the Mu Transposase Tetramer," *Cell*, 1993;74:723-733.
Birkenmeier et al., "Murine Mucopolysaccharidosis Type VII. Characterization of a Mouse with β-Glucuronidase Deficiency," *J. Clin. Invest.*, 1989;83(3):1258-1266.
Critchlow et al., "DNA end-joining: from yeast to man," *Trends Biochem. Sci.*, 1998;23:394-398.
Davis, "Polyethylenimine," *Water Soluble Resins*, Technical Service and Development, the Dow Chemical Company, Midland, MI, 216-226.
Fermentas, "ExGen™ 500 in vivo Transfection Reagent," [online]; retrieved on Apr. 4, 2002, retrieved from the Internet:<URL:http://www.fermentas.com/profiles/reagents/pexgen500(20x).htm>;4 pgs.

(Continued)

*Primary Examiner*—Joseph Woitach
(74) *Attorney, Agent, or Firm*—Mueting, Raasch & Gebhardt, P.A.

(57) ABSTRACT

The present invention provides for transposon vectors encoding expression control region-traps and gene-traps. Also provided are dicistronic vectors. Certain embodiments of the invention contain internal ribosome entry sites.

29 Claims, 20 Drawing Sheets

OTHER PUBLICATIONS

Fischer et al., "Cis requirements for transposition of Tc1-like transposons in *C. elegans,*" *Mol. Gen. Genet.*, 1999;262:268-274.

Garrick et al., "Repeat-induced gene silencing in mammals," *Nature Genetics*, 1998;18:56-59.

Hackett, Perry B., "Zebrafish as a Model System for Biomedical Research," Grant Abstract, Grant No. 5R01RR006625-07 [online]. National Center for Research Sources, [retrieved on Jan. 20, 2004]. Retrieved from the Internet:<URL:http//crisp.cit.nih.gov/crisp/CRISP_LIB.getdoc?textkey=6056703&p_grant_num=5R01RR006625-07&p_. . . >; 2 pgs.

Hackett, Perry B., "Sleeping Beauty Transposon for Gene Therapy," Grant Abstract, Grant No. 5P01HD032652-070006 [online]. National Institute of Child Health and Human Development, [retrieved on Oct. 29, 2003]. Retrieved from the Internet:<URL:http//crisp.cit.nih.gov/crips/CRISP_LIB.getdoc?textkey=6442591&p_grant_num=5P01 . . . >; 2 pgs.

Hackett et al., "Activity of the Sleeping Beauty System in Mammalian Cells," Keystone Meeting on Molecular and Cellular Biology of Gene Therapy, UT, Abstract, Jan. 14-20, 1999, 1 pg.

Henikoff, "Conspiracy of silence among repeated transgenes," *BioEssays*, 1998;20(7):532-535.

Ivics et al., "Molecular Reconstitution of an Active Tc1-like Transposable Element in Salmonid Fish," Keystone Symp. on Transposition and Site-Specific Recombination, Santa Fe, NM, Abstract, Mar. 1-8, 1997, 1 pg.

Ivics et al., "Molecular Reconstitution of an Active Tc1-like Transposable Element in Salmonid Fish," 4th Intl. Biotechnology Conf., Sorrento, Italy, Abstract, Sep. 22-29, 1997, 1 pg.

Ivics et al., "Molecular Archeology and the Development of Sleeping Beauty: a Novel Transposon for Gene Delivery in Vertebrates," Cold Spring Harbor Meeting on Zebrafish Genetics and Development, CSH Laboratory, NY, Abstract, Apr. 29-May 3, 1998, 1 pg.

Izsvak et al., "Characterization of a Tc1-like Repetitive Element in Zebrafish," Cold Spring Harbor Meeting on Zebrafish, Abstract, Apr. 27-May 1, 1994:2 pgs.

Izsvak et al., "Composite Retroposons and Inverted Repeat Elements for Phylogenetic Analyses and Genetic Mapping in Zebrafish (*Danio rerio*)," Keystone Symp. on Transposition and Site-Specific Recombination, Santa Fe, NM, Abstract, Mar. 1-8, 1997, 1 pg.

Izsvak et al., "Composite Retroposons and Inverted Repeat Elements for Phylogenetic Analyses and Genetic Mapping in Fish," 4th Intl. Biotechnology Conf., Sorrento, Italy, Abstract, Sep. 22-29, 1997, 1 pg.

Izsvak et al., "Evolution and Genetic Applications of Retroposons and Inverted Repeat Transposable Elements in Zebrafish," Cold Spring Harbor Meeting on Zebrafish Genetics and Development, CSH Laboratory, NY, Abstract, Apr. 29-May 3, 1998, 1 pg.

Kawakami et al., "Excision of the *Tol2* transposable element of the medaka fish, *Oryzias latipes*, in zebrafish, *Danio rerio,*" *Gene*, 1998;225:17-22.

Kawakami et al., "Identification of the *Tol2* transposase of the medaka fish *Oryzias latipes* that catalyzes excision of a nonautonomous *Tol2* element in zebrafish *Danio rerio,*" *Gene*, 1999;240:239-244.

Ketting et al., "Target choice determinants of the Tc1 transposon of *Caenorhabditis elegans,*" *Nucl. Acids Res.*, 1997;25(20):4041-4047.

Lampe et al., "Factors Affecting Transposition of the *Himar 1 mariner* Transposon *in Vitro,*" *Genetics*, 1998;149:179-187.

Liu et al., "Functional Analysis of Elements Affecting Expression of the β-Actin Gene of Carp," *Mol. Cell Biol.*, 1990;10(7):3432-3440.

Liu et al., "Hydrodynamics-based transfection in animals by systemic administration of plasmid DNA," *Gene Ther.*, 1999;6:1258-1266.

Mohn et al., "Transposon-Mediated Transgenesis Allows Stable Expression Following Germ-Line Transmission" Cold Spring Harbor Meeting on Zebrafish Genetics and Development, CSH Laboratory, NY, Abstract, Apr. 29-May 3, 1998, 1 pg.

National Center for Biotechnology Information, National Library of Medicine, National Institutes of Health, GenBank Locus AAD03792, Accession No. U89799.1, "Tc1-like transposase [*Anopheles gambiae*]," [online]. Bethesda, MD [retrieved on Oct. 22, 2003]. Retrieved from the Internet:<URL:<http://www.ncbi.nlm.nih.gov/entrez/query.fcgi?cmd=Retrieve&db=protein&list_uids=40 . . . , 2 pages.

National Center for Biotechnology Information, National Library of Medicine, National Institutes of Health, GenBank Locus AAD03793, Accession No. U89800.1, "Tc1-like transposase [*Anopheles gambiae*]," [online]. Bethesda, MD [retrieved on Oct. 22, 2003]. Retrieved from the Internet:<URL:<http://www.ncbi.nlm.nih.gov/entrez/query.fcgi?cmd=Retrieve&db=protein&list_uids=40 . . . , 2 pages.

National Center for Biotechnology Information, National Library of Medicine, National Institutes of Health, GenBank Locus AAD03794, Accession No. U89803.1, "Tc1-like transposase [ *Anopheles gambiae*]," [online]. Bethesda, MD [retrieved on Oct. 22, 2003]. Retrieved from the Internet:<URL:<http://www.ncbi.nlm.nih.gov/entrez/query.fcgi?cmd=Retrieve&db=protein&list_uids=40 . . . , 2 pages.

National Center for Biotechnology Information, National Library of Medicine, National Institutes of Health, GenBank Locus CAA82359, Accession No. Z29098.1, "transposase (putative) [*Drosophila hydei*]," [online]. Bethesda, MD [retrieved on Oct. 22, 2003]. Retrieved from the Internet:<URL:<http://www.ncbi.nlm.nih.gov/entrez/query.fcgi?cmd=Retrieve&db=protein&list_uids=43 . . . , 2 pages.

National Center for Biotechnology Information, National Library of Medicine, National Institutes of Health, GenBank Locus S26856, Accession No. S26856, "transposase—fruit fly (*Drosophila hydei*) transposon Minos," [online]. Bethesda, MD [retrieved on Oct. 22, 2003]. Retrieved from the Internet:<URL:<http://www.ncbi.nlm.nih.gov/entrez/query.fcgi?cmd=Retireve&db=protein&list_uids=28 . . . , 2 pages.

National Center for Biotechnology Information, National Library of Medicine, National Institutes of Health, GenBank Locus CAB51371, Accession No. AJ249084.1, "transposase [*Pleuronectes platessa*]," [online]. Bethesda, MD [retrieved on Oct. 22, 2003]. Retrieved from the Internet:<URL:<http://www.ncbi.nlm.nih.gov/entrez/query.fcgi?cmd=Retrieve&db=protein&list_uids=55 . . . , 2 pages.

National Center for Biotechnology Information, National Library of Medicine, National Institutes of Health, GenBank Locus CAB51372, Accession No. AJ249085.1, "transposase [*Pleuronectes platessa*]," [online]. Bethesda, MD [retrieved on Oct. 22, 2003]. Retrieved from the Internet:<URL:<http://www.ncbi.nlm.nih.gov/entrez/query.fcgi?cmd=Retrieve&db=protein&list_uids=55 . . . , 2 pages.

National Center for Biotechnology Information, National Library of Medicine, National Institutes of Health, GenBank Locus CAC28060, Accession No. AJ303069.1, "putative trasnposase [*Pleuronectes platessa*]," [online]. Bethesda, MD [retrieved on Oct. 22, 2003]. Retrieved from the Internet:<URL:<http://www.ncbi.nlm.nih.gov/entrez/query.fcgi?cmd=Retrieve&db=protein&list_uids=12 . . . , 2 pages.

National Center for Biotechnology Information, National Library of Medicine, National Institutes of Health, GenBank Locus AAB02109, Accession No. L76231.1, "transposase [*Anopheles albimanus*]," [online]. Bethesda, MD [retrieved on Oct. 22, 2003]. Retrieved from the Internet:<URL:<http://www.ncbi.nlm.nih.gov/entrez/query.fcgi?cmd=Retrieve&db=protein&list_uids=11 . . . , 1 pg.

National Center for Biotechnology Information, National Library of Medicine, National Institutes of Health, GenBank Locus S33560, Accession No. S33560, "hypothetical protein—fruit fly (*Drosophila melanogaster*) transposon-like element Bari-1," [online]. Bethesda, MD [retrieved on Oct. 22, 2003]. Retrieved from the Internet:<URL:<http://www.ncbi.nlm.nih.gov/entrez/query.fcgi?cmd=Retrieve&db=protein&list_uids=63 . . . , 2 pages.

National Center for Biotechnology Information, National Library of Medicine, National Institutes of Health, GenBank Locus B46189, Accession No. B46189, "orf within vasotocin gene (Tes1 element)—Pacific hagfish," [online]. Bethesda, MD [retrieved on Oct. 22, 2003]. Retrieved from the Internet:<URL:<http://www.ncbi.nlm.nih.gov/entrez/query.fcgi?cmd=Retrieve&db=protein&list_uids=42 . . . , 1 page.
National Center for Biotechnology Information, National Library of Medicine, National Institues of Health, GenBank Locus CAB63420, Accession No. Z99288.1, "Hypothetical protein ZK262.5 [*Caenorhabditis elegans*]," [online]. Bethesda, MD [retrieved on Oct. 22, 2003]. Retrieved from the Internet:<URL:<http://www.ncbi.nlm.nih.gov/entrez/query.fcgi?cmd=Retrieve&db=protein&list_uids=65 . . . , 2 pages.
Savilahti et al., "Mu Transpositional Recombination: Donor DNA Cleavage and Strand Transfer in *trans* by the Mu Transposase," *Cell*, 1996;85:271-280.
Schleif, "DNA Looping," *Science*, 1988;240:127-128.
Shapiro, "Natural genetic engineering in evolution," *Genetica*, 1992;86:99-111.
Stein et al., Eds., "IUPAC-IUB Commission on biochemical Nomenclature A One-Letter Notation for Amino Acids Tenative Rules," *Journal of Biological Chemistry*, 1968;243(13):3557-3559.
Adey et al., "Molecular resurrection of an extinct ancestral promoter for mouse Li," *Proc. Natl. Acad. Sci. USA*, 1994;91:1569-73.
Allende et al., "Insertional mutagenesis in zebrafish identifies two novel genes, *pescadillo* and *dead eye*, essential for embryonic development," *Genes Dev.*, 1996: 10:3141-55.
Amsterdam et al., "The *Aequorea victoria* green fluorescent protein can be used as a reporter in live zebrafish embryos," *Dev Biol.*, 171(1):123-9 (1995).
Anderson et al., "Gene expression in rainbow trout (*Oncorhynchus mykiss*) following intramuscular injection of DNA," *Mol. Mar. Biol. Biotech.*, 1996;5: 105-13.
Ausubel, "Current Protocols in Molecular Biology," Contents: vols. 1, 2, and 3, 1994; Tables of Contents.
BD biosciences Clontech Company, "Bidirectional Tet Expression Vectors, Simultaneously control expression of two genes with one tet-responsive element," [online] Palo Alto, CA [retrieved on Apr. 25, 2000]. Retrieved from the Internet: <http://www.clontech.com/archive/OCT96UPD/pBIVectors.html>; 3 pages.
BD Biosciences Clontech Company, "Tet Expression Systems & Cell Lines, Mammalian cell cultures systems for tightly regulated, high-level gene expression," [online] Palo Alto, CA [retrieved on May 30, 2000]. Retrieved from the Internet: <http://www.clontech.com/archive/JUL96UPD/Tet.html>, 6 pages.
BD Biosciences Clontech Company, "Tet System Vectors & Primers, Complete your Tet Systems tool kit with individual regulator and selection plasmids," [online] Palo Alto, CA [retrieved on Apr. 23, 2000]. Retrieved from the Internet: <http://www.clontech.com/archive/OCT96UPD/TetVectors.html>, 3 pages.
Ballinger et al., "Targeted gene mutations in *Drosophila*," *Proc. Natl. Acad. Sci. USA*, 1989; 86:9204-6.
Bandyopadhyay et al., "Enhanced gene transfer into HuH-7 cells and primary rat hepatocytes using targeted liposomes and polyethylenimine," *Biotechniques*. 25(2):282-92 (Aug., 1998).
Bandyopadhyay et al., "Nucleotide exchange in genomic DNA of rat hepatocytes using RNA/DNA oligonucleotides. Targeted delivery of liposomes and polyethyleneimine to the asialoglycoprotein receptor," *J Biol Chem.*, 274(15):10163-72 (1999).
Bayer et al., "A transgene containing *lacZ* is expressed in primary sensor neurons in zebrafish," *The Company of Biologists Limited*, 115:421-426 (1992).
Becker et al., "Chapter 8: Use of Recombinant Adenovirus for Metabolic Engineering of Mammalian Cells," *Methods in Cell Biology, vol. 43: Protein Expression in Animal Cells*, Roth, ed., Academic Press, New York, Title page, publication page, table of contents, 1994: pp. 161-189.
Beckwith, "lac: The Genetic System," *The Operon*, second edition, Miller et al., eds., Cold Spring Harbor Laboratory Press, New York, Title page, publication page, table of contents, 1980; pp. 11-30.
Bellen et al., "P-element-medicated enhancer detection: a versatile method to study development in *Drosophila*," *Genes Dev.*, 1989; 3:1288-1300.
Bellon et al., "Aerosol Administration of a Recombinant Adenovirus Expressing CFTR to Cystic Fibrosis Patients: A Phase I Clinical Trial," *Human Gene Ther.*, 1997: 8(1):15-25.

Bingham et al., "Cloning of DNA Sequences from the white Locus of D. melanogaster by a Novel and General Method," *Cell*, 1981; 25:693-704.
Blazar et al., "*In utero* transfer of adult bone marrow cells into recipients with severe combined immunodeficiency disorder yields lymphoid progeny with T-and B-cell functional capabilities," *Blood*, 86(11):4353-66 (1995).
Bonaldo et al., "Efficient gene trap screening for novel developmental genes using IRES beta geo vector and in vitro preselection," *Exper. Cell. Res.*, Oct. 10, 1998;244(1):125-36.
Borman et al., "Comparison of picornaviral IRES-driven internal initiation of translation in cultured cells of different origins," *Nucleic Acids Res.*, 1997; 25:925-32.
Borman et al., Picornavirus internal ribosome entry segments: comparison of translation efficiency and the requirements for optimal internal initiation of translation in vitro, *Nucleic Acids Res.*, 1995; 23:3656-63.
Bosma et al., "Bilirubin UDP-glucuronosyltransferase 1 is the Only Relevant Bilirubin Glucuronidating Isoform in Man," *J. Biol. Chem.* 269, 17960-17964 (1994).
Boussif et al., "A versatile vector for gene and oligonucleotide transfer into cells in culture and *in vivo*: polyethylenimine," *Proc. Natl. Acad. Sci. USA*., 92(16):7297-301 (1995).
Bradley et al., "Formation of germ-line chimaeras from embryo-derived teratocarcinoma cell lines," *Nature*, 1984; 309:255-6.
Bragonzi et al., "Comparison between cationic polymers and lipids in mediating systemic gene delivery to the lungs," *Gene Ther.*, 6, 1995-2004 (1999).
Burcin et al., "Adenovirus-mediated regulable target gene expression *in vivo*," *Proc. Nat'l Acad. Sci. USA*, Jan. 19, 1999; 96:355-360.
Caldovic et al., "Development of position-independent expression vectors and their transfer into transgenic fish," *Molecular Marine Biology and Biotechnology*, 1995; 4:51-61.
Carey, "On the Trail of the Jumping Genes," *Business Week*, p. 89 (Jun. 29, 1998).
Choi et al., "Lactose-Poly(ethylene Glycol)-Grafted Poly-L-Lysine as Hepatoma Cell-Targeted Gene Carrier," *Bioconjugate Chem.*, 9:708-718 (1998).
Chowdhury et al., "Gunn rat: a model for inherited deficiency of bilirubin glucuronidation," *Adv. Vet. Sci. Comp. Med.*, 37:149-73 (1993).
Chowdhury et al., "Isolation of Multiple Normal and Functionally Defective Forms of Uridine Diphoshate-Glucuronosyltransferase from Inbred Gunn Rats," *J. Clin. Invest.*, 79, 327-334 (1987).
Clark et al., "Development of Dicistronic Vectors for Analysis of Transgene Expression in Zebrafish," Abstract presented at the 1998 meeting on "Zebrafish Development and Genetics," Cold Spring Harbor Laboratory, Cold Spring Harbor, NY (Apr. 29-May 3, 1998).
Clarke et al., "pPV: a novel IRES-containing vector to facilitate plasmid immunization and antibody response characterization," *Immunotechnology*, 1997; 3:145-153.
Collas et al., "The nuclear localization sequence of the SW40T antigen promotes transgene uptake and expression in zebrafish embryo nuclei," *Transgenic Res.*, 1996; 5:451-8.
Colloms et al., "DNA binding activities of the Caenorhabditis elegans Tc3 transposase," *Nucl. Acids Res.*, 1994; 22:5548-54.
Cooley et al., "Insertioanl Mutagenesis of the *Drosophila* Genome with Single P Elements," *Science*, 1988; 239:1121-8.
Cormack et al., FACS-optimizing mutants of the green fluorescent protein (GFP), *Gene*, 1996; 173:33-38.
Craig, "Target site selection in transposition," *Am. Rev. Biochem.*, 1997; 66:437-74.
Crameri et al., "Improved green fluorescent protein by molecular evolution using DNA shuffling," *Nat. Biotechnology*, 1996;14(3):315-319.
Curcio et al., "Regulation of retrotransposition in *Saccharomyces cerevisiae*," *Mol. Microbiol.*, 1991; 5(8):1823:1829.
Cusick, "Jumpy Gene Brought Back to Life," *ScienceNOW*, Nov. 1, 1997; 1 page.
Dalton et al., "Separation of Recombinant Human Protein C from Transgenic Animal Milk Using Immobilized Metal Affinity Chromatography," *Adv. Exp. Med. Biol.*, 1997; 411:419-28.

Dawson et al., "Sleeping beauty awakes," *Nature Biotechnology*, 1998; 16:20-1.

Devon et al., "Splinkerettes—improved vectorettes for greater efficiency in PCR walking," *Nucl. Acids. Res.*, 1995; 23:1644-5.

Diebold et al., "Mannose Polyethylenimine Conjugates for Targeted DNA Delivery into Dendritic Cells," *The Journal of Biological Chemistry*, 274(27):19087-19094 (1999).

Doak et al., "a proposed superfamily of transposase genes: Transposon-like elements in ciliated protozoa and a common 'D35E' motif," 1994; *Proc. Natl. Acad. Sci. USA*, 91:942-6.

Dubois et al., "Colorimetric Method for Determination of Sugars and related substances," *Anal. Chem.*, 28(3), 350-6 (1956).

Dupuy et al., "Adapting the *Sleeping Beauty* Transposon for Insertional Mutagenesis in the Mouse," Abstract presented at the 1998 meeting on "Mouse Molecular Genetics," Cold Spring Harbor Laboratory, Cold Spring Harbor, NY (Sep. 2-Sep. 6, 1998).

Ebert et al., "a Moloney MLV-rat somatotropin fusion gene produces biologically active somatotropin in a transgenic pig," *Molecular Endrocrinology*, Mar. 1988; 2(3):277-83.

Eck et al., "Chapter 5: Gene-Based Therapy," Goodman & Gilman's The Pharmacological Basis of Therapeutics, 1996; 77-101.

Economy Polymers and Chemicals, "Economy Products—Polyethyleneimine," product literature [online]; Houston, TX; [retrieved on May 10, 2001]; Retrieved from the Internet: URL:<http://www.economypolymers.com/polethyl.htm>; 2 pages.

Erbacher et al., "Transfection and physical properties of various saccharide, poly(ethylene glycol), and antibody-derivatized polyethylenimines (PEI)," *J. Gene Med.*, 1(3):210-22 (1999).

Essner et al., "Expression of Zebrafish *connexin43.4* in the Notochord and Tail Bud of Wild-Type and Mutant *no tail* Embryos," *Developmental Biology*, 177:449-462 (1996).

Essner et al., "The zebrafish thyroid hormone recptor α1 is expressed during early embryogenesis and can function in transcriptional repression," *Differentiation*, 62:107-117 (1997).

Evans et al., "Gene trapping and functional genomics," *Trends Genet.*, 1997; 13:370-4.

Fadool et al., "Transposition of the *mariner* element from *Drosophila mauritiana* in zebrafish," *Proc. Nat'l. Acad. Sci. USA*, Apr. 1998; 95(9):5182-8186.

Fahrenkrug et al., "Dicistronic Gene Expression in Developing Zebrafish," *Mar. Biotechnol.*, 1:552-561 (1999).

Ferry et al., "Liver-Directed Gene Transfer Vectors," *Human Gene Ther.*, Sep. 20, 1998; 9(14):1975-1981.

Ficck et al., "Modifications of the *E. coli* Lac repressor for expression in eukaryotic cells: effects of nuclear signal sequences on protein activity and nuclear accumulation," *Nuc. Acids Res.*, 1992; 20(7):1785-1791.

Finkelstein et al., "The use of bi-cistronic transfer vectors for the baculovirus expression system," *J. Biotechnol.*, Sep. 24, 1999; 75(1):33-44.

Fire et al., "A modular set of *lacZ* fusion vectors for studying gene expression in *Caenorhabditis elegans,*" *Gene*, 1990; 93(2):189-198.

Fletcher et al., "Mariner Transposon Mediated Stable Integration of Adenoviral Sequences for Use as Gene Therapy Vector System," Abstract 608, Fortieth Annual Meeting, American Society of Hematology, Miami Beach, Dec. 4-8, *Blood*, Nov. 15, 1998; 92(10 Suppl. Part 1 of 2): 151a.

Ghattas et al., "The Encephalomyocarditis Virus Internal Ribosome Entry Site Allows Efficient Coexpression of Two Genes from a Recombinant Provirus in Cultured Cells and in Embryos," *Mol. Cell. Biol.*, 1991; 11:5848-59.

Gibbs et al., "Inheritance of P element and reporter gene sequences in zebrafish," *Mol. Mar. Biol. Biotech.*, 1994; 3:317-26.

Gierl et al., "TnpA product encoded by the transposable element En-1 of Zea mays is a DNA binding protein," *EMBO J.*, 1988; 7:4045-53.

Gluzman et al., "Helper-free Adenovirus Type-5 Vectors," *Eukaryotic Viral Vectors*, Gluzman, ed., Cold Spring Harbor Laboratory Press, New York, title page, publication page, 1982; 187-192.

Gonzales et al., "Transposon mutagenesis of *Haemophilus paragallinarum* with Tn916," *Vet. Microbiol.*, 1996; 48:283-91.

Goodier et al., "Tc1 Transposon-like Sequences are Widely Distributed in Salmonids," *J. Mol. Biol.*, 1994; 241:26-34.

Gossen et al., "Tight control of gene expression in mammalian cells by tetracycline-responsive promoters," *Proc. Nat'l. Acad. Sci. USA*, 1992; 89(12):5547-5551.

Gossen et al., "Transcriptional Activation by Tetracyclines in Mammalian Cells," *Science*, 1995; 268:1766-1769.

Gray, "The direct coupling of oligosaccharides to proteins and derivatized gels," *Arch. Biochem. Biophys.*, 163(1):426-8 (1974).

Gueiros-Filho et al., "Trans-kingdom Tansposition of the *Drosophila* Element *mariner* Within the Protozoan *Leishmaina,*" *Science*, 276:1716-1719 (1997).

Guo et al., "Receptor-targeted gene delivery via folate-conjugated polytheylenimine," *AAPS pharmsci electronic resource*, 1(4):E19 (1999).

Gurtu et al., "IRES Bicistronic Expression Vectors for Efficient Creation of Stable Mammalian Cell Lines," *Biochemical and Biophysical Research Communications*, 1996; 229:295-298.

Hackett et al., "Construction of a Transposon System Active in Human Cells," *Keystone Symposia on Molecular & Cellular Biology*, Abstract and Poster, Jan. 20, 1998.

Hackett et al., "Chapter 2: Development of Genetic Tools for Transgenic Animals," in: Murray et al., *Transgenic Animals in Agriculture*, CABI Publishing, New York, 1999; 19-35. (Presentation from a conference held in California in Aug. 1997).

Hackett et al., "Development of Genetic Tools for Transgenic Fish," Abstract, Seminars in Singapore, Jul. 29-30, 1997 & UC Davis Biotechnology Program, Granlibakken Conference Center, Aug. 24-27, 1997.

Hackett et al., "Sleeping Beatuy Transposon For Gene Therapy," Grant Abstract, Grant No. 2P01HD032652-060006 [online]. National Institute of Child Health and Human Development, National Institutes of Health, project dates Jan. 10, 1995-Dec. 31, 2002 [retrieved on Jun. 19, 2001]. Retrieved from the Internet:URL:http://commons.cit.nib.gov/crisp3/crisp_lib. getdoc?textkey=6325542&p_grant_num=2P01HD032652-060006&p_query=&ticket=16646&p_audit_session_id=381420 &p_keywords=. 2 pages.

Hackett et al., "The molecular biology of transgenic fish," *Biochemistry and Molecular Biology of Fishes*, Hochachka and Mommsen, Eds., 1993; 2:207-40.

Hackett et al., "Zebrafish as a model system for biomedical research," Grant Abstract, Grant No. 2R01RR06625-05A1 [online]. National Center for research Resources, National Institutes of Health, project dates Aug. 1, 1991-Aug. 31, 2000 [retrieved on Apr. 11, 2001]. Retrieved from the Internet: URL:http://commons.cit. nih.gov/crisp_historical/crisp_lib.getdoc?textkey=2397786 &p_grant_num=2R01RR06625_05A1&p_query= &ticket=73379&p_audit_session_id=425461&p_keywords=, 2 pages.

Hackett et al., "Zebrafish as a Model System For Biomedical Research," Grant Abstract, Grant No. 5R01RR006625-06 [online]. National Center for Research Resources, National Institutes of Health, project dates Aug. 1, 1991-Aug. 31, 2000 [retrieved on Jun. 19, 2001]. Retrieved from the Internet: URL: http://commons.cit. nih.gov/crisp3/crisp_lib.getdoc?textkey=2772010 &p_grant_num=5R01RR006625-06&p_query=&ticket=16646 &p_audit_session_id=381420&p_keywords=, 2 pages.

Hallet et al., "Transposition and site-specific recombination: adapting DNA cut-and-past mechanisms to a variety of genetic rearrangements," *FEMS Microbiol. Rev.*, Sep. 1997; 21(2):157-78.

Hammer et al., "Genetic engineering of mammalian embryos," *J. Anim. Sci.*, Jul. 1986; 63(1):269-78.

Handler et al., "A Functional Analysis of the P-Element Gene-Transfer Vector in Insects," *Arch. Insect Biochem. Physiol.*, 1993; 22:373-84.

Hardy et al., "Construction of Adenovirus Vectors through Cre-*lox* Recombination," *J. Virol.*, 71(3):1842-1849 (1997).

Harlow et al., eds., *Antibodies: A Laboratory Manual*, Cold Spring Harbor Laboratory Press, Cold Spring Harbor, New York, NY ; copyright page and table of contents: 9 pages (1988).

Hartl, Daniel, L., "*Mariner* Sails into *Leishmania,*" *Science*, 276, 1659-1660 (Jun. 13, 1997).

Hartl et al., "What restrict the activity of mariner-like transposable elements," *Trends Genet.*, 1997; 13:197-201.

Hellen et al., "Translation of Encephalomyocarditis Virus RNA by Internal Ribosomal Entry," *Curr. Top. Microbiol. Immunol.*, 1995; 203:31-63.
Hirt, "Selective Extraction of Polyoma DNA from Infected Mouse Cell Cultures," *J. Mol. Biol.*, 1967; 26(2):365-369.
Horie et al., "Efficient Chromosomal Transposition of Tc1/Mariner-like Transposon Sleeping Beauty in Mice," *PNAS*, 98(16):9191-9196 (2001).
Hu et al., "The Inducible lac Operon-Repressor System Is Functional in Mammalian Cells," *Cell*, 1987; 48(4):555-566.
Ivics et al., "Development of Tc1-like transposable elements as genetic tools for Zebrafish (*Danio rerio*)," Abstract presented at "Second Biennial Meeting on Zebrafish Development and Genetics", Cold Spring Harbor Laboratory, Cold Spring Harbor, NY (Apr. 24-28, 1996).
Ivics et al., "Genetic Applications of Tansposons and Other Repetitive Elements in Zebrafish," *Meth. Cell Biol.*, 1999; 60, 99-131.
Ivics et al., "Identification of functional domains and evolution of Tc1-like transposable elements," *Proc. Natl. Acad. Sci. USA*, 1996; 93:5008-13.
Ivics et al., "Molecular Reconstruction of Sleeping Beauty, a Tc1-like Transposon from Fish, and Its Transpostion in Human Cells," *Cell*, '97; 91(4):501-10.
Ivics et al., "Repeated Sequence Elements in Zebrafish and Their Use in Molecular Genetic Studies," *The Zebrafish Science Monitor*, 1995; 3:1-4.
Izsvak et al., Characterization of a Tc1-like transposable element in zebrafish (Danio rerio), *Mol. Gen. Genet.*, 1995; 247:312-22.
Izsvak et al., "Involvement of a bifunctional, paired-like DNA-binding domain and a transpositional enhancer in Sleeping beauty transposition," *J. Biol. Chem.*, 277(37):34581-8 (2002).
Izsvak et al., "Nucleic acid sequence alignment and a predicted consensus sequence of the salmonid subfamily of Tc1-like transposable elements isolated from eight fish species," [online]. [retrieved Jun. 5, 2001]. Retrieved from the Internet: <URL:ftp://ftp.ebi.ac.uk/pub/databases/embl/align/ds30090.dat.>; 10 pages.
Izsvak et al., "Repetitive elements and their genetic applications in zebrafish," *Biochem. Cell Biol.*, 1997; 75:507-23.
Izsvak et al., "*Sleeping Beauty*, a wide host-range transposon vector for genetic transformation in vertebrates," *J. Mol. Biol.*, 302, 93-102 (2000).
Izsvak et al., "Two-Stage Ligation-Mediated PCR Enhances the Detection of Integrated Transgenic DNA," *BioTechniques*, 1993; 15, 814, 816, and 817.
Jang et al., "Cap-independent translation of encephalomyocarditis virus RNA: structural elements of the internal ribosomal entry site and involvement of a cellular 57-kD RNA-binding protein," *Genes Dev.*, 1990; 4:1560-72.
Jermann et al., "Reconstructing the evolutionary history of the artiodactyl ribonuclease superfamily," *Nature*, 1995; 374:57-9.
Kaiser et al., "Eukaryotic transposable elements as tools to study gene structure and function," in *Mobile Genetic Elements*, Sherratt, David, J., ed., IRL Press at Oxford University Press, Oxford/New York/Tokyo, pp. 69-100 (1995).
Kaminski et al., "Translation of encephalomyocarditis virus RNA: parameters influencing the selection of the internal inititation site," *EMBO J.*, 1994; 13:1673-81.
Kaufman et al., "Improved vectors for stable expression of foreign genes in mammalian cells by use of the untranslated leader sequence from EMC virus," *Nucleic Acids Res.*, 1991; 19(16):4485-90.
Kidwell, "Horizontal transfer," *Curr. Opin. Genet. Dev.*, 1992; 2: 868-73.
Kircheis et al., "Coupling of cell-binding ligands to polyethylenimine for targeted gene delivery," *Gene Ther.*, 4(5):409-18 (1997).
Klotz et al., "Macromolecule-small molecule interactions, Strong binding and cooperativity in a model synthetic polymer," *Biochemistry*, 8(12):4752-6 (1969).
Koga et al., "Transposable element in fish," *Nature*, 1996; 383:30.
Korswagen et al., "Transposon Tc1-derived, sequence-tagged sites in *Caenorhabditis elegans* as markers for gene mapping," *Proc. Natl. Acad. Sci. USA*, 1996; 93: 14680-5.

Koster et al., *MolecularMarine Biology and Biotechnology*, 1996; 5(1):1-8.
Kren et al., "Alterations in mRNA stability during rat liver regeneration," *Am. J. Physiol.*, 270(5 Pt 1):G763-77 (May 1996).
Kren et al., "Correction of the UDP-glucuronosyltransferase gene defect in the Gunn rat model of Crigler-Najjar Syndrome type I with a chimeric oligonucleotide," *Proc. Natl. Acad. Sci. USA*, 96(18):10349-54 (1999).
Kutty et al., "Purification and Characterization of Biliverdin Reductase from Rat Liver," *J. Biol. Chem.* 256, 3956-3962 (1981).
Lam et al., "Discovery of Amphibian Tc1-like Transposon Families," *J. Mol. Biol.*, 1996; 257:359-366.
Lam et al., "Active transposition in zebrafish," *Proc. Natl. Acad. Sci. USA*, 1996; 93:10870-5.
Lampe et al., "A purified mariner transposase is sufficient to mediate transposition in vitro," *EMBO J.*, 1996; 15:5470-9.
Larregina et al., "FasL induces Fas/Apo1-mediated apoptosis in human embryonic kidney 293 cells routinely used to generate E1-deleted adenoviral vectors," *Gene Ther.*, Apr. 1998;5(4):563-568.
Lee et al., "Tn 10 insertional mutagenesis in *Pasteurella multocida*," *Vet. Microbiol.*, 1996; 50:143-148.
Lewin, "Eukaryotic mRNAs have a methylated cap at the 5' end," Oxford University Press, *Genes VI*, 1997; pp. 171-172.
Lewin, "Nuclear splicing proceeds through a lariat," Oxford University Press, *Genes VI*, 1997; pp. 891-893.
Li et al., "Inversion and transposition of Tc1 transposon of *C. elegans* in mammalian cells," *Somat. Cell Mol. Genet.*, 24(6):363-369 (Nov. 1998).
Linehan-Stieers et al., "Uniform distribution and long-term expression of GFP in liver mediated by the Sleeping Beauty transposon system," abstract presented at Fourth Annual Meeting of the American Society of GeneTherapy, Seattle, Washington, May 30-Jun. 3, 2001 (1 page).
Liu et al., "Development of Expression Vectors for Transgenic Fish," *BioTechnol.*, 1990; 8:1268-72.
Liu et al., "Isolation and characterization of β-actin gene of carp (*Cyprinus carpio*)," *DNA Sequence-J. DNA Sequencing and Mapping*, 1990; 1:125-36.
Lohe et al., "Horizontal Transmission, Vertical Inactivation, and Stochastic Loss of *Mariner*-like Transposable Elements," *Mol. Biol. Evol.*, 1995; 12(1):62-72.
Lohe et al., "Mutations in the mariner transposase: The D, D(35)E consensus sequence is nonfunctional," *Proc. Natl. Acad. Sci. USA*, 1997; 94:1293-7.
Lönngren et al., "Aldonate coupling, a simple procedure for the preparation of carbohydrate-protein conjugates for studies of carbohydrate-binding proteins," *Arch. Biochem. Biophys.*, 175(2):661-9 (1976).
Loukeris et al., "Gene Transfer into the Medfly, Ceratitis capitata, with a *Drosophila hydei* Transposable Element," *Science*, 1995; 270:2002-5.
Lubon et al., "Blood Proteins from Transgenic Animal Bioreactors," *Transfusion Med. Rev.*. 1996; 10:131-143.
Luo et al., "Chromosomal transposition of a Tc1/mariner-like element in mouse embryonic stem cells," *Proc. Natl. Acad. Sci. USA*, 1998; 95:10769-73.
Markkula et al., "Transgenic animals and gonadotrophins," *Rev. Reprod.*, 1996; 1:97-106.
Marshall, "Gene Therapy on Trial," *Science*, 288, 951-957 (2000).
McGrory et al., "A Simple Technique for the Rescue of Early Region I Mutations into Infectious Human Adenovirus Typy 5," *Virol.*, 1988, 163(2):614-617.
Meng et al., "Promoter analysis in living zebrafish embryos identifies a cis-acting motif required for neuronal expression of GATA-2," *Proc. Natl. Acad. Sci. USA*, 94(12):6267-72 (1997).
Merwin et al., "CD5-mediated specific delivery of DNA to T lymphocytes: compartmentalization augmented by adenovirus," *Journal of Immunological Methods*, 186:257-266 (1995).
Michael, "Mutagenesis by Incorporation of a Phosphorylated Oligo During PCR Amplification," *BioTechniques*, 1994; 16:410-2.
Moav et al. "Regulation of expression of transgenes in developing fish," *Transgenic Research*, 2:153-161 (1993).

Moerman et al., "Chapter 22: Mobile Elements in *Caenorhabditis elegans* and Other Nemotodes," *Mobile DNA*, Berg et al., eds., American Society for Microbiology, Title page, publication page, tabel of contents, 1989; 537-555.

Mohn et al., "Transposon-Mediated Transgenesis allows stable expression following germ-line transmission," Abstract presented at the 1988 meeting on Zebrafish Development & Genetics, Cold Spring Harbor Laboratory, Cold Spring Harbor, NY (Apr. 29-May 3, 1998).

Monsigny et al., Colorimetric determination of neutral sugars by a resorcinol sulfuric acid micromethod, *Anal. Biochem.*, 175(2):525-30 (1988).

Moore et al., "Carbohydrate Characterization I. The Oxidation of Aldoses by Hypoidite in Methanol; II. The Identification of Seven Aldo-Monosaccharides as Benzimidazole Derivatives," *J. Biol. Chem.*, 133, 293-311 (1940).

Morgan et al., "Transposon tools for recombinant DNA manipulation: Characterization of transcriptional regulators from yeast, Xenopus, and mouse," *Proc. Natl. Acad. Sci. USA*, 1996; 93:2801-6.

Morral et al., "Administration of helper-dependent adenoviral vectors and sequential delivery of different vector serotype for long-term liver-directed gene transfer in baboons," *Proc. Nat'l. Acad. Sci. USA*, Oct. 26, 1999; 96(22):12816-12821.

Mountford et al., "Internal ribosome entry sites and dicistronic RNAs in mammalian transgenesis," *Trends Genet.*, 1995; 11:179-84.

Mullins et al., "Transgenesis in the rat and larger mammals," *J. Clinical Invest.*, Apr. 1, 1996; 97(7):1557-60.

National Center for Biotechnology Information, National Library of Medicine, National Institutes of Health, GenBank Locus No. SMOTC1LT, Accession No. L12206, salmo salar (clone TC-TSS1) Tc1-like interspersed repetitive element encoding TcA-like transposase pseudogene) [online]. Bethesda, MD [retrieved on Apr. 14, 2003]. Retrieved from the Internet URL:<http://www.ncbi.nlm.nih.gov/entrez/query.fcgi?cmd=Retrieve&db=nucleotide&list_uids=2 . . . , 2 pages.

National Center for Biotechnology Information, National Library of Medicine, National Institutes of Health, GenBank Locus No. SMOTC1LTA, Accession No. L12207, salmo salar (clone TC-TSS2) Tc1-like interspersed repetitive element and a transposase pseudogene) [online]. Bethesda, MD [retrieved on Apr. 14, 2003]. Retrieved from Internet URL:<http://www.ncbi.nlm.nih.gov/entrez/query.fcgi?cmd=Retrieve&db=nucleotide&list_uids=2 . . . , 2 pages.

National Center for Biotechnology Information, National Library of Medicine, National Institutes of Health, GenBank Locus No. EMCPOLYP, Accession No. M81861, encephalomyocarditis virus polyprotein, complete eds.) [online]. Bethesda, MD [retrieved on Aprl. 14, 2003]. Retrieved from Internet URL:<http://www.ncbi.nlm.nih.gov/entrez/query.fcgi?cmd=Retrieve&db=nucleotide&list_uids=2 . . . , 2 pages.

National Institutes of Health, "BLAST 2 Sequences," [online] Bethesda, MD [retrieved Sep. 15, 2000]. Retrieved from the Internet: <http://www.ncbi.nlm.nih.gov/gorf/b12.html>; 1 page (correction of "BLAST 2 . . . ").

National Institutes of Health, "BLAST 2 Sequences," [online] Bethesda, MD [retrieve Apr. 9, 2002]. Retrieved from the Internet: <http://www.ncbi.nlm.nih.gov/gorf/b12.html>; 1 page.

Okabe et al., "'Green Mice' as a Source of Ubiquitous Green Cells," *FEBS Letters*, 407, 313-319 (1997).

Oosumi et al., "Mariner transposons in humans," 1995; *Nature*, 378:672.

Osborne et al., "Movers and shakers: maize transposons as tools for analyzing other plant genomes," *Curr. Opin. Cell Biol.*, 1995; 7:406-13.

Padgett et al., "Splicing of Messenger RNA Precursors," *Ann. Rev. Biochem. J.*, 1988; 55:1119-1150.

Pan et al., "The Binding Site of the IcIR Repressor Protein Overlaps the Promoter of aceBAK," *Journal of Bacteriology*, Jul. 1996;178(13):3982-3982.

Parks et al., "A helper-dependent adenovirus vector system: Removal of helper virus by Cre-mediated excision of the viral packaging signal," *Proc. Nat'l. Acad. Sci. USA*, 1996; 93:13565-13570.

Pelletier et al., "Internal initiation of translation of eukaryotic mRNA derived from poliovirus RNA," *Nature*, 1988; 334:320-325.

Perucho et al., "Genetic and Physical Linkage of Exogenous Sequences in Transformed Cells," *Cell*, 1980; 22:309-17.

Petrov et al., "Diverse transposable elements are mobilized in hybrid dysgenesis in *Drosophila virilis*," *Proc. Natl. Acad. Sci. USA*, 1995; 92(17):8050-4.

Plasterk, "Molecular Mechanisms of Transposition and Its Control," *Cell*, 1993; 74:781-6.

Plasterk, "Chapter 3: Reverse Genetics: From Gene Sequence to Mutant Worm," *Meth. Cell. Biol.*, Academic Press, Inc., 1995; 8:59-80.

Plasterk, "the Tc1/mariner Transposon Family," *Curr. Top. Microbiol. Immunol.*, 1996; 204:125-143.

Plasterk et al., "Resident aliens of the Tc1/mariner superfamily of transposable elements," *Trends in Genetics*, 1999;15:326-332.

Radice et al., "Widespread occurrence of the Tc1 transposon family: Tc1-like transposons from teleost fish," *Mol. Gen. Genet.*, 1994; 244:606-12.

Raz et al., "Transposition of the nematode *Caenorhabditis elegans* Tc3 element in the zebrafish *Danio rerio*," *Current Biology*, Dec. 12, 1997; 8:82-83,85, 87-88.

Rio et al., "Evidence for Drosophila P Element Transposase Activity in Mammalian Cells and Yeast," *J. Mol. Biol.*, 1988; 200:411-5.

Ryter et al., "Heme oxygenase activity. Current Methods and Applications," *Methods Mol. Biol.*, 99, 369-91 (2000).

Sambrook et al., *Molecular Cloning: A Laboratory Manual*, Cold Spring Harbor Laboratory Press, table of contents and title page, 1989.

Sarkar et al., "The 'Megaprimer' Method of Site-Directed Mutagenesis," *BioTechniques*, 1990; 8:404-407.

Schneider, "BIOPHEX Highlights Gene Therapy Progress," *Gen. Eng. News*, 22(20), 1 (Nov. 15, 2002).

Schouten et al., "Transposon Tc1 of the nematode *Caenorhabditis elegans* jumps in human cells," *Nucleic Acids Research*, 1998; 26(12):3013-7.

Sequence search results cited by Examiner in U.S. Appl. No. 09/142,593; titles: US-09-142-593-4; US-09-142-593-5; US-09-142-593-8; and US-09-142-593-7; printed Feb. 1 and Feb. 2, 2000; GenCore version 4.5; 8 pgs.

Sherratt, *Mobile Genetic Elements*, IRL Press, Oxford, 1995.

Smit et al., "Tiggers and other DNA transposon fossils in the human genome," *Proc. Natl. Acad. Sci. USA*, 1996; 93:1443-8.

Snyder et al., "An improved 2.4,6-trinitrobenzenesulfonic acid method for the determination of amines," *Anal. Biochem.*, 64(1):284-8 (1975).

Spradling et al., "Gene disruptions using P transposable elements: An integral component of the Drosophila genome project," *Proc. Natl. Acad. Sci. USA*, 1995; 92:10824-30.

Stewart, "Active ancestral molecules," *Nature*, 1995; 374:12-3.

Suh et al., "Ionization of poly(ethylenimine) and poly(allylamine) at various pH's," *Bioorg. Chem.*, 22(3):318-327 (1994).

Szekely et al., "P element mediated germ line transformation of *Drosophila melanogaster* with the Tc1 transposable DNA element from *Caenorhabditis elegans*," *Genome*, 1994; 37:356-366.

Tatusova et al., "BLAST 2 Sequences, a new tool for comparing protein and nucleotide sequences," *FEMS Microbiol. Lett.*, May 15, 1999; 174(2):247-250.

Trembley et al., "Differential regulation of cyclin B1 RNA and protein expression during hepatocyte growth *in vivo*," *Cell Growth Differ.*, 7(7):903-16 (1996).

Urabe et al., "A novel dicistronic AAV vector using a short IRES segment derived from hepatitis C virus genome," *Gene*, 1997; 200:157-162.

van Luenen et al., "Target site choice of the related transposable elements Tc1 and Tc3 of Caenorhabditis elegans," *Nucleic Acids Research*, 1994; 22:262-9.

van Luenen et al., "Mobilization of quiet, endogenous Tc3 transposons of Caenorhabditis elegans by forced expression of Tc3 transposase," *EMBO J.*, 1993; 12:2513-2520.

van Luenen et al., "The Mechanism of Transposition of Tc3 in *C. elegans*," *Cell*, 1994; 79:293-301.

Verma et al., "Gene Therapy—Promises, Problems, and Prospects," *Nature*, 389, 239-242 (1997).

von Melchner et al., "Identification of Cellular Promoters by Using a Retrovirus Promoter Trap," *J. Virol.*, 1989; 63:3227-33.

Vos et al., "Tc1 transposase of *Caenorhabditis elegans* is an endonuclease with a bipartite DNA binding domain," *EMBO J.*, 1994; 13:6125-32.

Vos et al., "Transposase is the only nematode protein required for in vitro transposition of Tc1," *Genes. Dev.*, 1996; 10:755-61.

Vos et al., "Characterization of the *Caenorhabditis elegans* Tc1 transposase in vivo and in vitro," *Genes Dev.*, 1993; 7:1244-53.

Wall et al., "Transgenic Dairy Cattle: Genetic Engineering on a Large Scale," *J. Dairy Sci.*, 1997; 80:2213-2224.

Warren et al., "'Physiological genomics': Mutant screens in zebrafish,"*Am J Physiol.* 275(1 Pt 2):H1-7 (1998).

Weber et al., "an SV40 'Enhancer Trap' Incorporates Exogenous Enhancers or Generates Enhancers from Its Own Sequences," *Cell*, 1984; 36:983-92.

Weber et al., "Macrolide-based Transgene Control in Mammalian Cells and Mice," *Nature Biotechnology*, 20, 901-907 (2002).

Webster, "One-Step, Two-Step Regulation of Therapeutic Genes," *The Scientists*, available on line at http://www.the-scientist.com/yr1999/apr/opin_990426.html (Apr. 26,1999).

Weinberg, Eric, S., "Zebrafish genetics: Harnessing horizontal gene transfer," *Current Biology*, 8, R244-R247 (1998).

Weng et al., "HO-1 expression in type II pneumocytes after transpulmonary gene delivery," *Am. J. Physiol. Lung Cell. Mol. Physiol.*, 278, L1273-L1279 (2000).

Westerfield, "The Zebrafish Book," University of Oregon Press, Eugene, OR (1995), Title Page & Table of Contents only: text is available at http://www.zfish.uoregon.edu/zf_info/zfbook/zfbk.html.

Yant et al., "The development of new recombinant adenoviral vectors capable of stable integration into mammalian genomes," Abstract 922, p. 232a, 2nd Annual Meeting of the American Society of Gene Therapy, Jun. 9-13, 1999; in Washington, DC.

Yant et al., "Somatic integration and long-term transgene expression in normal and haemophilic mice using a DNA transposon system," *Nat. Genet.*, 25(1):35-41 (May 2000).

Yant et al., "Transposition from a gutless adeno-transposon vector stabilizes transgene expression in vivo," *Nature Biotechnology*, 20(10), 999-1005 (2002).

Ye et al., "Regulated Delivery of Theraupeutic Proteins After in Vivo Somatic Cell Gene Transfer," *Science*, Jan. 1, 1999; 283:88-91.

Yoon et al., "Targeted gene correction of episomal DNA in mammalian cells mediated by a chimeric RNA-DNA oligonucleotide," *Proc. Natl. Acad. Sci. USA*, 1996; 93(5):2071-6.

Young et al., "Production of Biopharmaceutical Proteins in the Milk of Transgenic Dairy Animals," *BIO PHARM*, 1997; 10:34-8.

Youngman et al., "Rte-1, a retrotransposon-like element in *Caenorhabditis elegans*," *FEBS Lett.*, 1996; 380:1-7.

Zambrowicz et al., "Disruption and sequence identification of 2,000 genes in mouse embryonic stem cells," *Nature*, 1998; 392:608-611.

Zhang et al., "The Himar1 mariner transposase cloned in a recombinant adenovirus vector is functional in mammalian cells," *Nuc. Acids Res.*, Aug. 15, 1998; 26(16):3687-3693.

Balciunas et al., "Enhancer trapping in zebrafish using the *Sleeping Beauty* transposon," *BMC Genomics*Sep. 3, 2004;5:62:1-15.

Baus et al., "Hyperactive Transposase Mutants of the *Sleeping Beauty* Transposon," *Mol. Ther.*, Dec. 2005; 12(6):1148-1156. [Epub Sep. 8, 2005].

Belur et al., "Long-term Expression in Mouse Lung After Non-viral Sleeping Beauty-mediated Gene Transfer," *Mol. Therapy*;3:S60, Amer. Soc. Gene Therapy, Seattle, WA, Abstract, May 30-Jun. 3, 2001, 1 pg.

Belur et al., "Sleeping Beauty: A Non-viral Vector System Mediating Long Term Gene Expression in Mouse Lung and Liver," *Mol. Therapy*;5:S322, Amer. Soc. Gene Therapy, Abstract, 2002, 1 pg.

Belur et al., "Hyperoxia-induced Lung-Injury: Treatment with a Heme Oxygenase-1 Transgene Mediated by the Sleeping Beauty Transposon System," Amer. Soc. Gene Therapy, Washington, D.C., Abstract, Jun. 6-10, 2003, 1 pg.

Belur et al., "Gene Insertion and Long-Term Expression in Lung Mediated by the *Sleeping Beauty* Transposon System," *Mol. Therapy*, Sep. 2003;8(3):501-507.

Bestor, "Transposons Reanimated in Mice," *Cell*,:322-325. [Epub DOI:10.1016/j.cell. 2005.07.024].

Bettinger et al., "Size Reduction of Galactosylated PEI/DNA Complexes Improves Lectin-Mediated Gene Transfer into Hepatocytes," *Bioconjugate Chem.*, 1999; 10:558-561.

Carlson et al., "Germline Transposon Mutagenesis of Mouse Using the Sleeping Beauty Transposon System," Mouse Molecular Genetics Meeting, New York, NY, Abstract, Aug. 2002, 1 pg.

Carlson et al., "Transposon Mutagenesis of the Mouse Germline," *Genetics*, Sep. 2003;165: 243-256.

Carlson et al., "Somatic integration of an oncogene-harboring *Sleeping Beauty* transposon models liver tumor development in the mouse," *PNAS*, Nov. 22, 2005; 102(47): 17059-17064. [Epub Nov. 14, 2005].

Carlson et al., "Insertional Mutagenesis in Mice: New Perspectives and Tools," *Nat. Rev. Genet.*, Jul. 2005; 6(7):568-580.

Chen et al., "Gene 'Knockdown' Approaches Using Unconventional Antisense Oligonucleotides," *Fish Development and Genetics, The Zebrafish and Medaka Models*, Hackensack, NJ, 2004, vol. 2, Chap. 13:454-475.

Clark et al., "Sleeping Beauty Goes Fishing: Insertional Mutagenesis Screens Using Transposons," Cold Spring Harbor Meeting on Zebrafish Genetics and Development, CSH Laboratory, NY, Abstract, Apr. 26-30, 2000, 1 pg.

Clark et al., "Sleeping Beauty Transposons for Gene Discovery and Analysis," International Zebrafish Meeting, Madison, WI, Abstract, Jun. 12-16, 2002, 1 pg.

Clark et al., "Transposon Vectors for Gene-Trap Insertional Mutagenesis in Vertebrates," *Genesis*, 2004;39:225-233.

Collier et al., "Cancer gene discovery in solid tumours using transposon-based somatic mutagenesis in the mouse," *Nature*, Jul. 14, 2005; 436(7048):272-276.

Collier et al., "Hopping around the Tumor Genome: Transposons for Cancer Gene Discovery," *Cancer Res.*, Nov. 1, 2005; 65(21):9607-9610.

Collier et al., "Transforming science: cancer gene identification," *Curr. Opin. Genet. Dev.*, Feb. 2006; 16(1):23-29. [Epub Dec. 1, 2005].

Converse et al., "Sleeping Beauty-mediated Transposition I Cultured Human Lung and Liver Cells and Murine Hematopoietic Cells," *Mol. Therapy*;3:S64, Amer. Soc. Gene Therapy, Seattle, WA, Abstract, May 30-Jun. 3, 2001, 1 pg.

Converse et al., "Counterselection and Co-Delivery of Transposon and Transposase Functions for *Sleeping Beauty*-Mediated Transposition in Cultured Mammalian Cells," *Biosci, Rep.*, Dec. 2004; 24(6):577-594.

Cui et al., "Structure-Function Analysis of the Inverted Terminal Repeats of the Sleeping Beauty Transposon," *J. Mol. Biol.*, 2002; 318:1221-1235.

Cui et al., "RecA-mediated, Targeted Mutagenesis in Zebrafish," *Mar. Biotechnol.*, 2003; 5:174-184.

Davidson et al., "Sleeping Beauty: An Efficient Method for Gene Delivery in Zebrafish," International Zebrafish Meeting, WI, Abstract, Jun. 12-16, 2002, 1 pg.

Davidson et al., "Efficient gene delivery and gene expression in zebrafish using the *Sleeping Beauty* transposon," *Dev. Biol.*, 2003;263:191-202.

Ding et al., "Efficient Transposition of the *piggyBac* (*PB*) Transposon in Mammalian Cells and Mice," *Cell*, Aug. 12, 2005; 122:473-483. [Epub DOI 10.1016/j.cell.2005.07.013].

Dupuy et al., "Transposition and Gene Disruption in the Male Germline of the Mouse," *Genesis*, 2001;30:82-88. [received Apr. 27, 2001; accepted May 16, 2001; online pub'l Jun. 13, 2001; journal pub'l Jun. 2001].

Dupuy et al., "Mammalian germ-line transgenesis by transposition," *Proc. Natl. Acad. Sci. USA*, 2002;99(7):4495-4499.

Dupuy et al., "Mammalian mutagenesis using a highly mobile somatic *Sleeping Beauty* transposon system," *Nature*, Jul. 14, 2005; 436(7048):221-226.

Ehrhardt et al., "A Direct Comparison of Two Nonviral Gene Therapy Vectors for Somatic Integration: *In Vivo* Evaluation of the Bacteriophage Integrase φc31 and the *Sleeping Beauty* Transposase," *Mol. Ther.*, May 2005; 11(5):695-706.

Eisenstein, "Wake-up call for *Sleeping Beauty*," *Nat. Methods*, Sep. 2005; 2(9):637.

Ekker, Stephen C., "Insertional Mutagenesis in Zebrafish by SB Transposons," Grant Abstract, Grant No. 5R01DA014546-04 [online]. National Institute on Drug Abuse, project dates May 1, 2001-Mar 31, 2006 [retrieved on Feb. 13, 2006]. Retrieved from the Internet: URL:http://crisp.cit.nih.gov/CRISP_LIB.getdoc?textkey=6736301&p_grant_num=5R01D . . . 2 pgs.

Ekker, Stephen C., "Insertional Mutagenesis in Zebrafish by SB Transposons," Grant Abstract, Grant No. 5R01DA014546-05 [online]. National Institute on Drug Abuse, project dates May 1, 2001-Mar. 31, 2006 [retrieved on Feb. 13, 2006]. Retrieved from the Internet: URL: http://crisp.cit.nih.gov/CRISP_LIB.getdoc?textkey=6881460&p_grant_num=5R01D . . . 2 pgs.

Ekker et al., "The Sleeping Beauty Transposon System in Zebrafish—its Activity in the 21st Century," Cold Spring Harbor Meeting on Zebrafish Genetics and Development, CSH Laboratory, NY, Abstract, Apr. 26-30, 2000, 1 pg.

Essner, Jeffrey J., "Angiogenesis Targets for Therapeutic Development," Grant Abstract, Grant No. 1R43CA108117-01 [online]. National Cancer Institute, project dates Jun. 4, 2004-Nov. 30, 2004 [retrieved on Feb. 13, 2006]. Retrieved from the Internet: URL: http://crisp.cit.nih.gov/CRISP_LIB.getdoc?textkey=6790744&p_grant$_{13}$ num=1R43C . . . 2 pgs.

Essner et al. "Awakening gene therapy with Sleeping Beauty transposons," *Curr. Opin. Pharmacol.*, 2005; 5:513-519.

Geurts et al., "Gene Transfer into Genomes of Human Cells by the *Sleeping Beauty* transposon system," *Mol. Therapy*, Jul. 2003; 8(1):108-117.

Grabher et al., "Transposon-mediated enhancer trapping in medaka," *Gene*, 2003;322:57-66.

Grabher et al., "Efficient activation of gene expression using a heat-shock inducible Ga14/Vp16-UAS system in medaka," *BMC Biotechnol.*, Oct. 26, 2004; 4(26):1-6.

Hackett, "Development of Genetic Tools for Genomic Analyses and Transgenesis in Fish," Biotechnology-Aquaculture Interface, USDA meeting, http://nps.ars.usda.gov/static/ arsiobiotecws2001/contributions/Hackettrev.htm, Shepardstown, WV, Abstract, Mar. 5-7, 2001, 5 pgs.

Hackett, "From Tissue Culture to Whole Animals: Development of Genetic Tools for Genomic Analyses and Transgenesis in Fish," Generation of new marine cell lines and transgenic fish meeting, Mount Desert Island Biological Laboratory, Bar Harbor, ME, Abstract, May 4-6, 2001, 2 pgs.

Hackett, "The R's of the Life Sciences: from Repair Replication in Bacteria to Ribosoma RNA and Retroviruses in Animals to Recombination in Zebrafish" Workshop on DNA repair and related DNA transactions, Fallen Leaf Lake, CA, Abstract, Oct. 4-7, 2001, 1 pg.

Hackett, "The Sleeping Beauty Transposon System for Non-viral Gene Delivery into Animal Cells for Long-term Expression," Biophex 2002, Santa Clara, CA, Abstract, Sep. 22-23, 2002, 1 pg.

Hackett, "The Sleeping Beauty Transposon System for Non-viral Gene Delivery into Animal Cells for Long-term Expression," Biophex 2002, San Diego, CA, Abstract, Dec. 9-10, 2002, 8 pgs.

Hackett, Perry B., "Sleeping Beauty-Mediated Gene Therapy for Hemophilia," Grant Abstract, Grant No. 2R44HL072539-02A1 [online]. National Heart, Lung and Blood Institute, project dates Feb. 1, 2003-Dec. 31, 2006 [retrieved on Feb. 13, 2006]. Retrieved from the Internet: URL:http://crips.cit.nih.gov/CRISP_LIB.getdoc?textkey=6883402&p_grant_num=2R44H . . . 2 pgs.

Hackett, Perry B., "Transposon-Mediated Gene Therapy for Fanconi Anemia," Grant Abstract, Grant No. 1R43HL076908-01 [online]. National Heart, Lung and Blood Institute, project dates Apr. 1, 2004-Mar 31, 2005 [retrieved on Feb. 13, 2006]. Retrieved from the Internet: URL:http://crisp.cit.nih.gov/CRISP_LIB.getdoc?textkey=6787819&p_grant_num=1R43H . . . 2 pgs.

Hackett et al., "Activity of the Sleeping Beauty Transposon System in Zebrafish and Other Vertebrate Cells," NIH Workshop on Genomic and Genetic Tools for the Zebrafish, NIH, Abstract, May 10-11, 1999, 1 pg.

Hackett et al., "Activity of the Sleeping Beauty Transposon System in Zebrafish and Mammalian Cells," Cold Spring Harbor Varmus Meeting, CSH Laboratory, NY, Abstract, Dec. 17-20, 1999, 1 pg.

Hackett et al., "New Genetic Engineering Methods and Goals for Improvement of Fish and Their Interactions with the Environment," World Aquaculture Symposium, Nice, France, Abstract, May 2-7, 2000, 1 pg.

Hackett et al., "Sleeping Beauty: A DNA-Based Transposon System for Gene Delivery and Gene Discovery in Vertebrates," Amer. Soc. Gene Therapy, Denver, CO, Abstract, May 31-Jun. 4, 2000, 1 pg.

Hackett et al., "Sleeping Beauty: A Transposon System for Gene Delivery in Vertebrates," Frontiers in Nephrology Symposium—Gene Therapy, Boulder Creek, CO, Abstract, Jun. 5-6, 2000, 1 pg.

Hackett et al., "New Genetic Engineering Methods for Improvement of Fish," International Marine Biotechnology Conference, Townsville, Australia, Abstract, Sep. 29-Oct. 5, 2000, 1 pg.

Hackett et al., "Applications of the Sleeping Beauty Transposon System in Fish," 3rd IUBS Symposium on Molecular Aspects of Fish Genomes and Development, Singapore, Abstract, Feb. 19-21, 2001, 1 pg.

Hackett et al., "Development of a Transposon System for Gene Delivery and Gene-tagging in Vertebrates," International Symposium for Innovative Technologies, Minneapolis, MN, Abstract, May 2000, 1 pg.

Hackett et al., "Applications of the Sleeping Beauty Transposon System in Animals,", *Dev. Grow. Diff.*;43:S27, 14th Intl. Congress of Developmental Biology, Kyoto, Japan, Abstract, Jul. 8-12, 2001, 1 pg.

Hackett et al., "Structural and Functional Studies with the Sleeping Beauty Transposon System in Vertebrate," UC Davis Transgenic Animal Research Conference III, Tahoe City, CA, Abstract, Sep. 9-12, 2001, 2 pgs.

Hackett et al., "Structure/Function Studies with the Sleeping Beauty Transposon System," 24th Annual Meeting of the Molecular Biology Society of Japan, Yokohama, Japan, Abstract, Dec. 10, 2001, 1 pg.

Hackett et al., "Development of the Sleeping Beauty Transposon System for Non-viral Gene Therapy. Angiogenesis in Cancer and Other Diseases from Genes to Function to Therapy," Keystone Symposium, Banff, Canada, Abstract, Feb. 8-13, 2002, 1 pg.

Hackett et al., "Structural and functional studies with the *Sleeping Beauty* transposon system in vertebrate," *Transgenic Research*, Abstracts of the 3rd UC Davis Transgenic Animal Research Conference, 2002;11:73-94.

Hackett et al., "Application of New Genetic Tools for Understanding Gene Function in Fish," Workshop on Fish Genetics and Development, Wuhan, China, Abstract, Jun. 1-5, 2003, 1 pg.

Hackett et al., "Applications of Transposable Elements in Fish for Transgenesis and Functional Genomics," *Fish Development and Genetics, The Zebrafish and Medaka Models*, Hackensack, NJ, 2004, vol. 2, Chap. 16:532-580.

Hackett et al., "*Sleeping Beauty* Transposon-Mediated Gene Therapy for Prolonged Expression," *Adv. Genet.*, 2005; 54:189-232.

He et al., "Insulin expression in livers of diabetic mice mediated by hydrodynamics—based administration," *World J. Gastroenterol.*, 2004;10:567-572.

Heggestad et al., "Transposon-based RNAi delivery system for generating knockdown cell lines," *Biochem. Biophys. Res. Comm.*, 2004;316:643-650.

Hermanson et al., "*Sleeping Beauty* Transposon for Efficient *Gene Delivery,*" *Methods in Cell Biology*, 2004, San Diego, CA, vol. 77:349-362.

Horie et al., "Characterization of *Sleeping Beauty* Transposition and Its Application to Genetic Screening in Mice," *Mol. Cell. Biol.*, Dec. 2003;23(24):9189-9207.

Huang et al., "Stable gene transfer and expression in human primary T cells by the *Sleeping Beauty* transposon system," *Blood*, Jan. 15, 2006; 107(2):483-491. [Epub Sep. 27, 2005, DOI 10.1182/Blood-2005-05-2133].

Ivics et al., "Transposable Elements for Transgenesis and Insertional Mutagenesis in Vertebrates: a Contemporary Review of Experimental Strategies," *Methods Mol. Biol., Mobile Genetic Elements*, Totowa, NJ, 2004, vol. 260:255-276.

Ivics et al., "The *Sleeping Beauty* Transposable Element: Evolution, Regulation and Genetic Applications," *Curr. Issues Mol. Biol.*, 2004;6:43-55.

Ivics et al., "A whole lotta jumpin goin' on: new transposon tools for vertebrate functional genomics," *Trends Genet.*, Jan. 2005; 21(1):8-11.

Izsvák et al., "Short Inverted-Repeat Transposable Elements in Teleost Fish and Implications for a Mechanism of Their Amplification" *J. Mol. Evol.*, 1999;48:13-21.

Izsvák et al., "Healing the Wounds Inflicted by *Sleeping Beauty* Transposition by Double-Strand Break Repair in Mammalian Somatic Cells," *Mol. Cell*, Jan. 30, 2004;13:279-290.

Izsvák et al., "*Sleeping Beauty* Transposition: Biology and Applications for Molecular Therapy," *Mol. Ther.*, Feb. 2004;9(2):147-156.

Izsvák et al., "*Sleeping Beauty* hits them all: transposon- mediated saturation mutagenesis in the mouse germline," *Nat. Methods*, Oct. 2005; 2(10):735-737.

Karsi et al., "Effects of Insert Size on Transposition Efficiency of the *Sleeping Beauty* Transposon in Mouse Cells," *Mar. Biotechnol.*, 2001;3:241-245.

Kaufman et al., "Remobilization of Sleeping Beauty Transposons in Zebrafish," Cold Spring Harbor Meeting on Zebrafish Genetics and Development, CSH Laboratory, NY, Abstract, Apr. 26-30, 2000, 1 pg.

Kawakami et al., "Excision of the *To12* transposable element of the medaka fish, *Oryzias latipes*, in zebrafish, *Danio rerio,*" *Gene*, 1998;225:17-22.

Kawakami et al., "A Transposon-Mediated Gene Trap Approach Identifies Developmentally Regulated Genes in Zebrafish," *Dev. Cell*, Jul. 2004; 7:133-144.

Kawakami, "Transposon Tools and Methods in Zebrafish," *Dev. Dyn.*, 2005; 234:244-254.

Keng et al., "Region-specific saturation germline mutagenesis in mice using the *Sleeping Beauty* transposon system," *Nat. Methods*, Oct. 2005; 2(10):763-769.

Kren et al., "In Utero Delivery and Long-term Expression of GFP in Liver Mediated by the Sleeping Beauty Transposon System," *Mol. Therapy*;3:S138, Amer. Soc. Gene Therapy, Seattle, WA, Abstract, May 30-Jun. 3, 2001, 1 pg.

Kren et al., "Gene Therapy as an Alternative to Liver Transplantation," *Liver Transpl.*, Dec. 2002;8(12):1089-1108.

Kren et al., "Hepatocyte-targeted delivery of *Sleeping Beauty* mediates efficent gene transfer *in vivo,*" *Gene Ther. Mol. Biol.*, Nov. 2003;7:229-238.

Largaespada, "Generating and manipulating transgenic animals using transposable elements," *Reprod. Biol. Endocrinol.*, Nov. 7, 2003; 1(80):1-10.

Larson et al., "Expression of *VE-cadherin* in Zebrafish Embryos: A New Tool to Evaluate Vascular Development," *Dev. Dyn.*, 2004; 231:204-213.

Liu et al., "In Vivo Transposition Assay of Sleeping Beauty Transposon in Zebrafish," Cold Spring Harbor Meeting on Zebrafish Genetics and Development, CSH Laboratory, NY, Abstract, Apr. 26-30, 2000, 1 pg.

Liu et al., "Improved Sleeping Beauty Transposon System for Use in Gene Therapy," *Mol. therapy*;5:S333, Amer. Soc. Gene Therapy, Boston, MA, Abstract, Jun. 5-9, 2002, 1 pg.

Liu et al., "Improvements in the Sleeping Beauty Transposon System for Use in Gene Transfer," International Zebrafish Meeting, Madison, WI, Abstract, Jun. 12-16, 2002, 1 pg.

Liu et al., "Endothelial Targeting of the *Sleeping Beauty* Transposon within Lung," *Mol. Ther.*, Jul. 2004;10(1):97-105.

Liu et al., "Excision of *Sleeping Beauty* transposons: parameters and applications to gene therapy," *J. Gene Med.*, 2004;6:574-583.

Liu et al., "Target-site Preferences of *Sleeping Beauty* Transposons," *J. Mol. Biol.*, 2005; 346:161-173.

Masuda et al., "Transposon-independent increase of transcription by the Sleeping Beauty transposase," *Biochem. Biophys. Res. Comm.*, 2004;317:796-800.

Mikkelsen et al., "Helper-Independent *Sleeping Beauty* Transposon-Transposase Vectors for Efficient Nonviral Gene Delivery and Persistent Gene Expression *in Vivo,*" *Mol. Therapy*, Oct. 2003;8(4):654-665.

Miskey et al., "*The Frog Prince*: a reconstructed transposon from *Rana pipiens* with high transpositional activity in vertebrate cells," *Nucl. Acids Res.*, 2003;31(23):6873-6881.

Miskey et al., "DNA transposons in vertebrate functional genomics," *Cell Mol. Life Sci.*, 2005; 62:629-641.

Montini et al., "*In Vivo* Correction of Murine Tyrosinemia Type I by DNA-Mediated Transposition," *Mol. Therapy*, Dec. 2002;6(6):759-769.

"Mouse Transposon Insertion Database" [online]. University of Minnesota, Database Access [retrieved on Dec. 20, 2004]. Retrieved from the Internet:<URL:http://mouse.ccgb.umn.edu/ transposon/>; 1 pg.

Ohlfest et al., "Integration and Long-Term Expression in Xenografted Human Glioblastoma Cells Using a Plasmid-Based Transposon System," *Mol. Therapy*, Aug. 2004;10(2):260-268.

Ohlfest et al., "Phenotypic correction and long-term expression of factor VIII in hemophilic mice by immunotolerization and nonviral gene transfer using the *Sleeping Beauty* transposon system," *Blood*, Apr. 1, 2005; 105(7):2691-2698.

Ohlfest et al., "Combinatorial Antiangiogenic Gene Therapy by Nonviral Gene Transfer Using the *Sleeping Beauty* Transposon Causes Tumor Regression and Improves Survival in Mice Bearing Intracranial Human Glioblastoma," *Mol. Ther.*, Nov. 2005; 12(5):778-788. [Epub doi:10.1016/j.ymthe.2005.07.689, Sep. 16, 2005].

Ortiz-Urda et al., "Sustaninable correction of junctional epidermolysis bullosa via transposon-mediated nonviral gene transfer," *Gene Therapy*, 2003;10:1099-1104.

Park et al., "DNA methyllation of Sleeping Beauty with Transposition into the mouse genome," *Genes to Cells*, 2005; 10:763-776.

Richardson et al., "Strategies for Hepatic Gene Correction," *J. Drug Target*, 2002;10(2): 133-141.

Roberg-Perez et al., "MTID: a database of *Sleeping Beauty* transposon insertions in mice," *Nucl. Acids Res.*, 2003;31(1):78-81.

Rumpold et al., "RNAi-mediated knockdown of P-glycoprotein using a transposon-based vector system durably restores imatinib sensitivity in imatinib-resistant CML cell lines," *Exp. Hematol.*, 2005; 33:767-775.

Score et al., "*Sleeping Beauty*-Mediated Transposition and Long-Term Expression *in Vivo*: Use of the LoxP/Cre Recombinase System to Distinguish Transposition-Specific Expression," *Mol. Ther.* [Epub doi:10.1016/j.ymthe.2005.10.015].

Starr et al., "Cancer Gene Discovery Using the Sleeping Beauty Transposon," *Cell Cycle*, 4(12):e1-e5. [Epub Dec. 2005].

Tada et al., "Long-Term Reduction of Serum Bilirubin Levels in Gunn Rats by Retroviral Gene Transfer In Vivo," *Liver Transpl. Surg.*, Jan. 1998; 4(1):78-88.

Tolar et al., "Real-Time *In Vivo* Imaging of Stem Cells Following Transgenesis by Transposition," *Mol. Ther.*, Jul. 2005; 12(1):42-48.

Vigdal et al., "Common Physical Properties of DNA Affecting Target Site Selection of *Sleeping Beauty* and other Tc1/*mariner* Transposable Elements," *J. Mol. Biol.*, 2002;323(3):441-452.

Wacnik et al., "Tumor-induced mechanical hyperalgesia involves CGRP receptors and altered innervation and vascularization of DsRed2 fluorescent hindpaw tumors," *Pain*, 2005; 115(1-2):95-106.

Wadman et al., "Fishing for Answers with Transposons," *Mar. Biotechnol.*, May-Jun. 2005; 7:135-141.

Weiser et al., "Sleeping Beauty awakens," *Nature*, Jul. 14, 2005; 436(7048):184-186.

Whitley, Chester B., "Gene Therapy for Metabolic Disorders," Grant Abstract, Grant No. 2P01HD032652-09A1 [online]. National Institute of Child Health and Human Development, project dates Jan. 1, 1997-Dec. 31, 2008 [retrieved on Feb. 13, 2006]. Retrieved from the Internet: URL:http://crisp.cit.nih.gov/CRISP_LIB.getdoc?textkey=6708516 &p_grant_num=2P01H . . . 2 pgs.

Wilber et al., "RNA as a Source of Transposase for *Sleeping Beauty*-Mediated Gene Insertion and Expression in Somatic Cells and Tissues," *Mol. Ther.*, Dec. 12, 2005, [Epub ahead of print; doi:10.1016/j.ymthe.2005.10.015]:1-6.

Wilber et al., "Dynamic Gene Expression After Systemic Delivery of Plasmid DNA as Determined by *In Vivo* Bioluminescence Imaging," *Hum. Gene Ther.*, Nov. 2005; 16:1325-1332. [Epub Sep. 26, 2005].

Wilson et al., "Functional zinc finger/*sleeping beauty* transposase chimeras exhibit attenuated overproduction inhibition," *FEBS Lett.*, Nov. 7, 2005; 579(27):6205-6209. [Epub Oct. 17, 2005].

Wu et al., "Integration target site selection for retroviruses and transposable elements," *Cell Mol. Life Sci.*, 2004; 61:2588-2596.

Yant et al., "Nonhomologous-End-Joining Factors Regulate DNA Repair Fidelity during *Sleeping Beauty* Element Transposition in Mammalian Cells," *Mol. Cell. Biol.*, Dec. 2003;23(23):8505-8518.

Yant et al., "Mutational Analysis of the N-Terminal DNA-Binding Domain of Sleeping Beauty Transposase: Critical Residues for DNA Binding and Hyperactivity in Mammalian Cells," *Mol. Cell Biol.*, Oct. 2004;24(20):9239-9247.

Yant et al., "High-Resolution Genome-Wide Mapping of Transposon Integration in Mammals," *Mol. Cell. Biol.*, Mar. 2005; 25(6):2085-2094.

York, "Sleeping beauty offers new method to find cancer genes," *Lancet Oncol.*, Aug. 2005; 6(8):545.

Yusa et al., "Enhancement of *Sleeping Beauty* Transposition by CpG Methylation: Possible Role of Heterochromatin Formation," *Mol. Cell Biol.*, May 2004;24(9):4004-4018.

Zanta et al., "*In Vitro* Gene Delivery to Hepatocytes with Galactosylated Polyethylenimine," *Bioconjuage Chem.*, 1997; 8:839-844.

Zayed et al., "The DNA-bending protein HMGB1 is a cellular cofactor of *Sleeping Beauty* transposition," *Nucl. Acids Res.*, 2003;31(9):2313-2322.

Zayed et al., "Development of Hyperactive *Sleeping Beauty* Transposon Vectors by Mutational Analysis," *Mol. Ther.*, Feb. 2004; 9(2):292-304.

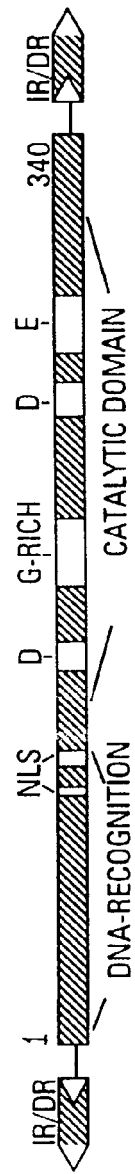
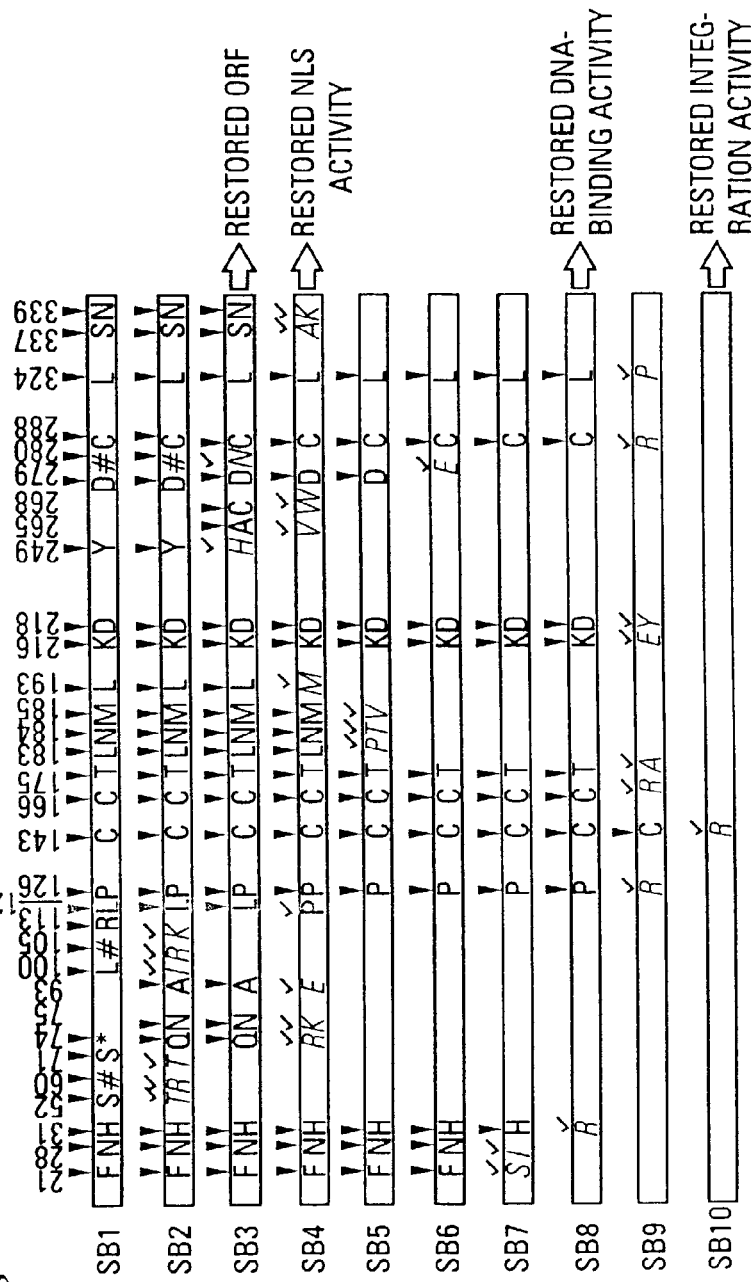
Fig. 1A
Fig. 1B

Fig. 2a (SEQ IDNO:3)

```
   1 ATGGGAAAA TCAAAAGAAA TCAGCCAAGA CCTCAGAAAA
     TACCCTTTT AGTTTTCTTT AGTCGGTTCT GGAGTCTTTT
  51 AAAATTGTAG ACCTCCACAA GTCTGGTTCA TCCTTGGGAG CAATTTCCAA
     TTTTAACATC TGGAGGTGTT CAGACCAAGT AGGAACCCTC GTTAAAGGTT
 101 ACGCCTGAAA GTACCACGTT CATCTGTACA AACAATAGTA CGCAAGTATA
     TGCGGACTTT CATGGTGCAA GTAGACATGT TTGTTATCAT GCGTTCATAT
 151 AACACCATGG GACCACGCAG CCGTCATACC GCTCAGGAAG GAGACGCGTT
     TTGTGGTACC CTGGTGCGTC GGCAGTATGG CGAGTCCTTC CTCTGCGCAA
 201 CTGTCTCCTA GAGATGAACG TACTTTGGTG CGAAAAGTGC AAATCAATCC
     GACAGAGGAT CTCTACTTGC ATGAAACCAC GCTTTTCACG TTTAGTTAGG
 251 CAGAACAACA GCAAAGGACC TTGTGAAGAT GCTGGAGGAA ACAGGTACAA
     GTCTTGTTGT CGTTTCCTGG AACACTTCTA CGACCTCCTT TGTCCATGTT
 301 AAGTATCTAT ATCCACAGTA AAACGAGTCC TATATCGACA TAACCTGAAA
     TTCATAGATA TAGGTGTCAT TTTGCTCAGG ATATAGCTGT ATTGGACTTT
 351 GGCCGCTCAG CAAGGAAGAA GCCACTGCTC CAAAACCGAC ATAAGAAAGC
     CCGGCGAGTC GTTCCTTCTT CGGTGACGAG GTTTTGGCTG TATTCTTTCG
 401 CAGACTACGG TTTGCAACTG CACATGGGGA CAAAGATCGT ACTTTTTGGA
     GTCTGATGCC AAACGTTGAC GTGTACCCCT GTTTCTAGCA TGAAAAACCT
 451 GAAATGTCCT CTGGTCTGAT GAAACAAAAA TAGAACTGTT TGGCCATAAT
     CTTTACAGGA GACCAGACTA CTTTGTTTTT ATCTTGACAA ACCGGTATTA
 501 GACCATCGTT ATGTTTGGAG GAAGAAGGGG GAGGCTTGCA ACCCGAAGAA
     CTGGTAGCAA TACAAACCTC CTTCTTCCCC CTCCGAACGT TCGGCTTCTT
 551 CACCATCCCA ACCGTGAAGC ACGGGGGTGG CAGCATCATG TTGTGGGGGT
     GTGGTAGGGT TGGCACTTCG TGCCCCCACC GTCGTAGTAC AACACCCCCA
 601 GCTTTGCTGC AGGAGGGACT GGTGCACTTC ACAAAATAGA TGGCATCATG
     CGAAACGACG TCCTCCCTGA CCACGTGAAG TGTTTTATCT ACCGTAGTAC
 651 AGGAAGGAAA ATTATGTGGA TATATTGAAG CAACATCTCA AGACATCAGT
     TCCTTCCTTT TAATACACCT ATATAACTTC GTTGTAGAGT TCTGTAGTCA
 701 CAGGAAGTYA AAGCTTGGTC GCAAATGGGT CTTCCAAATG GACAATGACC
     GTCCTTCAAT TTCGAACCAG CGTTTACCCA GAAGGTTTAC CTGTTACTGG
 751 CCAAGCATAC TTCCAAAGTT GTGGCAAAAT GGCTTAACCA CAACAAAGTC
     GGTTCGTATG AAGGTTTCAA CACCGTTTTA CCGAATTCCT GTTGTTTCAG
 801 AAGGTATTGG AGTGGCCATC ACAAAGCCCT GACCTCAATC CTATAGAAAA
     TTCCATAACC TCACCGGTAG TGTTTCGGGA CTGGAGTTAG GATATCTTTT
 851 TTTGTGGGCA GAACTGAAAA AGCGTGTGCG AGCAAGGAGG CCTACAAACC
     AAACACCCGT CTTGACTTTT TCGCACACGC TCGTTCCTCC GGATGTTTGG
 901 TGACTCAGTT ACACCAGCTC TGTCAGGAGG AATGGGCCAA AATTCACCCA
     ACTGAGTCAA TGTGGTCGAG ACAGTCCTCC TTACCCGGTT TTAAGTGGGT
 951 ACTTATTGTG GGAAGCTTGT GGAAGGCTAC CCGAAACGTT TGACCDAAGT
     TGAATAACAC CCTTCGAACA CCTTCCGATG GGCTTTGCAA ACTGGGTTCA
1001 TAAACAATTT AAAGGCAATG CTACCAAATA CTAG
     ATTTGTTAAA TTTCCGTTAC GATGGTTTAT GATC
```

Fig.2b

PAIRED-LIKE DOMAIN WITH LEUCINE-ZIPPER

```
  1  MGKSKEISQD LRKKIVDLHK SGSSLGAISK RLKVPRSSVQ TIVRKYKHHG

51  TTQPSYRSGR RVLSPRDER TLVRKVQINP RTTAKDLVKM LEETGTKVSI
                    NLS
101  STVKRVLYRH NLKGRSARKK PLLQNRHHKA RLRFATAHGD KDRTFWRNVL

151  WSDETKIELF GHNDHRYVWR KKGEACKPKN TIPTVKHGGG SIMLWGCFAA
                                       GLYCINE-RICH BOX
201  GGTGALHKID GIMRKENYVD ILKQHLKTSV RKLKLGRKWV FQMDNDPKHT

251  SKVVAKWLKD NKVKVLEWPS QSPDLNPIEN LWAELKKRVR ARRPTNLTQL
                              DD(34)E BOX
301  HQLCQEEWAK IHPTYCGKLV EGYPKRLTQV KQFKGNATKY *(SEQ ID NO:1)
```

GTTGAAGTCGGAAGTTTACATACACTTAGG (SEQ ID NO:37) -SALMONID-
GTTAAACCAGAAGTTTACACACACTGTAT (SEQ ID NO:38) -ZEBRAFISH-

CCAGTGGGTCAGAAGTTTACATACACTTAAG (SEQ ID NO:39)
CTTGAAAGTC..AAGTTTACATACACAATAAG (SEQ ID NO:40)

EXTERNAL TACAGTTGAAGTCGGAAGTTTACATACACTTAGG (SEQ ID NO:41)
INTERNAL TCCAGTGG..GTCAGAAGTTTACATACACTAAGT (SEQ ID NO:42)

GENERATE SEQUENCE-TAGGED SITES (STS)
BY ISOLATION OF FRAGMENTS a AND d AND
PLACE THEM ON A GENETIC MAP

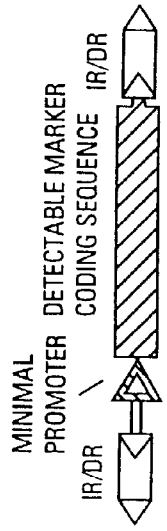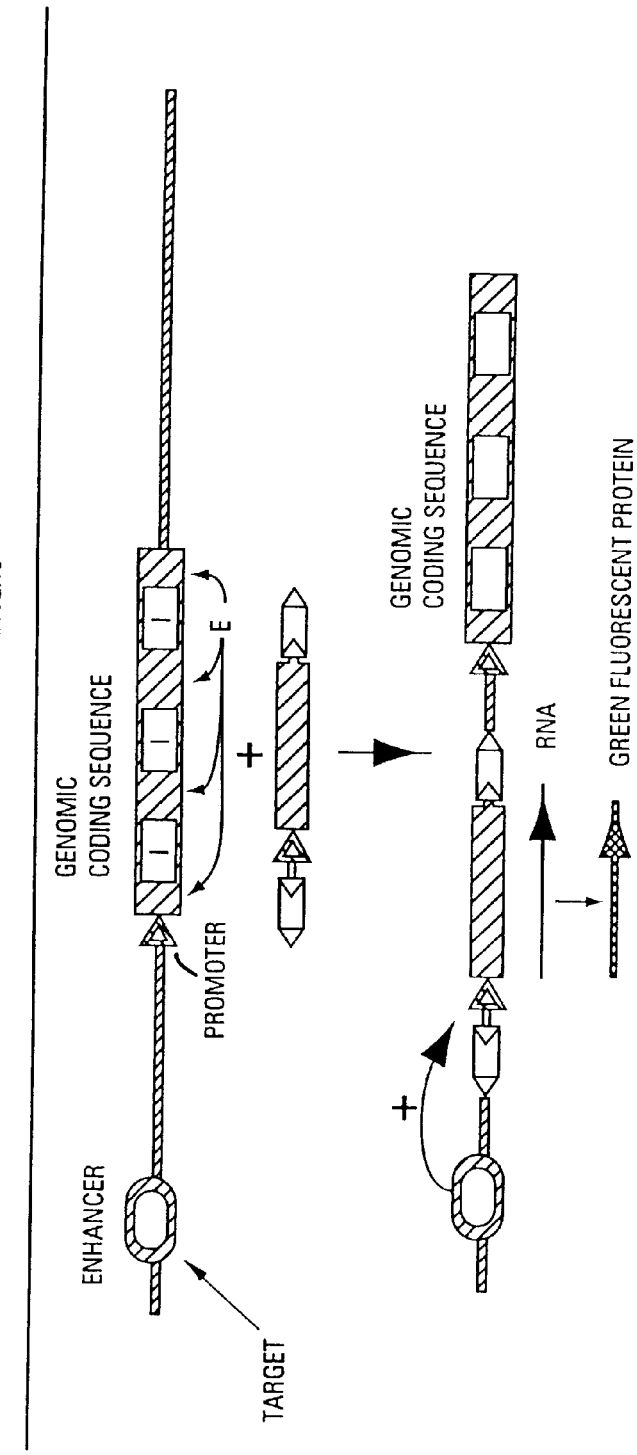
Fig. 11

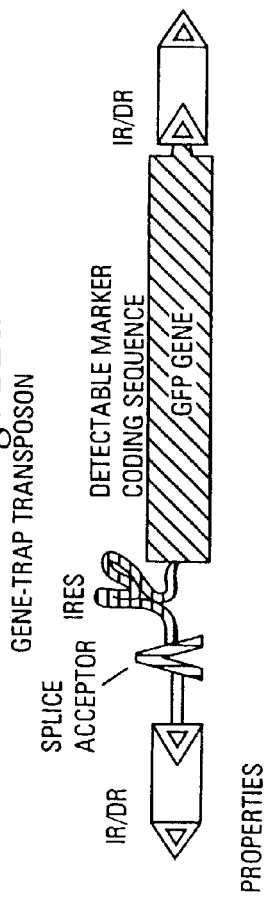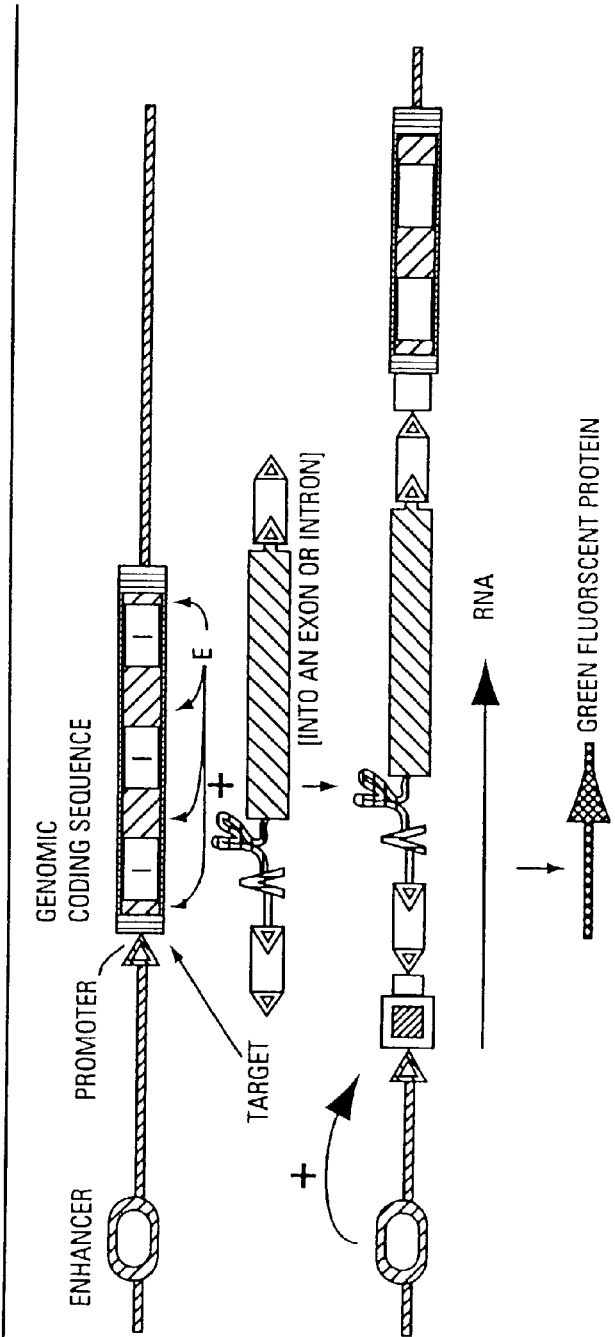
Fig. 12a

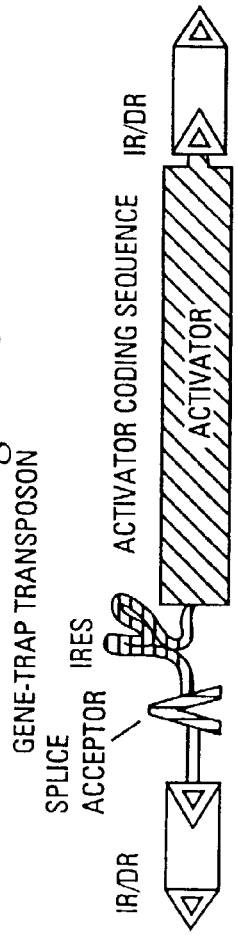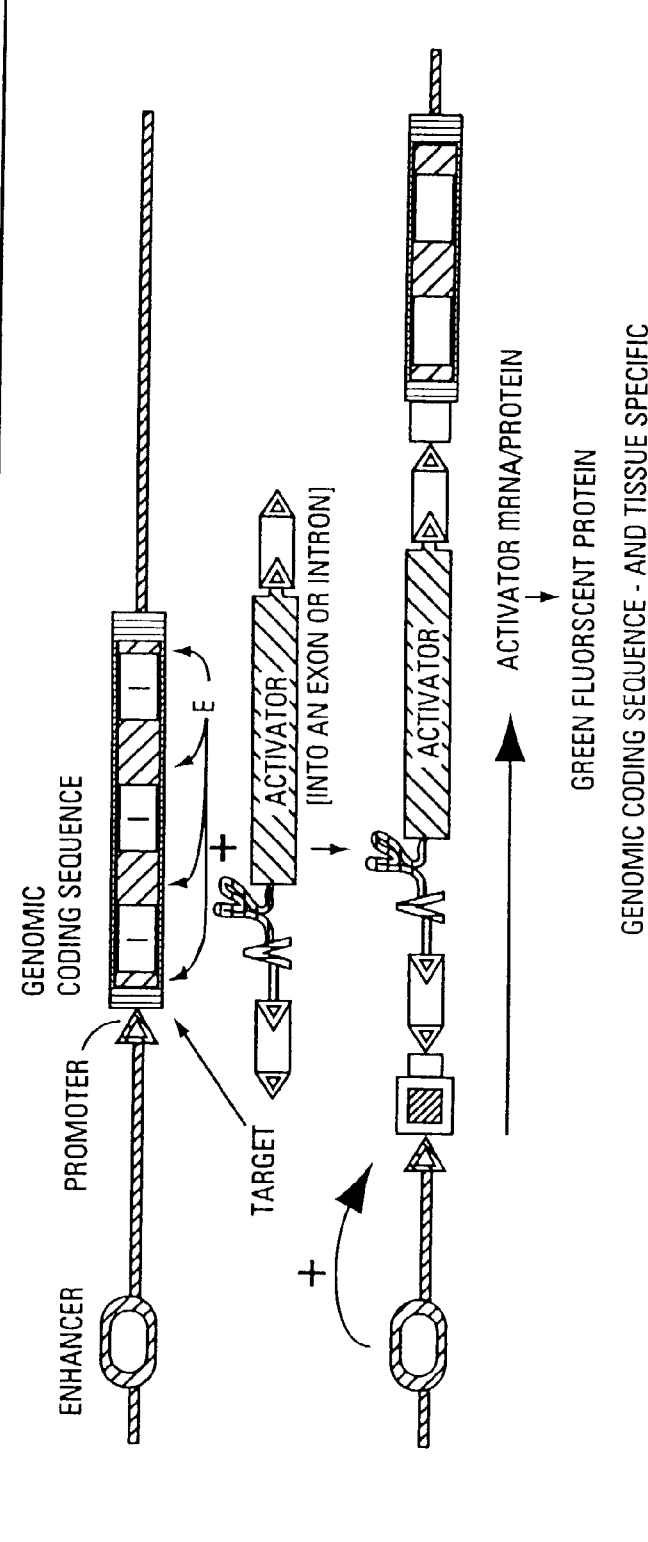
Fig. 12b

DICISTRONIC VECTORS FOR MARKING SITES OF EXPRESSION

SITES OF GFP EXPRESSION MARK CELLS THAT ARE ALSO EXPRESSING GENE X

Fig. 16
INVERSE PCR STRATEGY
TO LOCATE AND AMPLIFY FLANKING GENOMIC SEQUENCE
1. 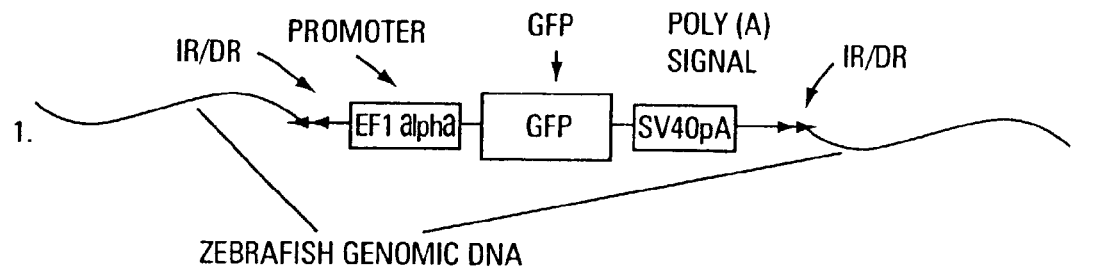
2. 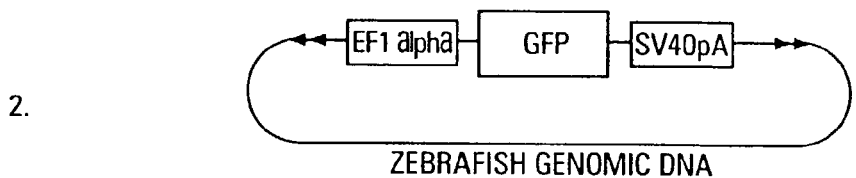
3. 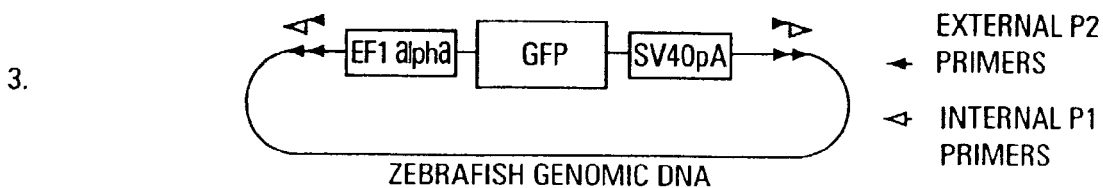
   EXTERNAL P2 PRIMERS
   INTERNAL P1 PRIMERS
4. 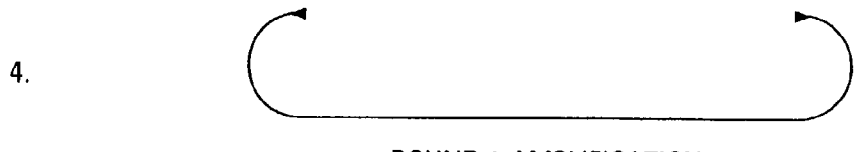
   ROUND 1 AMPLIFICATION
   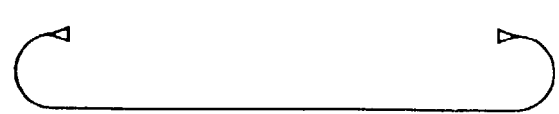
   ROUND 2 AMPLIFICATION

NUCLEIC ACID TRANSFER VECTOR FOR THE INTRODUCTION OF NUCLEIC ACID INTO THE DNA OF A CELL

CONTINUING APPLICATION DATA

This application is a continuation application of U.S. Ser. No. 09/191,572 filed Nov. 13, 1998 now abandoned, which is incorporated by reference in its entirety.

STATEMENT OF GOVERNMENT RIGHTS

The present invention was made with government support under Grant No. 2ROI-RR06625-05, awarded by the National Institutes of Health/National Institutes of Research Resources. The Government may have certain rights in this invention.

FIELD OF THE INVENTION

This invention relates to methods for functional genomics including identifying expression control sequences, coding sequences and the function of coding sequences in the genomic DNA of a cell. The invention also relates to transposons and transposases.

BACKGROUND OF THE INVENTION

Transposons

Transposons or transposable elements include a short piece of nucleic acid bounded by inverted repeat sequences. Active transposons encode enzymes that facilitate the insertion of the nucleic acid into DNA sequences.

In vertebrates, the discovery of DNA-transposons, mobile elements that move via a DNA intermediate, is relatively recent (Radice, A. D., et al., 1994. *Mol. Gen. Genet.* 244, 606–612). Before then, only inactive, highly mutated members of the Tc1/mariner as well as the hAT (hobo/Ac/Tam) superfamilies of eukaryotic transposons had been isolated from different fish species, *Xenopus* and human genomes (Oosumi et al., 1995. *Nature* 378, 873; Ivics et al. 1995. *Mol. Gen. Genet.* 247, 312–322; Koga et al., 1996. *Nature* 383, 30; Lam et al., 1996. *J. Mol. Biol.* 257, 359–366 and Lam, W. L., et al. *Proc. Natl. Acad. Sci. USA* 93, 10870–10875).

DNA transposable elements transpose through a cut-and-paste mechanism; the element-encoded transposase catalyzes the excision of the transposon from its original location and promotes its reintegration elsewhere in the genome (Plasterk, 1996 *Curr. Top. Microbiol. Immunol.* 204, 125–143). Autonomous members of a transposon family can express an active transposase, the trans-acting factor for transposition, and thus are capable of transposing on their own. Nonautonomous elements have mutated transposase genes but may retain cis-acting DNA sequences. These cis-acting DNA sequences are also referred to as inverted terminal repeats. Some inverted repeat sequences include one or more direct repeat sequences. These sequences usually are embedded in the terminal inverted repeats (IRs) of the elements, which are required for mobilization in the presence of a complementary transposase from another element or from itself.

Not a single autonomous transposable element has been isolated from vertebrates; all transposon-like sequences isolated to date are defective, apparently as a result of a process called "vertical inactivation" (Lohe et al., 1995 *Mol. Biol. Evol.* 12, 62–72). According to one phylogenetic model (Hartl et al., 1997 *Trends Genet.* 13, 197–201), the ratio of nonautonomous to autonomous elements in eukaryotic genomes increases as a result of the trans-complementary nature of transposition. This process leads to a state where the ultimate disappearance of active, transposase-producing copies in a genome can be inevitable. Consequently, DNA-transposons can be viewed as transitory components of genomes which, in order to avoid extinction, must find ways to establish themselves in a new host. Indeed, horizontal gene transmission between species is thought to be one of the important processes in the evolution of transposons (Lohe et al., 1995 *Mol. Biol. Evol.* 12, 62–72 and Kidwell, 1992. *Curr. Opin. Genet. Dev.* 2, 868–873).

The natural process of horizontal gene transfer can be mimicked under laboratory conditions. In plants, transposable elements of the Ac/Ds and Spm families have been routinely introduced into heterologous species (Osborne and Baker, 1995 *Curr. Opin. Cell Biol.* 7, 406–413). In animals, however, a major obstacle to the transfer of an active transposon system from one species to another has been that of apparent species-specificity of transposition due to the requirement for factors produced by the natural host. For this reason, attempts have been unsuccessful to use the P element transposon of *Drosophila melanogaster* for genetic transformation of non-drosophilid insects, zebrafish and mammalian cells (Gibbs et al., 1994 *Mol. Mar. Biol. Biotech.* 3, 317–326; Handler et al., 1993. *Arch. Insect Biochem. Physiol.* 22, 373–384; and Rio et al., 1988 *J. Mol. Biol.* 200, 411–415). In contrast to P elements, members of the Tc1/mariner superfamily of transposable elements may not be as demanding for species-specific factors for their transposition. These elements are widespread in nature, ranging from single-cellular organisms to humans (Plasterk, 1996 *Curr. Top. Microbiol. Immunol.* 204, 125–143). In addition, recombinant Tc1 and mariner transposases expressed in *E. coli* are sufficient to catalyze transposition in vitro (Vos et al, 1996 *Genes. Dev.* 10, 755–761 and Lampe et al., 1996. *EMBO J.* 15, 5470–5479 and PCT International Publication No. WO 97/29202 to Plasterk et al.). Furthermore, gene vectors based on Minos, a Tc1-like element (TcE) endogenous to *Drosophila hydei*, were successfully used for germline transformation of the fly *Ceratitis capitata* (Loukeris et al., 1995 *Science* 270, 2002–2005).

Molecular phylogenetic analyses have shown that the majority of the fish TcEs can be classified into three major types: zebrafish-, salmonid- and *Xenopus* TXr-type elements, of which the salmonid subfamily is probably the youngest and thus most recently active (Ivics et al., 1996, *Proc. Natl. Acad. Sci. USA* 93, 5008–5013). In addition, examination of the phylogeny of salmonid TcEs and that of their host species provides important clues about the ability of this particular subfamily of elements to invade and establish permanent residences in naive genomes through horizontal transfer, even over relatively large evolutionary distances.

TcEs from teleost fish (Goodier and Davidson, 1994 *J. Mol. Biol.* 241, 26–34), including Tdr1 in zebrafish (Izsvak et al., 1995 *Mol. Gen. Genet.* 247, 312–322) and other closely related TcEs from nine additional fish species (Ivics et al., 1996. *Proc. Natl. Acad. Sci. USA* 93, 5008–5013) are by far the best characterized of all the DNA-transposons known in vertebrates. Fish elements, and other TcEs in general, are typified by a single defective gene encoding a transposase enzyme flanked by inverted repeat sequences. Unfortunately, all the fish elements isolated so far are inactive due to one or more mutations in the transposase genes.

Functional Genomics

There are estimated to be between 50,000 and 100,000 genes in the genome of vertebrates. The expression of these genes is carefully orchestrated such that most genes are not expressed most of the time in most tissues. The roles of most genes in vertebrate genomes are unknown. Yet, most diseases have a genetic basis. Accordingly, finding the sites and roles of expression of the genes in a vertebrate, especially human, genome is an important task. The task is exceedingly difficult.

Most studies to date in the field of genomics have concentrated on identifying in cells of various types the sequences of expressed mRNAs encoded by the coding sequence of a gene. However, this procedure does not often provide insights into the functions of the genes, nor their importance.

An alternative method of finding genes and their functions is to interrupt (mutate) genes with a molecular tag. Then, the interrupted genetic locus can be isolated based on the inserted genetic tag and the gene can be correlated with a phenotype, i.e., a physical result due to the loss of function of the interrupted gene. Genetic tags called gene-traps have been devised wherein a marker gene is inserted randomly into a genome (reviewed in Mountford, P. S., et al. *Trends Genet.*, 11, 179–84 (1995)). When a critical gene is interrupted, and the marker gene is inserted in just the right way (in the correct direction, in-frame, and in an exon of the interrupted gene), the marker gene is expressed in the tissue in which the interrupted gene normally is expressed.

A variation of the gene trap is to employ a splice acceptor site followed by an internal ribosome entry site (IRES) placed in front of a marker gene. Splice acceptor sites provide signals to target the sequences following the splice acceptor site to be expressed as mRNA provided there is an intron upstream of the splice acceptor site (Padgett, T., et al., *Ann. Rev. Biochem. J.*, 55, 1119–1150 (1988)). An IRES allows ribosomal access to mRNA without a requirement for cap recognition and subsequent scanning to the initiator AUG (Pelletier, J. A., et al., *Nature*, 334, 320–325 (1988)). This expands the probability that the marker gene will be expressed when inserted into a gene. With a construct containing a splice acceptor site followed by an IRES is placed in front of a marker gene, it is possible to get expression of the marker gene even if the construct integrates in an intron or if it integrates out of frame with respect to the interrupted gene. The splice acceptor increases the likelihood that the inserted sequences will be present in the resulting mRNA, and the IRES increases the likelihood of translation of the inserted sequences. This approach, known to the art as a "gene-trap," requires that the molecular tag insert within the coding sequence where it will be expressed at approximately the same levels as the gene that is disrupted. However, the level of expression of the disrupted gene may be low and the "target-size" (the length of the coding sequence in base-pairs) may be small.

The encephalomycarditis virus (EMCV) IRES has been used for gene-trapping (von Melchner et al., *J. Virol.*, 63, 3227–3233 (1989)), is well characterized (Jang, S. K., et al., *Genes Dev* 4, 1560–1572 (1990); Kaminski, A., et al., *EMBO J* 13, 1673–1681 (1994); Hellen, C. U., et al., *Curr. Top. Microbiol. Immunol.* 203, 31–63 (1995)) and has been shown to function efficiently in mammalian (Borman, A. M., et al., *Nucleic Acids Res.* 25, 925–32 (1997), Borman, A. M., et al., *Nucleic Acids Res.* 23, 3656–63 (1995)) and chicken cells (Ghattas, I. R., et al., *Mol. Cell. Biol.* 11, 5848–59 (1991)). The use of an IRES between the splice acceptor and reporter molecule has been shown to lead to as much as 10-fold greater numbers of G418-resistant colonies in mouse embryonic stem cells than a non-IRES vector (see Mountford P. S., et al. *Trends Genet.*, 11, 179–84 (1995)). But this rate is still unacceptably low, which is why it is not used for mass screening of genes.

IRESs have been adapted into dicistronic vectors for the expression of two open reading frames. For instance, using an IRES in a dicistronic vector can result in more than 90% of transfected cells producing both the biological gene of interest and the selectable marker (Ghattas et al. *Mol. Cell. Biol.*, 11, 5848–59 (1991)).

Another strategy results in the "trapping" of sequences 3' of the inserted marker gene. This entails the use of a retrovirus to deliver a marker gene that is placed between a promoter and a splice donor site (Zambrowicz, B. P., et al., *Nature*, 392, 608–611 (1998)). Splice donor sites provide signals to target the RNA sequences encoding the marker gene to be spliced to the next downstream splice acceptor site. When the marker gene is expressed, and there is a downstream splice acceptor site, the mRNA may contain a poly(A) tail and therefore be more stable and more efficiently translated. This expands the probability that the marker gene will be expressed only when inserted into a gene.

An alternative strategy is to use an enhancer-trap (Weber, F., et al., *Cell*, 36, 983–992 (1984)). In this strategy, the marker gene is placed behind a weak promoter to give a minimal promoter-marker gene construct. The minimal promoter by itself does not have the ability to direct high expression of the marker gene. However, when the minimal promoter is located in the vicinity of certain regulatory sequences called enhancers, it can direct the expression of the marker gene at levels and in tissues in which the enhancers are active. Thus, the enhancer-trap tag does not have to insert only within a coding sequence; it can be activated by insertion outside of the transcription unit. An enhancer-trap may direct higher levels of expression than a gene-trap vector, which may increase the ability of a researcher to detect the insertion of the molecular tag.

Many methods for introducing DNA into a cell in order to perform various types of mutational analysis such as described above are known. These include, but are not limited to, DNA condensing reagents such as calcium phosphate, polyethylene glycol, and the like, lipid-containing reagents, such as liposomes, multi-lamellar vesicles, and the like, virus-mediated strategies, ballistic methods and microinjection and the like. These methods all have their limitations. For example, there are size constraints associated with DNA condensing reagents and virus-mediated strategies. Further, the amount of nucleic acid that can be introduced into a cell is limited in virus strategies. Not all methods facilitate integration of the delivered nucleic acid into cellular nucleic acid and while DNA condensing methods and lipid-containing reagents are relatively easy to prepare, the incorporation of nucleic acid into viral vectors can be labor intensive. Moreover, virus-mediated strategies can be cell-type or tissue-type specific and the use of virus-mediated strategies can create immunologic problems when used in vivo. Most non-viral mediated methods often result in concatamerization of input DNA as well as random break points within the delivered DNA. Consequently, currently available vectors are limited in the ability to insert either gene-traps or enhancer-traps into genomes at high rates for high throughput screening for mutations and associated identification of tissues in which the marker gene is expressed. Thus, there remains a need for new methods for introducing into a cell constructs that contain molecular tags that can provide information regarding sites and roles of expression of genes.

SUMMARY OF THE INVENTION

The present invention is directed to novel transposon-derived vectors and methods of using them for insertional mutagenesis. A nucleic acid fragment is provided that includes a nucleic acid positioned between at least two inverted repeats wherein the inverted repeats can bind to a transposase, preferably an SB protein. The nucleic acid sequence includes a coding sequence. In some embodiments of the invention the coding sequence is a detectable marker coding sequence that encodes a detectable marker or a selectable marker, such as green fluorescent protein, luciferase or neomycin. The nucleic acid sequence optionally includes at least one of (i) a weak promoter, for instance a carp β-actin promoter, (ii) a splice acceptor site and (iii) an internal ribosome entry site, each of which is operably linked to the detectable marker coding sequence. Alternatively, the nucleic acid sequence can include an analyte coding sequence located 5' of the detectable marker coding sequence and an internal ribosome entry site located therebetween, the internal ribosome entry site being operably linked to the detectable marker coding sequence. In some embodiments the analyte coding sequence is operably linked to a promoter.

The present invention further provides a method for identifying an expression control region, such as an enhancer, in a cell. A nucleic acid fragment of the invention containing a nucleic acid sequence that includes a detectable marker coding sequence is introduced into a cell, together with a source of transposase. The detectable marker coding sequence is operably linked to a weak promoter, and the nucleic acid sequence is positioned between at least two inverted repeats, wherein the inverted repeats can bind to transposase. The detectable marker or the selectable marker is then detected in the cell or its progeny containing the nucleic acid fragment, wherein the expression of the detectable marker or the selectable marker indicates that the nucleic acid fragment has integrated into the DNA of the cell or its progeny within a domain that contains an enhancer. The transformed cell or its progeny can be evaluated for any changes in phenotype resulting from the insertion. In order to determine the location in the cell DNA into which the nucleic acid fragment has inserted, the DNA of the cell can be cleaved with a restriction endonuclease to yield one or more restriction fragments that contain at least a portion of the inverted repeat and genomic DNA of the cell that is adjacent to the inverted repeat. The restriction fragment can be sequenced to determine the nucleotide sequence of the adjacent genomic DNA, and this sequence can then be compared with sequence information in a computer database.

Also provided by the invention is a method for identifying a genomic coding sequence in a cell. A nucleic acid fragment of the invention containing a detectable marker coding sequence, a splice acceptor site and an internal ribosome entry site is introduced into along with a source of transposase. The splice acceptor site and internal ribosome entry site are each operably linked to the detectable marker coding sequence, and the nucleic acid sequence is positioned between at least two inverted repeats wherein the inverted repeats can bind to the transposase. The detectable marker or the selectable marker is detected in the cell or its progeny containing the nucleic acid fragment, wherein expression of the detectable marker or the selectable marker indicates that the nucleic acid fragment has integrated within a genomic coding sequence of the cell or its progeny. The detectable marker or the selectable marker can be expressed spatially and temporally in the same way as the genomic coding sequence is expressed when not interrupted. The cell or its progeny can be evaluated for any change in phenotype resulting from the insertion. The DNA of the cell can be cleaved with a restriction endonuclease and the resulting restriction fragments sequenced in order to determine the location in the cell DNA into which the nucleic acid fragment has inserted.

Another aspect of the invention provides a method for identifying the function of an analyte coding sequence. A nucleic acid fragment containing a detectable marker coding sequence, an analyte coding sequence located 5' of the detectable marker coding sequence, and an internal ribosome entry site located therebetween is introduced into a cell along with a source of transposase. The internal ribosome entry site is operably linked to the detectable marker coding sequence, and the nucleic acid fragment is positioned between at least two inverted repeats that can bind to a transposase. The detectable marker or the selectable marker is detected in the cell or its progeny containing the nucleic acid fragment, wherein the expression of the detectable marker or the selectable marker indicates that the nucleic acid fragment has integrated into the DNA of the cell and that the analyte coding sequence is expressed. The cell or its progeny can be evaluated for any change in phenotype resulting from the insertion, wherein an altered phenotype indicates that the analyte coding sequence plays a function in the phenotype. The DNA of the cell can be cleaved with a restriction endonuclease and the resulting restriction fragments sequenced in order to determine the location in the cell DNA into which the nucleic acid fragment has inserted The invention also provides a gene transfer system to introduce a nucleic acid sequence into the DNA of a cell. The system includes a nucleic acid fragment and a source of transposase, wherein the nucleic acid fragment includes a nucleic acid sequence that contains a coding sequence and is positioned between at least two inverted repeats that can bind the transposase. In some embodiments of the invention the coding sequence is a detectable marker coding sequence that encodes a detectable marker or a selectable marker, including green fluorescent protein, luciferase or neomycin. The nucleic acid sequence of the gene transfer system can include one or more of (i) a weak promoter, for instance a carp β-actin promoter, (ii) a splice acceptor site and (iii) an internal ribosome entry site, each being operably linked to the detectable marker coding sequence. Alternatively, the nucleic acid sequence of the gene transfer system can include an analyte coding sequence located 5' of the detectable marker coding sequence and an internal ribosome entry site located therebetween, the internal ribosome entry site being operably linked to the detectable marker coding sequence. In some embodiments the analyte coding sequence is operably linked to a promoter. The nucleic acid fragment of the gene transfer system can be part of a plasmid or a recombinant viral vector.

The invention provides a method for producing a transgenic animal including introducing a nucleic acid fragment and a transposase source into a cell wherein the nucleic acid fragment includes a nucleic acid sequence that contains a heterologous coding sequence. The nucleic acid sequence is positioned between at least two inverted repeats wherein the inverted repeats can bind to the transposase to yield a transgenic cell. The cell is grown into a transgenic animal, and progeny can be derived from the transgenic animal.

Further provided by the present invention is a gene transfer system to introduce a nucleic acid sequence into the DNA of a fish, preferably a zebrafish, which includes a nucleic acid fragment containing a nucleic acid sequence that includes an internal ribosome entry site, wherein the nucleic acid fragment is capable of integrating into the genomic DNA of a fish. The nucleic acid sequence of the gene transfer system can further include a first coding sequence located 3' to and operably linked to the internal ribosome entry site and a second coding sequence located 5' to both the first coding sequence and the internal ribosome entry site.

Also provided by the present invention is a transgenic fish or fish cell, preferably a zebrafish or zebrafish cell, that comprises a heterologous internal ribosome entry site.

| Abbreviations | |
| --- | --- |
| EMCV | encephalomycarditis virus |
| GFP | green fluorescent protein |
| IRES | internal ribosome entry site |

BRIEF DESCRIPTION OF THE FIGURES

FIG. 1 illustrates the molecular reconstruction of a salmonid Tc1-like transposase gene. FIG. 1(A) is a schematic map of a salmonid TcE. The TcE includes inverted repeat/direct repeat (IR/DR) flanking sequences. Depicted on the nucleotide sequence between the inverted repeat/direct repeat sequences is the location of conserved domains in the transposase encoded by the nucleotide sequence. The numbers 1 and 340 refer to the amino acids of the transposase encoded by the nucleotide sequence. Abbreviations: DNA-recognition, a DNA-recognition/binding domain; NLS, a bipartite nuclear localization signal; the boxes marked D and E comprising the DDE domain (Doak, et al., *Proc. Natl. Acad, Sci., USA,* 91, 942–946 (1994)) that catalyzes transposition; G-rich, glycine-rich box; FIG. 1(B) provides an exemplary strategy for constructing an open reading frame for a salmonid transposase (SB1-SB3) and then systematically introducing amino acid replacements into this gene (SB4-SB10). Amino acid residues are shown using single letter code, typed black when different from the consensus. Positions within the transposase polypeptide that were modified by site-specific mutagenesis are indicated with arrows. Translational termination codons appear as asterisks, frameshift mutations are shown as #. Residues changed to the consensus are check-marked and typed in white italics. In the right margin, the results of various functional tests that were done at various stages of the reconstruction are indicated.

FIG. 2(A) is a double-stranded nucleic acid sequence encoding the SB protein (SEQ ID NO:3). FIG. 2(B) is the amino acid sequence (SEQ ID NO:1) of an SB transposase. The major functional domains are highlighted; see the legend to FIG. 1A for abbreviations.

FIG. 3(A) provides the SDS-PAGE analysis illustrating the steps in the expression and purification of N123. Lanes: 1) extract of cells containing expression vector pET21a; 2) extract of cells containing expression vector pET21a/N123 before induction with IPTG; 3) extract of cells containing expression vector pET21a/N123 after 2.5 hours of induction with IPTG; 4) partially purified N123 using $Ni^{2+}$-NTA resin. Molecular weights in kDa are indicated on the right. FIG. 3(B) illustrates the results of mobility-shift analysis studies to determine whether N123 bound to the inverted repeats of fish transposons. Lanes: 1) probe (a radiolabeled 300 bp DNA fragment comprising the left IR of the Tdr1 transposon (T)) only without any protein; 2) extract of cells containing expression vector pET21a; 3) 10,000-fold dilution of the N123 preparation shown in lane 4 of Panel A; 4) same as lane 3 plus a 1000-fold molar excess of unlabelled probe as competitor DNA; 5) same as lane 3 plus a 1000-fold molar excess of an inverted repeat fragment of a zebrafish Tdr1 element (z-IR) as competitor DNA; 6–13) 200,000-, 100,000-, 50,000-, 20,000-, 10,000-, 5,000-, 2,500-, and 1,000-fold dilutions of the N123 preparation shown in lane 4 of Panel A.

FIG. 4 provides the DNase I footprinting of deoxyribonucleoprotein complexes formed by N123.

FIG. 5 illustrates the integration activity of SB in human HeLa cells.

FIG. 7 illustrates the integration of neomycin resistance-marked transposons into the chromosomes of HeLa cells.

FIG. 10 illustrates a preferred screening strategy using IRS-PCR (interspersed repetitive sequence polymerase chain reaction).

The X superimposed on the central DANA element to represents a missing element or a mutated primer binding site in the genome of another zebrafish strain. The various amplified sequence tagged sites (STSs) are identified by lowercase letter (a through g), beginning with the longest detectable PCR product. The products marked with an X are not produced in the PCR reaction if genomes with defective "X-DNA" are amplified. Elements separated by more than about 2000 base pairs (bp) and elements having the wrong orientation relative to each other are not amplified efficiently.

FIG. 11 illustrates a preferred method for using an expression control sequence-trap transposon vector. Abbreviations: I, intron; E, exon.

FIG. 12 illustrates a preferred method for using a gene-trap transposon vector. FIG. 12(A) is a gene-trap that contains a GFP operably linked to a splice acceptor site and an IRES. FIG. 12(B) is a gene trap similar to FIG. 12(A), but encodes an activator which activates expression of a GFP coding sequence, elsewhere in the genome, thereby amplifying the level of GFP expression over what it would be were the GFP coding sequence in the gene trap vector. Abbreviations: I, intron; E, exon.

FIG. 16 illustrates an inverse PCR strategy to identify genomic DNA adjacent to an inserted nucleic acid fragment.

DETAILED DESCRIPTION

Figure 3:
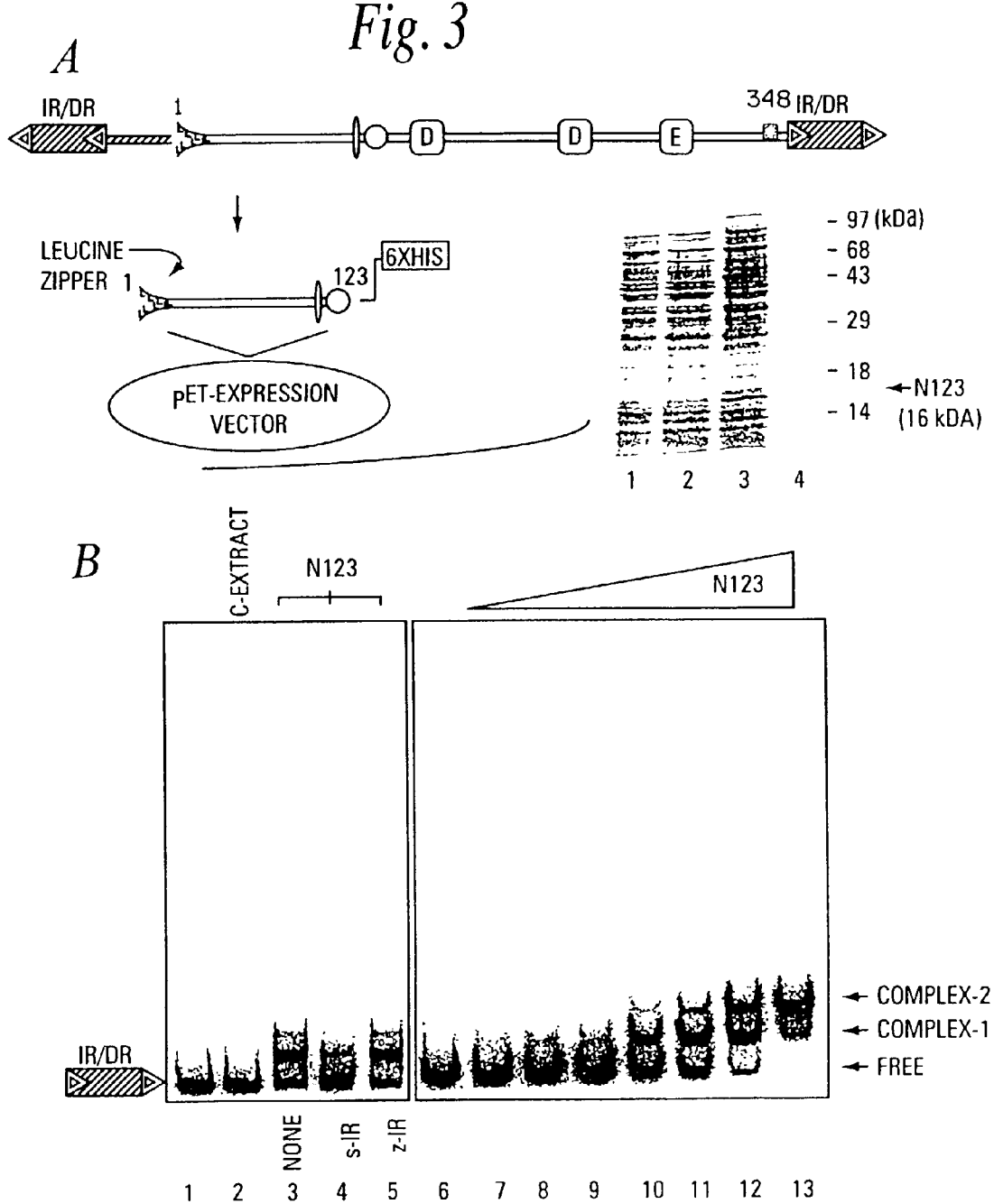
FIG. 3 illustrates the DNA-binding activities of an N-terminal derivative (N123) of the SB transposase.

The present invention relates to novel transposases and the transposons that are used to introduce nucleic acid sequences into the DNA of a cell. A transposase is an enzyme that is capable of binding to DNA at regions of DNA termed inverted repeats. Preferably a transposon contains two inverted repeats that flank an intervening nucleic acid sequence, i.e., there is an inverted repeat 5' to and 3' to the intervening nucleic acid sequence. Inverted repeats of an SB transposon can include two direct repeats and preferably include at least one direct repeat. The transposase binds to recognition sites in the inverted repeats and catalyzes the incorporation of the transposon into DNA.

Transposons are mobile, in that they can move from one position on DNA to a second position on DNA in the presence of a transposase. There are two fundamental components of any mobile cut-and-paste type transposon system, a source of an active transposase and the DNA sequences that are recognized and mobilized by the transposase. Mobilization of the DNA sequences permits the intervening nucleic acid between the recognized DNA sequences to also be mobilized.

DNA-transposons, including members of the Tc1/mariner superfamily, are ancient residents of vertebrate genomes (Radice et al., 1994 Mol. Gen. Genet., 244, 606–612; Smit and Riggs, 1996 Proc. Natl. Acad. Sci. USA 93, 1443–1448). However, neither autonomous copies of this class of transposon nor a single case of a spontaneous mutation caused by a TcE insertion have been proven in vertebrate animals. While evidence has been presented suggesting that the zebrafish genome contains active transposons, (Lam et al W. L., et al., Proc. Natl. Acad. Sci., USA, 93, 10870–10875 (1996)), neither autonomous copies of this class of transposon nor a single case of a spontaneous mutation caused by a TcE insertion have been rigorously proven in vertebrate animals. This is in contrast to retroposons whose phylogenetic histories of mutating genes in vertebrates is documented (Izsvak et al., 1997). Failure to isolate active DNA-transposons from vertebrates has greatly hindered ambitions to develop these elements as vectors for germline transformation and insertional mutagenesis. However, the apparent capability of salmonid TcEs for horizontal transmission between two teleost orders (Ivics et al., 1996, supra) suggested that this particular subfamily of fish transposons might be transferred through even larger evolutionary distances.

Reconstructions of ancestral archetypal genes using parsimony analysis have been reported (Jermann et al., 1995. Nature 374, 57–59; Unnikrishnan et al., 1996, Stewart, 1995 Nature 374, 12–13). However, such a strategy requires vertical transmission of a gene through evolution for phylogenetically backtracking to the root sequence. Because parsimony analysis could not resolve the phylogenetic relationships between salmonid TcEs, the present invention utilizes the approach of reconstructing a consensus sequence from inactive elements belonging to the same subfamily of transposons. The resurrection of a functional promoter of the L1 retrotransposon in mouse (Adey et al., 1994 Proc. Natl. Acad. Sci. USA 91, 1569–1573) has previously been reported.

A strategy for obtaining an active gene is not without risks. The consensus sequence of transposase pseudogenes from a single organism may simply reflect the mutations that had occurred during vertical inactivation that have subsequently been fixed in the genome as a result of amplification of the mutated element. For instance, most Tdr1 elements isolated from zebrafish contain a conserved, 350-bp deletion in the transposase gene (Izsvak et al., 1995, supra). Therefore, their consensus is expected to encode an inactive element. In the present invention, because independent fixation of the same mutation in different species is unlikely, a consensus from inactive elements of the same subfamily of transposons from several organisms is derived to provide a sequence for an active transposon.

Both the transposase coding regions and the inverted repeats (IRs) of salmonid-type TcEs accumulated several mutations, including point mutations, deletions and insertions, and show about 5% average pairwise divergence (Ivics et al., 1996, supra). Example 1 describes the methods that were used to reconstruct a transposase gene of the salmonid subfamily of fish elements using the accumulated phylogenetic data. This analysis is provided in the EMBL database as DS30090 from FTP.EBI.AC.AK in directory/pub/databases/embl/align and the product of this analysis was a consensus sequence for an inactive SB protein. All the elements that were examined were inactive due to deletions and other mutations. A salmonid transposase gene of the SB transposase family was created using PCR-mutagenesis through the creation of 10 constructs as provided in FIG. 1 and described in Example 1.

This sequence can then be modified further, as described here, to produce active members of the SB protein family.

The SB protein typically recognizes nucleotide sequences located within inverted repeats on a nucleic acid fragment and each inverted repeat includes at least one direct repeat. The gene transfer system of this aspect of the invention, therefore, comprises two components: a transposase and a cloned, nonautonomous (i.e., non-self inserting) salmonid-type element or transposon (referred to herein as a nucleic acid fragment having at least two inverted repeats) that carries the inverted repeats of the transposon substrate DNA. When put together these two components provide active transposon activity. In use, the transposase binds to the direct repeats in the inverted repeats and promotes integration of the intervening nucleic acid sequence into DNA of a cell including chromosomes and extra chromosomal DNA of fish as well as mammalian cells. This transposon does not appear to exist in nature.

The transposase that was reconstructed using the methods of Example 1 represents one member of a family of proteins that can bind to the inverted repeat region of a transposon to effect integration of the intervening nucleic acid sequence into DNA, preferably DNA in a cell. One example of the family of proteins of this invention is provided as SEQ ID NO:1 (see FIG. 2B). This family of proteins is referred to herein as SB proteins. The proteins of this invention are provided as a schematic in FIG. 1A. The proteins include, from the amino-terminus moving to the carboxy-terminus, a paired-like domain with leucine zipper, one or more nuclear localizing domains (NLS) domains and a catalytic domain including a DD(34)E box (i.e., a catalytic domain containing two invariable aspartic acid residues, D(153) and D(244), and a glutamic acid residue, E(279), the latter two separated by 43 amino acids) and a glycine-rich box as detailed in an example in FIG. 2. The SB family of proteins includes the protein having the amino acid sequence of SEQ ID NO: 1. Preferably, a member of the SB family of proteins also includes proteins with an amino acid sequence that shares at least an 80% amino acid identity to SEQ ID NO:1. Amino acid identity is defined in the context of a homology comparison between the member of the SB family of proteins and SEQ ID NO:1. The two amino acid sequences are aligned in a way that maximizes the number of amino acids that they have in common along the lengths of their sequences; gaps in either or both sequences are permitted in making the alignment in order to maximize the number of shared amino acids, although the amino acids in each sequence must nonetheless remain in their proper order. The percentage amino acid identity is the higher of the following two numbers: (a) the number of amino acids that the two polypeptides have in common within the alignment, divided by the number of amino acids in the member of the SB family of proteins, multiplied by 100; or (b) the number of amino acids that the two polypeptides have in common within the alignment, divided by the number of amino acids in the reference SB protein, i.e., SEQ ID NO:1, multiplied by 100.

Proteins of the SB family are transposases, that is, they are able to catalyze the integration of nucleic acid into DNA of a cell. In addition, the proteins of this invention are able to bind to the inverted repeat sequences of SEQ ID NOs:4–5 and direct repeat sequences (SEQ ID NOs:6–9) from a transposon as well as a consensus direct repeat sequence (SEQ ID NO:10). The SB proteins preferably have a molecular weight range of about 35 kD to about 40 kD on about a 10% SDS-polyacrylamide gel.

To create an active SB protein, suitable for further modification, a number of chromosomal fragments were sequenced and identified by their homology to the zebrafish transposon-like sequence Tdr1, from eleven species of fish (Ivics et al., 1996, supra). Next these and other homologous sequences were compiled and aligned. The sequences were identified in either GenBank or the EMBL database. Others have suggested using parsimony analysis to arrive at a consensus sequence but in this case parsimony analysis could not resolve the phylogenetic relationships among the salmonid-type TcEs that had been compiled. A consensus transposon was then engineered by changing selected nucleotides in codons to restore the amino acids that were likely to be in that position. This strategy assumes that the most common amino acid in a given position is probably the original (active) amino acid for that locus. The consensus sequence was examined for sites at which it appeared that C->T mutations had been fixed where deamination of $^{5m}$C residues may have occurred (which leads to C being converted to T which in turn can lead to the "repair" of the mismatched G residue to an A). In these instances, the "majority-rule" consensus sequence was not always used. Next various expected activities of the resurrected transposase were tested to ensure the accuracy of the engineering.

The amino acid residues described herein employ either the single letter amino acid designator or the three-letter abbreviation. Abbreviations used herein are in keeping with the standard polypeptide nomenclature. All amino acid residue sequences are represented herein by formulae with left-to-right orientation in the conventional direction of amino-terminus to carboxy-terminus.

Although particular amino acid sequences encoding the transposases of this invention have been described, there are a variety of conservative changes that can be made to the amino acid sequence of the SB protein without altering SB activity. These changes are termed conservative mutations, that is, an amino acid belonging to a grouping of amino acids having a particular size or characteristic can be substituted for another amino acid, particularly in regions of the protein that are not associated with catalytic activity or DNA binding activity, for example. Other amino acid sequences of the SB protein include amino acid sequences containing conservative changes that do not significantly alter the activity or binding characteristics of the resulting protein. Substitutes for an amino acid sequence may be selected from other members of the class to which the amino acid belongs. For example, the nonpolar (hydrophobic) amino acids include alanine, leucine, isoleucine, valine, proline, phenylalanine, tryptophan, and tyrosine. The polar neutral amino acids include glycine, serine, threonine, cysteine, tyrosine, asparagine and glutamine. The positively charged (basic) amino acids include arginine, lysine and histidine. The negatively charged (acidic) amino acids include aspartic acid and glutamic acid. Such alterations are not expected to substantially affect apparent molecular weight as determined by polyacrylamide gel electrophoresis or isoelectric point. Particularly preferred conservative substitutions include, but are not limited to, Lys for Arg and vice versa to maintain a positive charge; Glu for Asp and vice versa to maintain a negative charge; Ser for Thr so that a free —OH is maintained; and Gln for Asn to maintain a free $NH_2$.

The SB protein has catalytic activity to mediate the transposition of a nucleic acid fragment containing recognition sites that are recognized by the SB protein. The source of the SB protein can be the protein introduced into a cell, or a nucleic acid introduced into the cell. The SB protein can be introduced into the cell as ribonucleic acid, including mRNA; as DNA present in the cell as extrachromosomal DNA including, but not limited to, episomal DNA, as plasmid DNA, or as viral nucleic acid. In addition to a ribonucleotide sequence that is translated to yield a sequence of amino acids, an mRNA typically includes a guanine added to the 5' end of the mRNA to form a 5' cap. The 5' cap region can be methylated at several locations as described by Lewin, B., *Genes VI*, Oxford University Press, pp. 171–172 (1997). An mRNA also typically includes a sequence of polyadenylic acid (i.e., a poly(A) tail) at the 3' end of the mRNA.

Further, DNA encoding the SB protein can be stably integrated into the genome of the cell for constitutive or inducible expression. Where the SB protein is introduced into the cell as nucleic acid, the SB encoding sequence is preferably operably linked to a promoter. There are a variety of promoters that could be used including, but not limited to, constitutive promoters, tissue-specific promoters, inducible promoters, and the like. Promoters are regulatory signals that bind RNA polymerase in a cell to initiate transcription of a downstream (3' direction) coding sequence. A DNA sequence is operably linked to an expression control sequence, such as a promoter when the expression control sequence controls and regulates the transcription and translation of that DNA sequence. The term "operably linked" includes having an appropriate start signal (e.g., ATG) in front of the DNA sequence to be expressed and maintaining the correct reading frame to permit expression of the DNA sequence under the control of the expression control sequence to yield production of the desired protein product.

One nucleic acid sequence encoding the SB protein is provided as SEQ ID NO:3. In addition to the conservative changes discussed above that would necessarily alter the SB-encoding nucleic acid sequence, there are other DNA or RNA sequences encoding an SB protein having the same amino acid sequence as an SB protein such as SEQ ID NO:3, but which take advantage of the degeneracy of the three letter codons used to specify a particular amino acid. For example, it is well known in the art that the following RNA codons (and therefore, the corresponding DNA codons, with a T substituted for a U) can be used interchangeably to code for each specific amino acid:

| | |
|---|---|
| Phenylalanine (Phe or F) | UUU or UUC |
| Leucine (Leu or L) | UUA, UUG, CUU, CUC, CUA or CUG |
| Isoleucine (Ile or I) | AUU, AUC or AUA |
| Methionine (Met or M) | AUG |
| Valine (Val or V) | GUU, GUC, GUA, GUG |
| Serine (Ser or S) | UCU, UCC, UCA, UCG, AGU, AGC |
| Proline (Pro or P) | CCU, CCC, CCA, CCG |
| Threonine (Thr or T) | ACU, ACC, ACA, ACG |
| Alanine (Ala or A) | GCU, GCG, GCA, GCC |
| Tyrosine (Tyr or Y) | UAU or UAC |
| Histidine (His or H) | CAU or CAC |
| Glutamine (Gln or Q) | CAA or CAG |
| Asparagine (Asn or N) | AAU or AAC |
| Lysine (Lys or K) | AAA or AAG |
| Aspartic Acid (Asp or D) | GAU or GAC |
| Glutamic Acid (Glu or E) | GAA or GAG |
| Cysteine (Cys or C) | UGU or UGC |
| Arginine (Arg or R) | CGU, CGC, CGA, CGG, AGA, AGC |
| Glycine (Gly or G) | GGU or GGC or GGA or GGG |
| Termination codon | UAA, UAG or UGA |

Further, a particular DNA sequence can be modified to employ the codons preferred for a particular cell type. For example, the preferred codon usage for *E. coli* is known, as are preferred codon usages for animals and humans. These changes are known to those of ordinary skill in the art and are therefore considered part of this invention.

Also contemplated in this invention are antibodies directed to an SB protein of this invention. An "antibody" for purposes of this invention is any immunoglobulin, including antibodies and fragments thereof that specifically binds to an SB protein. The antibodies can be polyclonal, monoclonal and chimeric antibodies. Various methods are known in the art that can be used for the production of polyclonal or monoclonal antibodies to SB protein. See, for example, *Antibodies: A Laboratory Manual,* Harlow and Lane, eds., Cold Spring Harbor Laboratory Press: Cold Spring Harbor, N.Y. (1988).

Nucleic acid encoding the SB protein can be introduced into a cell as a nucleic acid vector such as a plasmid, or as a gene expression vector, including a viral vector. The nucleic acid can be circular or linear. Methods for manipulating DNA and protein are known in the art and are explained in detail in the literature such as Sambrook et al, (1989) *Molecular Cloning: A Laboratory Manual.,* Cold Spring Harbor Laboratory Press or Ausubel, R. M., ed. (1994). *Current Protocols in Molecular Biology.* A vector, as used herein, refers to a plasmid, a viral vector or a cosmid that can incorporate nucleic acid encoding the SB protein or the nucleic acid fragment of this invention. The term "coding sequence" or "open reading frame" refers to a region of nucleic acid that can be transcribed and/or translated into a polypeptide in vivo when placed under the control of the appropriate regulatory sequences.

Another aspect of this invention relates to a nucleic acid fragment, sometimes referred to as a transposon or transposon element, that includes a nucleic acid sequence positioned between at least two inverted repeats. Each inverted repeat preferably includes at least two direct repeats (hence, the name IR/DR). A direct repeat is typically between about 25 and about 35 base pairs in length, preferably about 29–31 base pairs in length. Notwithstanding the above, however, an inverted repeat can contain only one direct "repeat," in which event it is not actually a "repeat" but is nonetheless a nucleotide seqeunce having at least about 80% identity to a consensus direct repeat sequence as described more fully below. The transposon element is a linear nucleic acid fragment (extending from the 5' end to the 3' end, by convention) that can be used as a linear fragment or circularized, for example in a plasmid.

In a preferred embodiment of the transposon element, there are two direct repeats in each inverted repeat sequence. The direct repeats (which number, in this embodiment, four) have similar nucleotide sequences, as described in more detail below. An inverted repeat on the 5' or "left" side of a nucleic acid fragment of this embodiment typically comprises a direct repeat (i.e., a left outer repeat), an intervening region, and a second direct repeat (i.e., a left inner repeat). An inverted repeat on the 3' or "right" side of a nucleic acid fragment of this embodiment comprises a direct repeat (i.e., a right inner repeat), an intervening region, and a second direct repeat (i.e., a right outer repeat). The intervening region within an inverted repeat is generally at least about 150 base pairs in length, preferably at least about 160 base pairs in length. The intervening region is preferably no greater than about 200 base pairs in length, more preferably no greater than about 180 base pairs in length. The nucleotide sequence of the intervening region of one inverted repeat may or may not be similar to the nucleotide sequence of an intervening region in another inverted repeat.

Most transposons have perfect inverted repeats, whereas the inverted repeats that bind SB protein generally have at least about 80% to identity to a consensus direct repeat, preferably about 90% identity to a consensus direct repeat. A preferred consensus direct repeat is 5'-CAKTGRGTCR-GAAGTTTACATACACTTAAG-3' (SEQ ID NO:10) where K is G or T, and R is G or A. The presumed core binding site of SB protein is nucleotides 4 through 22 of SEQ ID NO:10. Nucleotide identity is defined in the context of a homology comparison between a direct repeat and SEQ ID NO:10. The two nucleotide sequences are aligned in a way that maximizes the number of nucleotides that they have in common along the lengths of their sequences; gaps in either or both sequences are permitted in making the alignment in order to maximize the number of shared nucleotides, although the nucleotides in each sequence must nonetheless remain in their proper order. The percentage nucleotide identity is the higher of the following two numbers: (a) the number of nucleotides that the two sequences have in common within the alignment, divided by the number of nucleotides in the direct repeat, multiplied by 100; or (b) the number of nucleotides that the two sequences have in common within the alignment, divided by the number of nucleotides in the reference direct repeat, i.e., SEQ ID NO:10, multiplied by 100. Examples of direct repeat sequences that bind to SB protein include: a left outer repeat 5'-GTTGAAGTCG-GAAGTTTACATACACTTAAG-3' (SEQ ID NO:6); a left inner repeat 5'-CAGTGGGTCAGAAGTTTACATACAC-TAAGG-3' (SEQ ID NO:7); a right inner repeat 5'-CAGTGGGTCAGAAGTTAACATACACTCAATT-3' (SEQ ID NO:8); and a right outer repeat 5'-AGT-TGAAGTCGGAAGTTTACATACACCTTAG-3' (SEQ ID NO:9).

In one embodiment the direct repeat sequence includes at least the following sequence: ACATACAC (SEQ ID NO:11).

One preferred inverted repeat sequence of this invention is

```
5'-AGTTGAAGTC GGAAGTTTAC ATACACTTAA GTTGGAGTCA TTAAAACTCG   SEQ ID NO:4

TTTTTCAACT ACACCACAAA TTTCTTGTTA ACAAACAATA GTTTTGGCAA

GTCAGTTAGG ACATCTACTT TGTGCATGAC ACAAGTCATT TTTCCAACAA

TTGTTTACAG ACAGATTATT TCACTTATAA TTCACTGTAT CACAATTCCA

GTGGGTCAGA AGTTTACATA CACTAA-3'
``` direct repeat (i.e., a right outer repeat). The intervening region within an inverted repeat is generally at least about and another preferred inverted repeat sequence of this invention is

```
5'-TTGAGTGTAT GTTAACTTCT GACCCACTGG GAATGTGATG AAAGAAATAA   SEQ ID NO:5

AAGCTGAAAT GAATCATTCT CTCTACTATT ATTCTGATAT TTCACATTCT

TAAAATAAAG TGGTGATCCT AACTGACCTT AAGACAGGGA ATCTTTACTC
```

-continued

```
GGATTAAATG TCAGGAATTG TGAAAAAGTG AGTTTAAATG TATTTGGCTA

AGGTGTATGT AAACTTCCGA CTTCAACTG-3'.
```

The inverted repeat (SEQ ID NO:5) contains the poly(A) signal AATAAA at nucleotides 104–109. This poly(A) signal can be utilized by a coding sequence present in the nucleic acid fragment to result in addition of a poly(A) tail to an mRNA. The addition of a poly(A) tail to an mRNA typically results in increased stability of that mRNA relative to the same mRNA without the poly(A) tail. Preferably, the inverted repeat (SEQ ID NO:5) is present on the 3' or "right side" of a nucleic acid fragment that comprises two direct repeats in each inverted repeat sequence.

The direct repeats are preferably the portion of the inverted repeat that bind to the SB protein to permit insertion and integration of the nucleic acid fragment into the cell. The site of DNA integration for the SB proteins occurs at TA base pairs (see FIG. 7B).

The inverted repeats flank a nucleic acid sequence which is inserted into the DNA in a cell. The nucleic acid sequence can include all or part of an open reading frame of a gene (i.e., that part of a gene encoding protein), one or more expression control sequences (i.e., regulatory regions in nucleic acid) alone or together with all or part of an open reading frame. Preferred expression control sequences include, but are not limited to promoters, enhancers, border control elements, locus-control regions or silencers. In a preferred embodiment, the nucleic acid sequence comprises a promoter operably linked to at least a portion of an open reading frame.

As illustrated in the examples, the combination of the nucleic acid fragment of this invention comprising a nucleic acid sequence positioned between at least two inverted repeats wherein the inverted repeats can bind to an SB protein and wherein the nucleic acid fragment is capable of integrating into DNA in a cell, in combination with an SB protein (or nucleic acid encoding the SB protein to deliver SB protein to a cell) results in the integration of the nucleic acid sequence into the cell. Alternatively, it is possible for the nucleic acid fragment of this invention to be incorporated into DNA in a cell through non-homologous recombination through a variety of as yet undefined, but reproducible mechanisms. In either event the nucleic acid fragment can be used for gene transfer.

As described in the examples, the SB family of proteins mediates integration in a variety of cell types and a variety of species. The SB protein facilitates integration of the nucleic acid fragment of this invention with inverted repeats into both pluripotent (i.e., a cell whose descendants can differentiate into several restricted cell types, such as hematopoietic stem cells or other stem cells) and totipotent cells (i.e., a cell whose descendants can become any cell type in an organism, e.g., embryonic stem cells). It is likely that the gene transfer system of this invention can be used in a variety of cells including animal cells, bacteria, fungi (e.g., yeast) or plants. Animal cells can be vertebrate or invertebrate. Cells such as oocytes, eggs, and one or more cells of an embryo are also considered in this invention. Mature cells from a variety of organs or tissues can receive the nucleic acid fragment of this invention separately, alone, or together with the SB protein or nucleic acid encoding the SB protein. Cells receiving the nucleic acid fragment or the SB protein and capable of receiving the nucleic acid fragment into the DNA of that cell include, but are not limited to, lymphocytes, hepatocytes, neural cells, muscle cells, a variety of blood cells, and a variety of cells of an organism. Example 4 provides methods for determining whether a particular cell is amenable to gene transfer using this invention. The cells can be obtained from vertebrates or invertebrates. Preferred invertebrates include crustaceans or mollusks including, but not limited to shrimp, scallops, lobster, clams, or oysters.

Vertebrate cells also incorporate the nucleic acid fragment of this invention in the presence of the SB protein. Cells from fish, birds and other animals can be used, as can cells from mammals including, but not limited to, rodents, such as rats or mice, ungulates, such as cows or goats, sheep, swine or cells from a human.

The DNA of a cell that acts as a recipient of the nucleic acid fragment of this invention includes any DNA in contact with the nucleic acid fragment of this invention in the presence of an SB protein. For example, the DNA can be part of the cell genome or it can be extrachromosomal, such as an episome, a plasmid, a circular or linear DNA fragment. Targets for integration are double-stranded DNA.

The combination of the nucleic acid fragment of this invention including a nucleic acid sequence positioned between at least two inverted repeats wherein the inverted repeats can bind to an SB protein and wherein the nucleic acid fragment is capable of integrating into DNA of a cell and a transposase or nucleic acid encoding a transposase, wherein the transposase is an SB protein, including SB proteins that include an amino acid sequence that is at least about 80% identical to SEQ ID NO:1 is useful as a gene transfer system to introduce nucleic acid sequence into the DNA of a cell. In a preferred embodiment, the SB protein comprises the amino acid sequence of SEQ ID NO:1 and in another preferred embodiment the DNA encoding the transposase can hybridize to the DNA of SEQ ID NO:3 under the following hybridization conditions: in 30% (v/v) formamide in 0.5×SSC, 0.1% (w/v) SDS at 42° C. for 7 hours.

Gene transfer vectors for gene therapy can be broadly classified as viral vectors or non-viral vectors. The use of the nucleic acid fragment of this invention as a transposon in combination with an SB protein represents a tremendous advancement in the field of non-viral DNA-mediated gene transfer. Up to the present time, viral vectors have been found to be more efficient at introducing and expressing genes in cells. There are several reasons why non-viral gene transfer is superior to virus-mediated gene transfer for the development of new gene therapies. For example, adapting viruses as agents for gene therapy restricts genetic design to the constraints of that virus genome in terms of size, structure and regulation of expression. Non-viral vectors are generated largely from synthetic starting materials and are therefore more easily manufactured than viral vectors. Non-viral reagents are less likely to be immunogenic than viral agents making repeat administration possible. Non-viral vectors are more stable than viral vectors and therefore better suited for pharmaceutical formulation and application than are viral vectors.

Current non-viral gene transfer systems are not equipped to promote integration of nucleic acid into the DNA of a cell, including host chromosomes. As a result, stable gene transfer frequencies using non-viral systems have been very low; 0.1% at best in tissue culture cells and much less in primary cells and tissues. The present system is a non-viral gene transfer system that facilitates integration and markedly improves the frequency of stable gene transfer.

In the gene transfer system of this invention the SB protein can be introduced into the cell as a protein or as nucleic acid encoding the protein. In one embodiment the nucleic acid encoding the protein is RNA and in another, the nucleic acid is DNA. Further, nucleic acid encoding the SB protein can be incorporated into a cell through a viral vector, anionic or cationic lipid, or other standard transfection mechanisms including electroporation, particle bombardment or microinjection used for eukaryotic cells. Following introduction of nucleic acid encoding SB, the nucleic acid fragment of this invention can be introduced into the same cell.

Similarly, the nucleic acid fragment can be introduced into the cell as a linear fragment or as a circularized fragment, preferably as a plasmid or as recombinant viral DNA. Preferably the nucleic acid sequence comprises at least a portion of an open reading frame to produce an amino-acid containing product. In a preferred embodiment the nucleic acid sequence encodes at least one protein and includes at least one promoter selected to direct expression of the open reading frame or coding region of the nucleic acid sequence. The protein encoded by the nucleic acid sequence can be any of a variety of recombinant proteins new or known in the art. In one embodiment the protein encoded by the nucleic acid sequence is a marker protein such as GFP, chloramphenicol acetyltransferase (CAT), β-galactosidase (lacZ), and luciferase (LUC). In another embodiment, the protein encoded by the nucleic acid is a growth hormone, for example to promote growth in a transgenic animal, or insulin-like growth factors (IGFs).

In one embodiment of a transgenic animal, the protein encoded by the nucleic acid fragment is a product for isolation from a cell. Transgenic animals as bioreactors are known. Protein can be produced in quantity in milk, urine, blood or eggs. Promoters are known that promote expression in milk, urine, blood or eggs and these include, but are not limited to, casein promoter, the mouse urinary protein promoter, β-globin promoter and the ovalbumin promoter respectively. Recombinant growth hormone, recombinant insulin, and a variety of other recombinant proteins have been produced using other methods for producing protein in a cell. Nucleic acid encoding these or other proteins can be incorporated into the nucleic acid fragment of this invention and introduced into a cell. Efficient incorporation of the nucleic acid fragment into the DNA of a cell occurs when an SB protein is present. Where the cell is part of a tissue or part of a transgenic animal, large amounts of recombinant protein can be obtained. There are a variety of methods for producing transgenic animals for research or for protein production including, but not limited to those described by Hackett et al. (*The molecular biology of transgenic fish*. In *Biochemistry and Molecular Biology of Fishes* (Hochachka & Mommsen, eds) Vol. 2, pp. 207–240 (1993)). Other methods for producing transgenic animals include the teachings of M. Markkula et al., *Rev. Reprod.*, 1, 97–106 (1996); R. T. Wall et al., *J. Dairy Sci.*, 80, 2213–2224 (1997); J. C. Dalton, et al., *Adv. Exp. Med. Biol.*, 411, 419–428 (1997); and H. Lubon et al., *Transfus. Med. Rev.*, 10, 131–143 (1996). Transgenic zebrafish were made, as described in Example 6. The system has also been tested through the introduction of the nucleic acid with a marker protein into mouse embryonic stem cells (ES) and it is known that these cells can be used to produce transgenic mice (A. Bradley et al., *Nature,* 309, 255–256 (1984)).

In general, there are two methods to achieve improved stocks of commercially important animals. The first is classical breeding, which has worked well for land animals, but it takes decades to make major changes. Controlled breeding, growth rates in coho salmon (*Oncorhynchus kisutch*) increased 60% over four generations and body weights of two strains of channel catfish (*Ictalurus punctatus*) were increased 21 to 29% over three generations. The second method is genetic engineering, a selective process by which genes are introduced into the chromosomes of animals or plants to give these organisms a new trait or characteristic, like improved growth or greater resistance to disease. The results of genetic engineering have exceeded those of breeding in some cases. In a single generation, increases in body weight of 58% in common carp (*Cyprinus carpio*) with extra rainbow trout growth hormone I genes, more than 1000% in salmon with extra salmon growth hormone genes, and less in trout were obtained. The advantage of genetic engineering in fish, for example, is that an organism can be altered directly in a very short periods of time if the appropriate gene has been identified. The disadvantage of genetic engineering in fish is that few of the many genes that are involved in growth and development have been identified and the interactions of their protein products is poorly understood. Procedures for genetic manipulation are lacking in many economically important animals. The present invention provides an efficient system for performing insertional mutagenesis (gene tagging) and efficient procedures for producing transgenic animals. Prior to this invention, transgenic DNA is not efficiently incorporated into chromosomes. Only about one in a million of the foreign DNA molecules integrates into the cellular genome, generally several cleavage cycles into development. Consequently, most transgenic animals are mosaic. As a result, animals raised from embryos into which transgenic DNA has been delivered must be cultured until gametes can be assayed for the presence of integrated foreign DNA. Many transgenic animals fail to express the transgene due to position effects. A simple, reliable procedure that directs early integration of exogenous DNA into the chromosomes of animals at the one-cell stage is needed. The present system helps to fill this need, as described in more detail below.

The transposon system of this invention has applications to many areas of biotechnology. Development of transposable elements for vectors in animals permits the following: 1) efficient insertion of genetic material into animal chromosomes using the methods given in this application. 2) identification, isolation, and characterization of genes involved with growth and development through the use of transposons as insertional mutagens (e.g., see Kaiser et al., 1995, "Eukaryotic transposable elements as tools to study gene structure and function." In *Mobile Genetic Elements,* IRL Press, pp. 69–100). 3) identification, isolation and characterization of transcriptional regulatory sequences controlling growth and development. 4) use of marker constructs for quantitative trait loci (QTL) analysis. 5) identification of genetic loci of economically important traits, besides those for growth and development, i.e., disease resistance (e.g., Anderson et al., 1996, *Mol. Mar. Biol. Biotech.,* 5, 105–113). In one example, the system of this invention can be used to produce sterile transgenic fish. Broodstock with inactivated genes could be mated to produce sterile offspring for either biological containment or for maximizing growth rates in aquacultured fish.

In yet another use of the gene transfer system of this invention, the nucleic acid fragment is modified to incorporate a gene to provide a gene therapy to a cell. The gene is placed under the control of a tissue specific promoter or of a ubiquitous promoter or one or more other expression control sequences for the expression of a gene in a cell in need of that gene. A variety of genes are being tested for a variety of gene therapies including, but not limited to, the CFTR gene for cystic fibrosis, adenosine deaminase (ADA) for immune system disorders, factor IX globins and interleukin-2 (IL-2) genes for blood cell diseases, alpha-1-antitrypsin for lung disease, and tumor necrosis factors (TNFs), phenylalanine/hydroxylase for PKU (phenylketouria), and multiple drug resistance (MDR) proteins for cancer therapies.

These and a variety of human or animal specific gene sequences including gene sequences to encode marker proteins and a variety of recombinant proteins are available in the known gene databases such as GenBank, and the like.

Further, the gene transfer system of this invention can be used as part of a process for working with or for screening a library of recombinant sequences, for example, to assess the function of the sequences or to screen for protein expression, or to assess the effect of a particular protein or a particular expression control sequence on a particular cell type. In this example, a library of recombinant sequences, such as the product of a combinatorial library or the product of gene shuffling, both techniques now known in the art and not the focus of this invention, can be incorporated into the nucleic acid fragment of this invention to produce a library of nucleic acid fragments with varying nucleic acid sequences positioned between constant inverted repeat sequences. The library is then introduced into cells together with the SB protein as discussed above.

An advantage of this system is that it is not limited to a great extent by the size of the intervening nucleic acid sequence positioned between the inverted repeats. The SB protein has been used to incorporate transposons ranging from 1.3 kilobases (kb) to about 5.0 kb and the mariner transposase has mobilized transposons up to about 13 kb. There is no known limit on the size of the nucleic acid sequence that can be incorporated into DNA of a cell using the SB protein.

Rather, what is limiting can be the method by which the gene transfer system of this invention is introduced into cells. For example, where microinjection is used, there is very little restraint on the size of the intervening sequence of the nucleic acid fragment of this invention. Similarly, lipid-mediated strategies do not have substantial size limitations. However, other strategies for introducing the gene transfer system into a cell, such as viral-mediated strategies could limit the length of the nucleic acid sequence positioned between their terminal repeats, according to this invention.

The two-part SB transposon system can be delivered to cells via viruses, including retroviruses (including lentiviruses), adenoviruses, adeno-associated viruses, heipesviruses, and others. There are several potential combinations of delivery mechanisms for the transposon portion containing the transgene of interest flanked by the inverted terminal repeats (IRs) and the gene encoding the transposase. For example, both the transposon and the transposase gene can be contained together on the same recombinant viral genome; a single infection delivers both parts of the SB system such that expression of the transposase then directs cleavage of the transposon from the recombinant viral genome for subsequent integration into a cellular chromosome. In another example, the transposase and the transposon can be delivered separately by a combination of viruses and/or non-viral systems such as lipid-containing reagents. In these cases either the transposon and/or the transposase gene can be delivered by a recombinant virus. In every case, the expressed transposase gene directs liberation of the transposon from its carrier DNA (viral genome) for integration into chromosomal DNA.

This invention also relates to methods for using the gene transfer system of this invention. In one method, the invention relates to the introduction of a nucleic acid fragment comprising a nucleic acid sequence positioned between at least two inverted repeats into a cell. In a preferred embodiment, efficient incorporation of the nucleic acid fragment into the DNA of a cell occurs when the cell also contains an SB protein. As discussed above, the SB protein can be provided to the cell as SB protein or as nucleic acid encoding the SB protein. Nucleic acid encoding the SB protein can take the form of RNA or DNA. The protein can be introduced into the cell alone or in a vector, such as a plasmid or a viral vector. Further, the nucleic acid encoding the SB protein can be stably or transiently incorporated into the genome of the cell to facilitate temporary or prolonged expression of the SB protein in the cell. Further, promoters or other expression control sequences can be operably linked with the nucleic acid encoding the SB protein to regulate expression of the protein in a quantitative or in a tissue-specific manner. As discussed above, the SB protein is a member of a family of SB proteins preferably having at least an 80% amino acid sequence identity to SEQ ID NO:1 and more preferably at least a 90% amino acid sequence identity to SEQ ID NO:1. Further, the SB protein contains a DNA-binding domain, a catalytic domain (having transposase activity) and an NLS signal.

The nucleic acid fragment of this invention is introduced into one or more cells using any of a variety of techniques known in the art such as, but not limited to, microinjection, combining the nucleic acid fragment with lipid vesicles, such as anionic or cationic lipid vesicles, particle bombardment, electroporation, microinjection, DNA condensing reagents (e.g., calcium phosphate, polylysine or polyethyleneimine) or incorporating the nucleic acid fragment into a viral vector and contacting the viral vector with the cell. Where a viral vector is used, the viral vector can include any of a variety of viral vectors known in the art including viral vectors selected from the group consisting of a retroviral vector, an adenovirus vector or an adeno-associated viral vector.

The gene transfer system of this invention can readily be used to produce transgenic animals that carry a particular marker or express a particular protein in one or more cells of the animal. Methods for producing transgenic animals are known in the art and the incorporation of the gene transfer system of this invention into these techniques does not require undue experimentation. The examples provided below teach methods for creating transgenic fish by microinjecting the gene transfer system into a cell of an embryo of the fish. Further, the examples also describe a method for introducing the gene transfer system into mouse embryonic stem cells. Methods for producing transgenic mice from embryonic stem cells are well known in the art. Further a review of the production of biopharmaceutical proteins in the milk of transgenic dairy animals (see Young et al., *BIO PHARM* (1997), 10, 34–38) and the references provided therein detail methods and strategies for producing recombinant proteins in milk. The methods and the gene transfer system of this invention can be readily incorporated into these transgenic techniques without undue experimentation in view of what is known in the art and particularly in view of this disclosure.

The nucleic acid fragments of this invention in combination with the SB protein or nucleic acid encoding the SB protein is a powerful tool for germline transformation, for the production of transgenic animals, as methods for introducing nucleic acid into DNA in a cell, for insertional mutagenesis, and for gene-tagging in a variety of species. Two strategies are diagramed in FIG. 9.

Due to their inherent ability to move from one chromosomal location to another within and between genomes, transposable elements have been exploited as genetic vectors for genetic manipulations in several organisms. Transposon-tagging is a technique in which transposons are mobilized to "hop" into genes, thereby inactivating them by insertional mutagenesis. These methods are discussed by Evans et al., (*TIG*, 13, 370–374 (1997)). In the process, the inactivated genes are "tagged" by the transposable element which then can be used to recover the mutated allele. The ability of the human and other genome projects to acquire gene sequence data has outpaced the ability of scientists to ascribe biological function to the new genes. Therefore, the present invention provides an efficient method for introducing a tag into the genome of a cell. Where the tag is inserted into a location in the cell that disrupts expression of a protein that is associated with a particular phenotype, expression of an altered phenotype in a cell containing the nucleic acid of this invention permits the association of a particular phenotype with a particular gene that has been disrupted by the nucleic acid fragment of this invention. Here the nucleic acid fragment functions as a tag. Primers designed to sequence the genomic DNA flanking the nucleic acid fragment of this invention can be used to obtain sequence information about the disrupted gene.

In another application of this invention, the invention provides a method for mobilizing a nucleic acid sequence in a cell. In this method the nucleic acid fragment of this invention is incorporated into DNA in a cell, as provided in the discussion above. Additional SB protein or nucleic acid encoding the SB protein is introduced into the cell and the protein is able to mobilize (i.e. move) the nucleic acid fragment from a first position within the DNA of the cell to a second position within the DNA of the cell. The DNA of the cell can be chromosomal DNA or extra chromosomal DNA. The term "genomic DNA" is used herein to include both chromosomal DNA and extra chromosomal DNA. The method permits the movement of the nucleic acid fragment from one location in the genome to another location in the genome, or for example, from a plasmid in a cell to the genome of that cell.

Additional modifications of the transposable elements disclosed herein can further increase the efficiency of insertion of genetic material into animal chromosomes so as to allow the identification, isolation, and characterization of genes involved with growth, development and disease, and the identification, isolation and characterization of transcriptional regulatory sequences controlling growth, development and disease. Examples of the types of modifications that can be made to the transposable elements disclosed herein include the construction of transposable elements taking the form of expression control sequence-trap transposon vectors, gene-trap transposon vectors, and dicistronic gene expression transposon vectors.

In a preferred embodiment of the nucleic acid fragment of the invention, the nucleic acid sequence that is flanked by the inverted repeats (sometimes referred to herein as the "intervening nucleic acid sequence") comprises at least one coding sequence. In an embodiment that is particularly suited for use in functional genomic analysis as well as gene discovery, the coding sequence encodes a detectable and/or selectable marker. For ease of reference, a coding sequence that encodes a detectable and/or selectable marker will be referred to as a "detectable marker coding sequence," however it is to be understood that this coding sequence can encode any type of detectable or selectable marker, or a protein that activates a detectable or selectable marker supplied in trans or in cis. An example of a selectable marker is neomycin. Preferred detectable markers include luciferase, β-galactosidase, fluorescent proteins, chloramphenicol acetyl transferase (CAT) and other exogenous proteins detectable by their fluorescence, enzymatic activity or immunological properties. Non-limiting examples of fluorescent proteins include GFP, Yellow Fluorescent Protein and Blue Fluorescent Protein. Typically, a detectable marker coding sequence is operably linked to a poly(A) signal that is present 3' to the detectable marker coding sequence. Useful activators of detectable markers supplied in trans or in cis (see, e.g., FIG. 12(B)) include those that can bind to specific promoters and cause the transcription of a coding sequence operably linked to the promoter. In embodiments of the method of the invention that utilize activatable detectable markers, the cells into which the nucleic acid fragment is introduced preferably also contain a detectable marker coding sequence operably linked to a promoter that can be activated by an activator protein. An example of a protein encoded by a detectable marker coding sequence of an expression control sequence-trap vector or a gene-trap vector is the trans-acting activator protein tTA (tetracycline controlled transactivator) (Clontech, Palo Alto, Calif.), which interacts with a tetracycline response element to which a detectable marker coding sequence is operably linked.

Optionally, the intervening nucleic acid sequence of the nucleic acid fragment of the invention further comprises at least one expression control sequence that is operably linked to the detectable marker coding sequence. In one preferred embodiment, the expression control sequence comprises a promoter, more preferably a weak promoter. As used herein, the terms "weak promoter" or "minimal promoter" refer to a promoter that by itself does not have the ability to direct high expression of the coding sequence to which it is operably linked. However, when the nucleic acid fragment inserts into a cell's genomic DNA so that the weak promoter is operably linked to at least one expression control sequence already present in the cell's DNA, preferably at least one of which is an enhancer (see, for instance, FIG. 11), the weak promoter can direct the expression of the detectable marker coding sequence in tissues in which the enhancer is active and at levels higher than the weak promoter would direct expression when not operably linked to the enhancer. An enhancer is a cis-acting nucleotide sequence that generally increases the activity of promoters and typically can function in either orientation and either upstream or downstream of a promoter. Examples of suitable weak promoters useful in vertebrate cells are the promoter for the carp β-actin coding sequence (Liu et al., *BioTechnol.*, 8, 1268–1272 (1990); (Caldovic, L., et al., *Mol Mar Biol Biotechnol.*, 4 51–61 (1995)), and the Herpes Simplex Virus thymidine kinase promoter.

The invention includes a method for using the nucleic acid fragment of the invention to identify or "trap" expression control sequences present in genomic DNA. Preferably, the coding sequence of the nucleic acid fragment encodes a detectable marker and is operably linked to at least one expression control sequence present in the nucleic acid sequence of the nucleic acid fragment. The detectable marker is preferably a fluorescent protein or a selectable marker. In a nucleic fragment especially well-suited for this use, the intervening nucleic acid sequence comprises a detectable marker coding sequence operably linked to a promoter, preferably a weak promoter. In the method of the invention, an expression control sequence-trap transposon vector comprising the nucleic acid fragment is introduced into a cell, preferably along with a source of transposase, such that the nucleic acid fragment inserts into the DNA of the cell. The transposase source can be a nucleic acid and/or a protein as described in detail hereinbelow. For instance, a vector containing the nucleic acid fragment can contain a second coding sequence encoding a transposase. In another aspect, the cell can contain a coding sequence that encodes an SB transposase. Alternatively, an mRNA encoding an SB transposase or an SB transposase itself can be introduced into the cell.

The nucleic acid fragment can insert within a coding sequence present in a cell's DNA that can result in the insertional inactivation of that coding sequence, or the nucleic acid fragment can insert into DNA outside of a coding sequence. Either type of insertion can result in expression of the detectable marker provided the nucleic acid fragment inserts near an appropriate expression control sequence. Preferably, the nucleic acid fragment integrates into the DNA of the cell or its progeny within a domain that contains an expression control sequence, more preferably an enhancer. It is possible that the nucleic acid fragment of this embodiment will insert in-frame into a coding sequence in a cell's DNA and is expressed by virtue of the endogenous promoter and not the weak promoter. When this happens, the nucleic acid fragment will be operating as a gene trap.

The nucleic acid fragment comprising a detectable marker operably linked to a weak promoter can be used to detect the presence of an expression control sequence that regulates the expression of the promoter. Preferably, enhancers are detected. As enhancers activate promoters located within the same domain defined by border elements as the enhancer, the expression of the detectable marker generally indicates that the nucleic acid fragment has inserted within the same domain as an enhancer.

Expression control sequences can be detected in accordance with the invention in any type of cell, without limitation. Preferred cells are pluripotent or totipotent cells, including an oocyte, a cell of an embryo, an egg and a stem cell. However, cells can be derived from any type of tissue, differentiated or undifferentiated. Cells from fish, birds and other animals can be used, as can cells from mammals including, but not limited to, rodents, such as rats or mice, ungulates, such as cows or goats, sheep, swine or cells from a human.

It is possible for enhancers to be active only at specific times or specific tissues within an animal. Thus, evaluation of expression of the detectable marker encoded by an inserted nucleic acid fragment in an animal can result in identification of enhancers that have distinct spatial and/or temporal expression. For instance, detection of the detectable marker only at specific times during the cell cycle or during development of the animal indicates that the enhancer is active only at specific times (i.e., developmental stage-specific expression). Detection of the detectable marker only in specific tissues of the whole animal indicates that the trapped enhancer is a tissue-specific enhancer.

Preferably the cells are grown into an animal and the cells assayed for expression of the detectable marker are present in an animal. Thus, cells that can be detected include progeny of a cell that contain the nucleic acid fragment comprising the detectable marker coding sequence. The animal can be an embryo, an adult, or at a developmental phase between embryo and adult. Preferably the animal is an embryo. Expression of the detectable marker in the animal can be assayed by methods known to the art. For instance, assay of β-galactosidase expression or immunological detection of a foreign protein like CAT can be used. Another example of evaluating expression of a detectable marker in an embryo is the expression of fluorescent proteins in the optically clear zebrafish embryo.

Optionally the expression control sequence detection method includes observing at least one phenotype of a cell that contains the integrated nucleic acid fragment, and comparing it to a cell that does not contain the nucleic acid fragment to determine whether the phenotype of the first cell is altered. An altered phenotype can be detected by methods known to the art. Alternatively, the cell that contains the integrated nucleic acid fragment can be grown into an animal, and animal phenotypes similarly compared.

The method can be used to make a transgenic animal having tissue-specific expression of a preselected coding sequence. For instance, a first transgenic animal can be produced that contains an expression control sequence-trap that is expressed in a particular tissue, and the detectable marker coding sequence encodes a trans-acting activator. A second and independent transgenic animal can be produced that contains a preselected coding sequence that is operably linked to a promoter that is activated by the activator encoded by the expression control sequence-trap that is present in the first transgenic animal. Crossing the two transgenic animals can result in transgenic progeny that contain i) the expression control sequence-trap that is expressed in a particular tissue and ii) the preselected coding sequence operably linked to a promoter that is activated by the activator encoded by the expression control sequence-trap. Tissue-specific expression of the activator protein will cause tissue-specific expression of the preselected coding sequence. This aspect of the invention is particularly useful in those animals where tissue-specific promoters have not yet been identified.

To obtain information about the location in the cell genome into which the nucleic acid fragment has inserted, the method optionally includes cleaving the DNA of the cell with a restriction endonuclease capable of cleaving at a restriction site within the intervening nucleic acid sequence of the nucleic acid fragment to yield at least one restriction fragment containing at least a portion of the integrated nucleic acid fragment, which portion comprises at least a portion of an inverted repeat sequence along with an amount of genomic DNA of the cell, which genomic DNA is adjacent to the inverted repeat sequence. The specificities of numerous endonucleases are well known and can be found in a variety of publications, e.g. Sambrook et al.; *Molecular Cloning: A Laboratory Manual;* Cold Spring Harbor Laboratory: New York (1989). The intervening nucleic acid sequence thus preferably includes a restriction endonuclease recognition site, preferably a 6-base recognition sequence. Following integration of the nucleic acid fragment into the cell DNA, the cell DNA is isolated and digested with the restriction endonuclease. Where a restriction endonuclease is used that employs a 6-base recognition sequence, the cell DNA is cut into about 4000-base pair restriction fragments on average. Since the site of DNA integration mediated by the SB proteins generally occurs at TA base pairs and the TA base pairs are typically duplicated such that an integrated nucleic acid fragment is flanked by TA base pairs, TA base pairs will be immediately adjacent to an integrated nucleic acid fragment. The genomic DNA of the genomic fragment is typically immediately adjacent to the TA base pairs on either side of the integrated nucleic acid fragment.

After the DNA of the cell is digested, the genomic fragments can be cloned in a vector using methods well known to the art allowing individual clones containing genomic fragments comprising at least a portion of the integrated nucleic acid fragment and genomic DNA of the cell adjacent to the inserted nucleic acid fragment to be identified. A non-limiting example of identifying the desired genomic fragments include hybridization with a probe complementary to the sequence of the inverted repeats. Alternatively, linkers can be added to the ends of the digested fragments to provide complementary sequence for PCR primers. Where linkers are added, PCR reactions are used to amplify fragments using primers from the linkers and primers binding to a nucleotide sequence within the inverted repeats.

Nucleotide sequences of the genomic DNA on either or both sides of the inserted nucleic acid fragment (i.e., flanking the inverse repeats) can be determined by nucleotide sequencing using methods well known to the art. The resulting nucleotide sequences are then used to search computer databases such as GenBank or EMBL for related sequences; if the nucleotide sequences encode a putative protein, the encoded amino acid sequences can also be used to search protein data bases such as SwissProt for related or homologous polypeptide sequences.

Alternatively, the restriction endonuclease used to cleave the cell DNA is one that is incapable of cleaving the nucleic acid sequence of the nucleic acid fragment. Non-limiting examples of characterizing the resulting restriction fragments include adding linkers to the ends of the digested fragments to provide complementary sequences for PCR primers described above or for inverse PCR. For instance, to identify fragments that contain nucleotides on either or both sides of the inserted nucleic acid fragment using inverse PCR, genomic DNA is isolated from cells that express a detectable marker such as GFP or show a consequential phenotypic response after mutagenesis with a transposon of the present invention (see, e.g., FIG. 16). The DNA is then cleaved with one or more restriction endonucleases that cut outside of the transposon and the resulting fragments of DNA are circularized using DNA ligase. About one in a million genomic fragments may contain the transposon. The genomic sequence can then be PCR amplified in two steps. The first PCR amplification uses the P2 external primers IR/DR(L)-p2 CCACAGGTACACCTCCAATTGACTC (SEQ ID NO:72) and IR/DR(R)-P2 GTGGTGATCCTAACTGACCTTAAGAC (SEQ ID NO:73). Following 10–15 cycles of amplification, the products of round 1 of amplification are reamplified using internal P1 primers that further augment the number of copies of the interrupted genetic sequence. The internal primers are IR/DR(L)-p1 GTGTCATGCACAAAGTAGATGTCC (SEQ ID NO:74) and IR/DR(R)-P1 CTCGGATTAAATGTCAGGAATTGTG (SEQ ID NO:75). Primers P1 and P2 are complementary to sequences within the DR elements of the SB transposon. The amplified DNA sequences are isolated for sequencing and/or other analysis, and nucleotide sequences of the genomic DNA on either or both sides of the inserted nucleic acid fragment can thus be determined.

In another preferred embodiment of the nucleic acid fragment of the invention comprising a coding sequence operably linked to at least one expression control sequence, the intervening nucleic acid sequence includes a splice acceptor site and/or an internal ribosomal entry site (IRES), each of these expression control sequences being operably linked to the coding sequence, preferably a detectable marker coding sequence. Preferably the intervening nucleic acid sequence comprises both a splice acceptor site and an IRES, and the IRES is positioned between the splice acceptor site and the detectable marker coding sequence so as to ultimately permit ribosome binding to the detectable marker mRNA and thereby initiate translation of the detectable marker nucleotide sequence (see, for instance, FIGS. 12(A), 12(B)). In this regard, the splice acceptor site and/or an IRES are considered operably linked to a coding sequence when the splice acceptor site and/or the IRES is located 5' of the detectable marker coding sequence and is present in an mRNA containing the detectable marker coding sequence prior to processing of the mRNA. Preferably, the splice acceptor site is located 5' to the IRES, and the IRES is located 5' to the coding sequence to which a splice acceptor site and an IRES are operably linked.

The splice acceptor site acts to provide signals to target the sequences 3' to, i.e., following, the splice acceptor site, including the detectable marker coding sequence, to be present in the mRNA containing the detectable marker coding sequence provided there is an intron upstream of the splice acceptor site (Padgett, T., et al., *Am. Rev. Biochem. J.*, 55, 1119–1150 (1988)). Typically, a splice acceptor site includes a branch site and a 3' splice site. The consensus sequence of a branch site is typically a nucleotide sequence 5'-$P_{y80}$ N $P_{y80}$ $P_{y87}$ $P_{y87}$ $P_{u75}$ A $P_{y95}$, where $P_y$ is T or C, $P_u$ is A or G, and the subscripted number is the approximate percent occurrence of the appropriate nucleotide (see, for instance, Lewin, B., *Genes VI*, Oxford University Press, pp. 891–893 (1997)). The branch site is typically located 10 to 60 nucleotides 5' to the splice site, preferably 15 to 50 nucleotides 5' to the splice site. The 3' splice site is typically the nucleotide sequence $C_{55}AG$, where the subscripted number is the percent occurrence of the C, and the intron is cleaved after the G. Preferably the splice acceptor site is derived from the 3' end (i.e., the splice acceptor end) of the first intron (intron A) of the β-actin coding sequence of carp (Liu, Z., et al., *DNA Sequence—J. DNA Sequencing and Mapping*, Vol. 1, pp. 125–136 (1990)). Preferably nucleotides 1335–1571 of the nucleotides sequence available at GenBank Accession No. M24113, more preferably nucleotides 1485–1571, are particularly suitable for use in the present invention.

The maximum distance between splice acceptor site and IRES is unknown. However, the overall size of the nucleic acid fragment can have an effect on the efficiency of transposition of the nucleic acid fragment. For instance, the SB protein has been used to incorporate transposons ranging from 1.3 kilobases (kb) to about 6.0 kb and the mariner transposase has mobilized transposons up to about 13 kb. There is no known limit on the size of the nucleic acid sequence that can be incorporated into DNA of a cell using the SB protein. The IRES is typically positioned within about 0 to 7 bases of the translation initiation codon, e.g., ATG, of the coding sequence to which the IRES is operably linked. Typically, an IRES contains at least two translation initiation codons. Preferably, the IRES includes at least one translation initiation codon, and the IRES is ligated to the translation coding region such that an IRES translation initiation codon replaces the translation initiation codon of the coding sequence. An IRES allows ribosomal access to mRNA without a requirement for cap recognition and subsequent scanning to the initiator AUG (Pelletier, J. A., et al., *Nature,* 334, 320–325 (1988)). An IRES that can be used in the invention typically includes a viral IRES, preferably a picornavirus IRES, poliovirus IRES, mengovirus IRES, or EMCV IRES, more preferably a poliovirus IRES, mengovirus IRES, or EMCV IRES, and most preferably an EMCV IRES. An example of an EMCV IRES that can be used in the invention is nucleotides 234–848 of the nucleotide sequence available at GenBank Accession No. M81861. In some embodiments nucleotides 827–831 (GATA) are replaced with TGCT. This 615 base pair nucleotide sequence contains ATG codons at nucleotides 834–836 and 846–848. Typically, the ATG codon at nucleotides 834–836 is used as the translation initiation codon by the ribosome and a coding sequence (for instance a GFP coding sequence) can be fused to this ATG codon. However, in some embodiments it is preferable to fuse a coding sequence (for instance a GFP coding sequence) to the EMCV IRES so that the first codon of the coding sequence, i.e., the ATG codon, replaces the ATG codon at nucleotides 846–848 of the EMCV IRES. This typically results in the fused coding sequence beginning with the amino acid sequence MATT (SEQ ID NO:70), which is the sequence encoded by nucleotides 834–845 of the EMCV IRES.

Although the coding sequence included in the intervening nucleic acid sequence of the nucleic acid fragment of the invention typically contains a polyadenylation signal, it need not. In embodiments of the nucleic acid fragment containing a coding sequence that does not include a polyadenylation signal, the detectable marker coding sequence is preferably operably linked to a promoter located 5' to the coding sequence and a splice donor site located 3' of the coding sequence. When the nucleic acid fragment inserts into a region of genomic DNA that is not an exon of a genomic coding sequence, the resulting mRNA will generally be unstable due to the lack of a poly(A) tail. However, when the nucleic acid fragment of this aspect of the invention inserts into an exon and the exon is part of a coding sequence is then expressed, the mRNA containing the detectable marker may be stabilized when the splice donor splices with a downstream exon that encodes a poly(A) tail. This is known as a poly(A) trap.

The invention includes a method for using the nucleic acid fragment of the invention to identify or "trap" coding sequences present in genomic DNA, i.e. a "gene trap" transposon method that allows for gene discovery and functional analysis. Insertion of a transposon into genomic DNA can interrupt or mutate a genomic coding sequence. When a genomic coding sequence present in a cell is interrupted, and the detectable marker coding sequence is inserted in just the right way (in the correct direction, in-frame, and in an exon of the interrupted coding sequence), typically the detectable marker coding sequence is expressed spatially and temporally in the same way as the interrupted genomic coding sequence is expressed when not interrupted. This aspect of the invention can be used, for example, in gene discovery by providing for a method to insert a nucleic acid fragment into genomic DNA so that a genomic coding sequence no longer expresses a functional product, i.e., the insertion results in a loss-of-function mutation. Successful utilization of the transposon-derived vectors in the gene-trap and enhancer-trap methods of the invention without further modification was surprising in view of the possibility that the IR/DR sequences might contain cryptic promoter or splicing signals that would have interfered with the use of these vectors.

A genomic coding sequence in a cell's DNA can be identified according to the present invention by introducing a nucleic acid fragment comprising a coding sequence, preferably a detectable marker coding sequence, into a cell, preferably along with a source of transposase as described above, then detecting the detectable marker in the cell or its progeny. Preferably, the intervening nucleic acid sequence of the nucleic acid fragment includes a splice acceptor site and/or an IRES, each of which is operably linked to the coding sequence. As previously noted, the IRES is preferably located between the splice acceptor site and the detectable marker coding sequence. Additionally, the detectable marker coding sequence is preferably not operably linked to a promoter. The use of a splice acceptor site and an internal ribosome binding site operably linked to the detectable marker coding sequence expands the probability that the detectable marker coding sequence will be expressed when inserted into a genomic coding sequence: it is possible to get expression of the detectable marker coding sequence even if the transposon integrates in an intron or if it integrates out of frame with respect to the interrupted genomic coding sequence. Detection of the detectable marker in the cell or in progeny of the cell containing the nucleic acid fragment is indicative that the nucleic acid fragment has integrated within a genomic coding sequence of the cell. Genomic coding sequences can be detected in any type of cell as generally described above, including but not limited to an oocyte, a cell of an embryo, an egg cell or a stem cell, and in any type of tissue, differentiated or undifferentiated. Preferably, the detectable marker is expressed spatially and temporally in the same way as the genomic coding sequence is expressed when not interrupted.

Optionally the genomic coding sequence detection method includes observing at least one phenotype of a cell that contains the integrated nucleic acid fragment, and comparing it to a cell that does not contain the nucleic acid fragment to determine whether the phenotype of the first cell is altered. Alternatively, the cell that contains the integrated nucleic acid fragment can be grown into an animal, and animal phenotypes similarly compared. Additionally, the method optionally comprises cleaving the DNA of the cell with a restriction endonuclease to yield at least one restriction fragment containing at least a portion of the integrated nucleic acid fragment, which portion comprises an inverted repeat sequence along with an amount of genomic DNA of the cell, which genomic DNA is adjacent to the inverted repeat sequence. The intervening nucleic acid sequence thus preferably includes a restriction endonuclease recognition site, as described above in connection with the expression control region detection method. Restriction fragments containing portions of the inverted repeats and genomic DNA are sequenced, and the DNA flanking the inverted repeats and/or the amino acid sequences encoded thereby are used to search computer databases such as GenBank or SwissProt.

In yet another preferred embodiment of the nucleic acid fragment of the invention, the intervening nucleic acid sequence comprises a coding sequence, preferably a detectable marker coding sequence, and a second coding sequence located 5', i.e., upstream, of the detectable marker coding sequence. The detectable marker coding sequence typically is not operably linked to a promoter. Preferably the intervening nucleic acid sequence further comprises an IRES located between the detectable marker coding sequence and the second coding sequence, wherein the IRES is operably linked to the detectable marker coding sequence (see, for instance, FIG. 15). Optionally, the second coding sequence is operably linked to at least one expression control sequence. The expression control sequence to which the second coding sequence is optionally operably linked can include a splice acceptor site, an IRES or a promoter, preferably a promoter.

For reference, this second coding sequence is referred to as an "analyte coding sequence." The analyte coding sequence can include any coding sequence of interest including, for instance, a randomly inserted coding sequence from a library of DNA fragments or a preselected coding sequence. The nucleic acid sequence comprising the analyte coding sequence preferably includes at least one expression control sequence, including but not limited to expression control sequences that are associated with the analyte coding sequence in its wild type or native state, i.e., those expression control sequences operably linked to the coding sequence as it naturally exists in a cell. Preferably, at least one of the expression control sequences is a promoter. Useful promoters include constitutive and inducible promoters. Alternatively, the promoter can be the native promoter, i.e., the promoter that is normally operably linked to the analyte coding region. The detectable marker coding sequence can be operably linked to a splice acceptor site and/or an IRES. Preferably, in this aspect of the invention the detectable marker coding sequence is operably linked to an IRES (see, e.g., FIG. 15).

The analyte coding sequence can encode a protein that is biologically active, thereby allowing, for example, the evaluation and/or verification of the function of coding sequences and/or their protein products, as well as mutant rescue and transgenic analysis. Generally, insertion of a dicistronic vector that has an analyte coding sequence that encodes a biologically active protein can cause a gain-of-function mutation.

Alternatively, the analyte coding sequence can encode a protein that is incapable of performing the function of the wild-type, i.e., native, protein. This type of protein is typically inactive by virtue of an amino acid sequence altered relative to the native protein and can be used for the functional analysis of proteins using, for example, dominant-negative mutant analysis.

The nucleic acid sequence of this aspect of the invention can encode two mRNAs, one encoded by the detectable marker coding sequence and a second mRNA encoded by the analyte coding sequence. Preferably, the nucleic acid sequence of this aspect of the invention encodes one mRNA that includes two coding sequences, i.e., a dicistronic mRNA. While not intended to be limiting, a dicistronic vector of this aspect of the invention generally provides for the expression of a detectable marker coding sequence primarily when the analyte coding sequence is expressed.

The invention includes a method for identifying or analyzing the function of an analyte coding sequence that involves introducing into a host cell a dicistronic nucleic acid fragment of the invention that includes the analyte coding sequence and a detectable marker coding sequence, preferably together with a source of transposase, followed by detection of the detectable marker. The development of transposable elements for vectors in animals according to the present invention thus makes possible the identification, isolation, and characterization of coding sequences involved with growth, development and disease, and also the transcriptional regulatory sequences that control growth, development and disease. Preferably, the nucleic acid fragment used in this method of the invention, when read from left to right, contains at least the following elements in the following order: inverted repeats, the analyte coding sequence, the detectable marker coding sequence, and inverted repeats. In other words, the analyte coding sequence is located 5' of the detectable marker coding sequence, and the analyte coding sequence is transcribed first, followed by the detectable marker coding sequence. In this embodiment transcription of the two coding sequences in the nucleic acid fragment can result in a dicistronic mRNA. Preferably, the analyte coding sequence is not operably linked to either a splice acceptor site or an IRES, although it can be. While it is anticipated that insertion of the nucleic acid fragment into genomic DNA can result in the interruption of a genomic coding sequence, identification of an analyte coding sequence does not require the interruption of a genomic coding sequence. Preferably, the analyte coding sequence is operably linked to a promoter, as described above. The detectable marker coding sequence can be operably linked to a splice acceptor site and/or an IRES. Preferably, in this aspect of the method of the invention the detectable marker coding sequence is operably linked to an IRES (see, e.g., FIG. 15).

Thus, when the dicistronic transposon vector of this aspect of the invention inserts into DNA of a cell, the two coding sequences present in the transposon are transcribed, and a dicistronic mRNA is typically produced. Generally, the analyte coding sequence of the nucleic acid fragment will be translated by virtue of ribosome initiation via scanning from the 5' end of the mRNA. Typically the detectable marker coding sequence of the nucleic acid fragment will be translated by virtue of internal initiation mediated by the IRES element. Thus, the translation of the detectable marker, i.e., the second coding sequence of the dicistronic mRNA, provides a method to detect expression of the analyte coding sequence of the nucleic acid fragment. This is a significant advantage, as the expression of some biological coding sequences of interest can be difficult to monitor directly. The dicistronic gene expression transposon vectors of the invention will generally allow the expression of a biological coding sequence of interest to be detected.

Notably, there have been no previous reports of an IRES that functions in zebrafish. The EMCV IRES and others are derived from mammalian sources, and it is surprising that these sequences are able to direct internal ribosome entry in zebrafish. Millions of years of evolutionary divergence could easily have altered the domains of the translation factor(s) and/or other proteins that direct the interaction.

Figure 15:
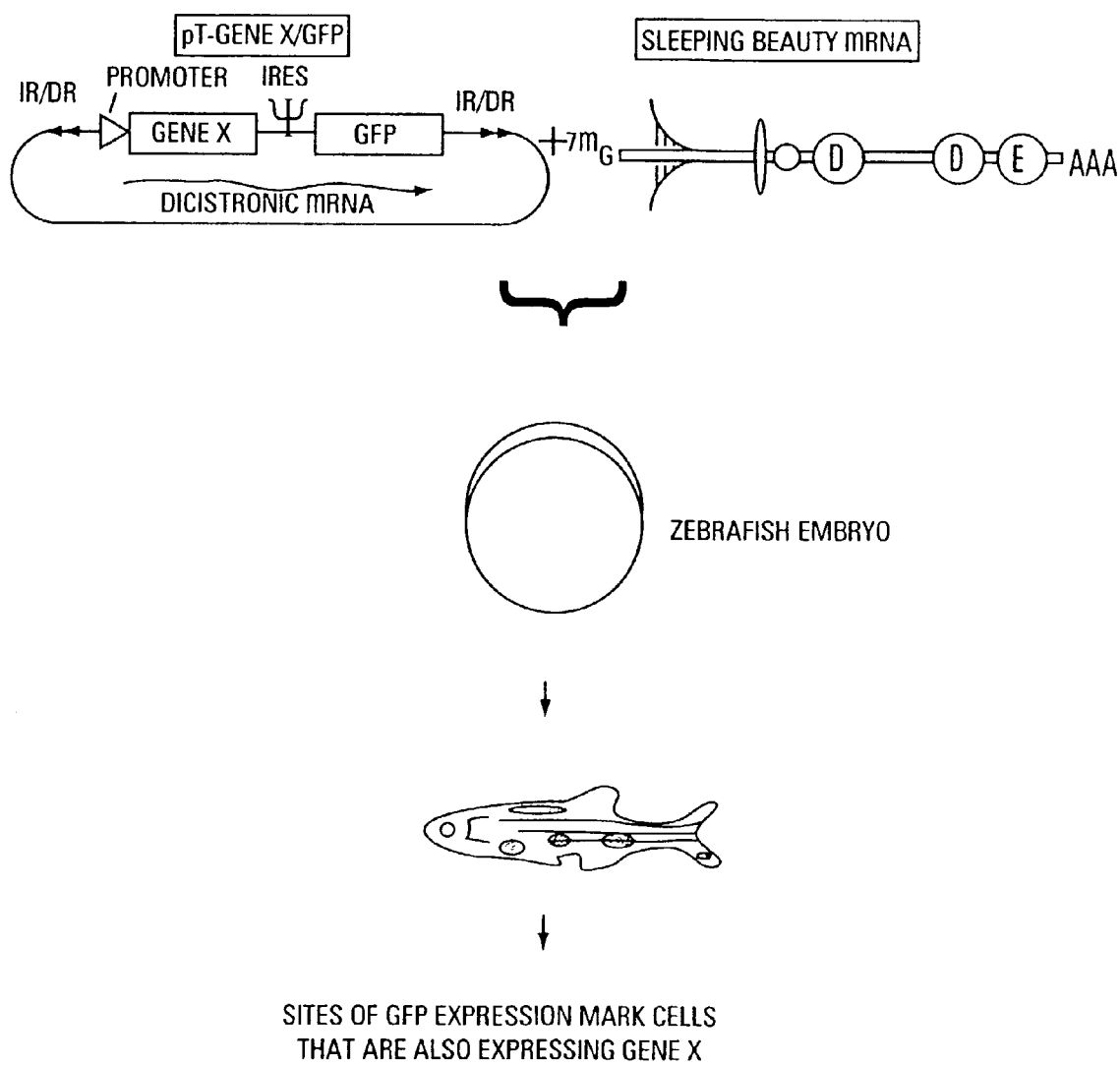
FIG. 15 illustrates a strategy for using dicistronic coding sequence expression transposon vectors.

A use of a dicistronic transposon vector of this aspect of the invention is depicted schematically in FIG. 15. The dicistronic transposon vector and mRNA encoding SB transposase can be microinjected into zebrafish embryos which are allowed to mature. Expression of GFP marks cells in which "Gene X" is also expressed. This allows analysis of the effects of "Gene X" on specific tissues; a form of mosaic analysis. Gene X may encode a protein or a portion of a protein, and the encoded protein can be beneficial or deleterious to the cells. It should be understood that the function of analyte coding sequences can be analyzed in any type of cell, including but not limited to an oocyte, a cell of an embryo, an egg cell or a stem cell, and in any type of tissue, differentiated or undifferentiated.

An alternative use of the dicistronic vector is to inject dicistronic mRNA encoded by a vector containing a nucleic acid fragment comprising the analyte coding sequence and the detectable marker coding sequence. An example of this embodiment is described in Example 9.

Optionally the method for identifying or analyzing the function of an analyte coding sequence includes observing the phenotype of a cell that contains the integrated nucleic acid fragment, and comparing it to a cell that does not contain the nucleic acid fragment to determine whether the phenotype of the first cell is altered, wherein an altered phenotype is indicative that the analyte coding sequence plays a function in the identified phenotype. Alternatively, the cell that contains the integrated nucleic acid fragment can be grown into an animal, and animal phenotypes similarly compared.

It can be seen that the nucleic acid fragments of the invention have applications to many areas of biotechnology and functional genomics. The invention allows efficient insertion of genetic material into the genomic DNA of a cell of animals, preferably vertebrate animals, for the mutation, evaluation of function, and subsequent cloning of a genomic coding sequence and/or genomic expression control sequences. The invention has the property of allowing identification of organisms in which the detectable marker that is encoded by the inserted nucleic acid fragment is expressed in specific tissues or at specific times in development. Another property of the invention is the ability to insert a biological coding sequence of interest into a cell's genomic DNA and evaluate the location and time of expression of the biological coding sequence of interest by assaying for the co-expressed downstream detectable marker coding sequence.

In a preferred embodiment of the gene transfer system of the invention, the system has two components: a nucleic acid fragment that comprises a nucleic acid sequence comprising a coding sequence, wherein the nucleic acid sequence is positioned between at least two inverted repeats that can bind to an SB protein, and a source of transposase. It is to be understood that the intervening nucleic acid sequence of the nucleic acid fragment can include any variation or feature herein disclosed, without limitation, and the nucleic acid fragment is one that is capable of integrating into DNA of a cell, as described more fully hereinabove. The nucleic acid fragment is preferably part of a plasmid or a recombinant viral vector. As already noted, the transposase source can be either a nucleic acid encoding the transposase or the transposase protein itself, and the transposase is preferably an SB protein.

Another embodiment of the gene transfer system is directed to the introduction of a nucleic acid fragment into the DNA of a human or a fish. This embodiment of the gene transfer system includes a nucleic acid fragment comprising a nucleic acid sequence that comprises an IRES, and the nucleic acid fragment is capable of integrating into the fish or human DNA. Preferably, the nucleic acid sequence of this embodiment further comprises a coding sequence located 3' to and operably linked to the IRES. Optionally, the nucleic acid sequence of this embodiment comprises a first coding sequence located 3' to and operably linked to the IRES, and a second coding sequence located 5' to both the first coding sequence and the IRES. It should be noted that in this particular embodiment of the gene transfer system, the nucleic acid sequence of the nucleic acid fragment need not be flanked by inverted repeats that bind an SB protein, nor is a source of transposase necessary, although these features are optionally included. The invention is further directed to a transgenic human or fish, preferably zebrafish, whose cells contain a nucleic acid fragment comprising an IRES as described, and its progeny. In a preferred embodiment, the invention is directed to a transgenic fish or fish cell comprising a IRES that is heterologous with respect to the fish genome, for example a viral IRES.

The invention also includes a method for producing a transgenic animal. A nucleic acid fragment of the invention, including any variation or feature herein disclosed, without limitation, and a source of transposase as described above are introduced into a cell. The nucleic acid fragment preferably contains a coding sequence that is heterologous with respect to the animal, i.e., it is not found in the animal's genome. However, the coding sequence can also be one that is endogenous to the animal. The cell or cells containing the nucleic acid fragment are then grown into an animal. The resulting animal can be transgenic, including a mosaic. Preferably, the nucleic fragment is integrated into both somatic and germline cells of the transgenic animal, and the transgenic animal is capable of transmitting the nucleic acid fragment to its progeny. The invention is further directed to a transgenic animal whose cells contain a nucleic acid fragment of the invention, and its progeny.

EXAMPLES

The following examples, while exemplary of the present invention, are not to be construed as specifically limiting the invention. Accordingly, variations and equivalents, now known or later developed, that would be within the purview of one skilled in the art are to considered to fall within the scope of this invention.

Example 1

Reconstruction of an SB Transposase

Recombinant DNA

Gene reconstruction-Phase 1: Reconstruction of a transposase open reading frame. The Tss1.1 element from Atlantic salmon (GenBank accession number L12206) was PCR-amplified using a primer pair flanking the defective transposase gene, FTC-Start and FTC-Stop to yield product SB1. Next, a segment of the defective transposase gene of the Tss1.2 element (L12207) was PCR-amplified using PCR primers FTC-3 and FTC-4, then further amplified with FTC-3 and FTC-5. The PCR product was digested with restriction enzymes NcoI and BlpI, underlined in the primer sequences, and cloned to replace the corresponding fragment in SB1 to yield SB2. Then, an approximately 250 bp HindIII fragment of the defective transposase gene of the Tsg1 element from rainbow trout (L12209) was isolated and cloned into the respective sites in SB2 to result in SB3. The Tss1 and Tsg1 elements were described in (Radice et al., 1994) and were kind gifts from S. W. Emmons.

```
FTC-Start:
5'-CCTCTAGGATCCGACATCATG          (SEQ ID NO:17)

FTC-Stop:
5'-TCTAGAATTCTAGTATTTGGTAGCATTG   (SEQ ID NO:18)

FTC-3:
5'-AACACCATGGGACCACGCAGCCGTCA     (SEQ ID NO:19)

FTC-4:
5'-CAGGTTATGTCGATATAGGACTCGTTTTAC (SEQ ID NO:20)

FTC-5:
5'-CCTTGCTGAGCGGCCTTTCAGGTTATGTCG (SEQ ID NO:21)
```

Gene reconstruction-Phase 2: Site-specific PCR mutagenesis of the SB3 open reading frame to introduce consensus amino acids. For PCR mutagenesis, two methods have been used: megaprimer PCR (Sarkar and Sommer, 1990 *BioTechniques* 8, 404–407) from SB4 through SB6, and Ligase Chain Reaction (Michael, 1994 *BioTechniques* 16, 410–412) for steps SB7 to SB10.

```
Oligonucleotide primers for product SB4 were the following:
FTC-7:   5'-TTGCACTTTTCGCACCAA                              (SEQ ID NO:22)
for Gln->Arg(74) and Asn->Lys(75);

FTC-13:  5'-GTACCTGTTTCCTCCAGCATC                           (SEQ ID NO:23)
for Ala->Glu(93);

FTC-8:   5'-GAGCAGTGGCTTCTTCCT                              (SEQ ID NO:24)
for Leu->Pro(121);

FTC-9:   5'-CCACAACATGATGCTGCC                              (SEQ ID NO:25)
for Leu->Met(193);

FTC-10:  5'-TGGCCACTCCAATACCTTGAC                           (SEQ ID NO:26)
for Ala->Val(265) and Cys->Trp(268);

FTC-11:  5'-ACACTCTAGACTAGTATTTGGTAGCATTGCC                 (SEQ ID NO:27)
for Ser->Ala(337) and Asn->Lys(339).

Oligonucleotide primers for product SB5:
B5-PTV:  5'-GTGCTTCACGGTTGGGATGGTG                          (SEQ ID NO:28)
for Leu->Pro(183), Asn->Thr(184) and Met->Val(185).

Oligonucleotide primers for product SB6:
FTC-DDE: 5'-ATTTTCTATAGGATTGAGGTCAGGGC                      (SEQ ID NO:29)
for Asp->Glu(279).

Oligonucleotide primers for products SB7 and SB8, in two steps:
PR-GAIS: 5'-GTCTGGTTCATCCTTGGGAGCAATTTCCAAACGCC             (SEQ ID NO:30)
for Asn->Ile(28), His->Arg(31) and Phe->Ser(21).

Oligonucleotide primers for product SB9:
KARL:    5'-CAAAACCGACATAAGAAAGCCAGACTACGG                  (SEQ ID NO:31)
for Pro->Arg(126);

RA:      5'-ACCATCGTTATGTTTGGAGGAAGAAGGGGGAGGCTTGCAAGCCG    (SEQ ID NO:32)
for Cys->Arg(166) and Thr->Ala(175);

EY:      5'-GGCATCATGAGGAAGGAAAATTATGTGGATATATTG            (SEQ ID NO:33)
for Lys->Glu(216) and Asp->Tyr(218);

KRV:     5'-CTGAAAAAGCGTGTGCGAGCAAGGAGGCC                   (SEQ ID NO:34)
for Cys->Arg(288);

VEGYP:   5'-GTGGAAGGCTACCCGAAACGTTTGACC                     (SEQ ID NO:35)
for Leu->Pro(324).

Oligonucleotide primers for product SB10:
FATAH:   5'-GACAAAGATCGTACTTTTTGGAGAAATGTC                  (SEQ ID NO:36)
for Cys->Arg(143).
```

Plasmids. For pSB10, the SB10 transposase gene was cut with EcoRI and BamHI, whose recognition sequences are incorporated and underlined above in the primers FTC-Start and FTC-Stop, filled in with Klenow and cloned into the Klenow-filled NotI sites of CMV-βgal (Clonetech), replacing the lacZ gene originally present in this plasmid. Because of the blunt-end cloning, both orientations of the gene insert were possible to obtain and the antisense direction was used as a control for transposase. For pSB10-ΔDDE, plasmid pSB10 was cut with MscI, which removes 322 bp of the transposase-coding region, and recircularized. Removal of the MscI fragment from the transposase gene deleted much of the catalytic DDE domain and disrupted the reading frame by introducing a premature translational termination codon.

Sequence alignment of 12 partial salmonid-type TcE sequences found in 8 fish species (available under DS30090 from FTP.EBI.AC.AK in directory/pub/databases/embl/align from the EMBL database) allowed us to derive a majority-rule, salmonid-type consensus sequence, and identify conserved protein and DNA sequence motifs that likely have functional importance (FIG. 1A).

Conceptual translation of the mutated transposase open reading frames and comparison with functional motifs in other proteins allowed us to identify five regions that are highly conserved in the SB transposase family (FIG. 1A): I) a paired box/leucine zipper motif at the N-terminus; ii) a DNA-binding domain; iii) a bipartite nuclear localization signal (NLS); iv) a glycine-rich motif close to the center of the transposase without any known function at present; and v) a catalytic domain consisting of three segments in the C-terminal half comprising the DDE domain that catalyzes the transposition. DDE domains were identified by Doak et al. in Tc1 mariner sequences (Doak et al., 1994 *Proc. Natl. Acad. Sci. USA* 91, 942–946). Multiple sequence alignment also revealed a fairly random distribution of mutations in transposase coding sequences; 72% had occurred at non-synonymous positions in codons. The highest mutation frequencies were observed at CpG dinucleotide sites which are highly mutable (Adey et al., 1994, supra). Although amino acid substitutions were distributed throughout the transposases, fewer mutations were detected at the conserved motifs (0.07 non-synonymous mutations per codon), as compared to protein regions between the conserved domains (0.1 non-synonymous mutations per codon). This observation indicated that some selection mechanism had maintained the functional domains before inactivation of transposons took place in host genomes. The identification of these putative functional domains was of key importance during the reactivation procedure.

The first step of reactivating the transposase gene, was to restore an open reading frame (SB1 through SB3 in FIG. 1B) from bits and pieces of two inactive TcEs from Atlantic salmon (*Salmo salar*) and a single element from rainbow trout (*Oncorhynchus mykiss*) (Radice et al., 1994, supra). SB3, which has a complete open reading frame after removal of stop codons and frameshifts, was tested in an excision assay similar to that described by Handler et al. (1993) but no detectable activity was observed. Due to non-synonymous nucleotide substitutions, the SB3 polypeptide differs from the consensus transposase sequence in 24 positions (FIG. 1B) which can be sorted into two groups; nine residues that are probably essential for transposase activity because they are in the presumed functional domains and/or conserved in the entire Tc1 family, and another fifteen residues whose relative importance could not be predicted. Consequently, a dual gene reconstruction strategy was undertaken. First, the putative functional protein domains of the transposase were systematically rebuilt one at a time by correcting the former group of mutations. Each domain for a biochemical activity was tested independently when possible. Second, in parallel with the first approach, a full-length, putative transposase gene was synthesized by extending the reconstruction procedure to all of the 24 mutant amino acids in the putative transposase.

Accordingly, a series of constructs was made to bring the coding sequence closer, step-by-step, to the consensus using PCR mutagenesis (SB4 through SB10 in FIG. 1B). As a general approach the sequence information predicted by the majority-rule consensus was followed. However, at some codons deamination of $^{5m}C$ residues of CpG sites occurred, and C->T mutations had been fixed in many elements. At R(288), where TpG's and CpG's were represented in equal numbers in the alignment, the CpG sequence was chosen because the CpG->TpG transition is more common in vertebrates than the TpG->CpG. The result of this extensive genetic engineering is a synthetic transposase gene encoding 340 amino acids (SB10 in FIGS. 1B and 2).

The reconstituted functional transposase domains were tested for activity. First, a short segment of the SB4 transposase gene (FIG. 1B) encoding an NLS-like protein motif was fused to the lacZ gene. The transposase NLS was able to mediate the transfer of the cytoplasmic marker-protein, β-galactosidase, into the nuclei of cultured mouse cells (Ivics et al., 1996, supra), supporting predictions that a bipartite NLS was a functional motif in SB and that our approach to resurrect a full-length, multifunctional enzyme was viable.

Example 2

Preparation of a Nucleic Acid Fragment with Inverted Repeat Sequences

In contrast to the prototypic Tc1 transposon from *Caenorhabditis elegans* which has short, 54-bp indirect repeat sequences (IRs) flanking its transposase gene, most TcEs in fish belong to the IR/DR subgroup of TcEs (Ivics et al., 1996; Izsvak et al., 1995, both supra) which have long, 210-250 bp IRs at their termini and directly repeated DNA sequence motifs (DRs) at the ends of each IR (FIG. 1A). However, the consensus IR sequences are not perfect repeats (i.e., similar, but not identical) indicating that, in contrast to most TcEs, these fish elements naturally possess imperfect inverted repeats. The match is less than 80% at the center of the IRs, but is perfect at the DRs, suggesting that this nonrandom distribution of dissimilarity could be the result of positive selection that has maintained functionally important sequence motifs in the IRs (FIG. 3). Therefore, DNA sequences at and around the DRs might carry cis-acting information for transposition and mutations within the IRs, but outside the DRs, would probably not impair the ability of the element to transpose. As a model substrate, a single salmonid-type TcE substrate sequence from *Tanichthys albonubes* (hereafter referred to as T), which has intact DR motifs whose sequences are only 3.8% divergent from the salmonid consensus, was chosen. The variation in the DNase-protected regions of the four DR sequences varied from about 83% to about 95%, see SEQ ID NOS:6–9.

A TcE from *Tanichthys albonubes* (L48685) was cloned into the SmaI site of pUC19 to result in pT. The donor construct for the integration assays, pT/neo, was made by cloning, after Klenow fill-in, an EcoRI/BamHI fragment of the plasmid pRc-CMV (Invitrogen, San Diego, Calif.) containing the SV40 promoter/enhancer, the neomycin resistance gene and an SV40 poly(A) signal into the StuI/MscI sites of pT. The StuI/MscI double digest of pT leaves 352 bp on the left side and 372 bp on the right side of the transposon and thus contains the terminal inverted repeats. An EcoRI digest of pT/neo removed a 350 bp fragment including the left inverted repeat of the transposon, and this plasmid, designated pT/neo-ΔIR, was used as a control for the substrate-dependence of transposase-mediated transgene integration (see Example 4)

Example 3

DNA Specificity of an SB Transposase

There are at least two distinct subfamilies of TcEs in the genomes of Atlantic salmon and zebrafish, Tss1/Tdr1 and Tss2/Tdr2, respectively. Elements from the same subfamily are more alike, having about 70% nucleic acid identity, even when they are from two different species (e.g., Tss1 and Tdr1) than members of two different subfamilies in the same species. For example, Tdr1 and Tdr2 are characteristically different in their encoded transposases and their inverted repeat sequences, and share only about 30% nucleic acid identity. It may be that certain subfamilies of transposons must be significantly different from each other in order to avoid cross mobilization. A major question is whether substrate recognition of transposases is sufficiently specific to prevent activation of transposons of closely related subfamilies.

The 12-bp DRs of salmonid-type elements, identical to the DRs of zebrafish-type TcEs, are part of the binding sites for SB. However, these binding-sites are 30 bp long. Thus, specific DNA-binding also involves DNA sequences around the DRs that are variable between TcE subfamilies in fish. Such a difference in the sequences of transposase binding sites might explain the inability of N123 to bind efficiently to zebrafish Tdr1 IRs, and may enable the transposase to distinguish even between closely related TcE subfamilies. Indeed, mutations of four base pairs in the 20-bp Tc1 binding site can abolish binding of transposase (Vos and Plasterk, 1994 *EMBO J.* 13, 6125–6132). The DR core motifs are likely involved primarily in transposase-binding while sequences around the DR motifs likely provide the specificity for this binding.

SB has four binding-sites in its transposon substrate DNA that are located at the ends of the IRs. These sites share about a 83% to about a 95% identity (by comparison of SEQ ID NOS:6–9). However, a zebrafish Tdr1 element lacking an internal transposase-binding site was apparently able to transpose. This observation agrees with the finding that removal of internal transposase-binding sites from engineered Tc3 elements did not lessen their ability to transpose (Colloms et al., 1994 *Nucl. Acids Res.* 22, 5548–5554), suggesting that the presence of internal transposase-binding sites is not essential for transposition. Multiple binding-sites for proteins, including transposases, are frequently associated with regulatory functions (Gierl et al., 1988 *EMBO J.* 7, 4045–4053). Consequently, the internal binding-sites for transposases in the IR/DR group of TcEs serve one or more regulatory purposes affecting transposition and/or gene expression.

Once in the nucleus, a transposase must bind specifically to its recognition sequences in the transposon. The specific DNA-binding domains of both the Tc1 and Tc3 transposases have been mapped to their N-terminal regions (Colloms et al., 1994, supra; Vos and Plasterk, 1994, supra). However, there is very little sequence conservation between the N-terminal regions of TcE transposases, suggesting that these sequences are likely to encode specific DNA-binding functions in these proteins. On the other hand, the N-terminal region of SB has significant structural and sequence similarities to the paired DNA-binding domain, found in the Pax family of transcription factors, in a novel combination with a leucine zipper-like motif (Ivics et al., 1996, supra). A gene segment encoding the first 123 amino acids of SB (N123), which presumably contains all the necessary information for specific DNA-binding and includes the NLS, was reconstructed (SB8 in FIG. 1B), and expressed in *E. coli*. N123 was purified via a C-terminal histidine tag as a 16 KDa polypeptide (FIG. 3A).

Induction of N123 was in *E. coli* strain BL21(DE3) (Novagen) by the addition of 0.4 mM IPTG at 0.5 O.D. at 600 nm and continued for 2.5 h at 30° C. Cells were sonicated in 25 mM HEPES, pH 7.5, 1 M NaCl, 15% glycerol, 0.25% Tween 20, 2 mM β-mercaptoethanol, 1 mM PMSF) and 10 mM imidazole (pH 8.0) was added to the soluble fraction before it was mixed with $Ni^{2+}$-NTA resin (Qiagen) according to the recommendations of the manufacturer. The resin was washed with 25 mM HEPES (pH 7.5), 1 M NaCl, 30% glycerol, 0.25% Tween 20, 2 mM β-mercaptoethanol, 1 mM PMSF and 50 mM imidazole (pH 8.0) and bound proteins were eluted with sonication buffer containing 300 mM imidazole, and dialyzed overnight at 4° C. against sonication buffer without imidazole.

In addition to the NLS function, N123 also contains the specific DNA-binding domain of SB, as tested in a mobility-shift assay (FIG. 3B). A 300 bp EcoRI/HindIII fragment of pT comprising the left inverted repeat of the element was end-labeled using $[\alpha^{32}P]dCTP$ and Klenow. Nucleoprotein complexes were formed in 20 mM HEPES (pH 7.5), 0.1 mM EDTA, 0.1 mg/ml BSA, 150 mM NaCl, 1 mM DTT in a total volume of 10 µl. Reactions contained 100 pg labeled probe, 2 µg poly[dI][dC] and 1.5 µl N123. After 15 min incubation on ice, 5 µl of loading dye containing 50% glycerol and bromophenol blue was added and the samples loaded onto a 5% polyacrylamide gel (Ausubel). DNaseI footprinting was done using a kit from BRL according to the recommendations of the manufacturer. Upon incubation of a radiolabeled 300-bp DNA fragment comprising the left IR of T, deoxyribonucleoprotein complexes were observed (FIG. 3B, left panel-lane 3), as compared to samples containing extracts of bacteria transformed with the expression vector only (lane 2) or probe without any protein (lane 1). Unlabelled IR sequences of T, added in excess to the reaction as competitor DNA, inhibited binding of the probe (lane 4), whereas the analogous region of a cloned Tdr1 element from zebrafish did not appreciably compete with binding (lane 5). Thus, N123 is able to distinguish between salmonid-type and zebrafish-type TcE substrates.

Figure 4A:
FIG. 4(A) is a photograph of a DNase I footprinting gel containing a 500-fold dilution of the N123 preparation shown in lane 4 of FIG. 3A using the same transposon inverted repeat DNA probe as in FIG. 3B. Reactions were run in the absence (lane 3) or presence (lane 2) of N123. Maxam-Gilbert sequencing of purine bases in the same DNA was used as a marker (lane 1).
Figure 4B:
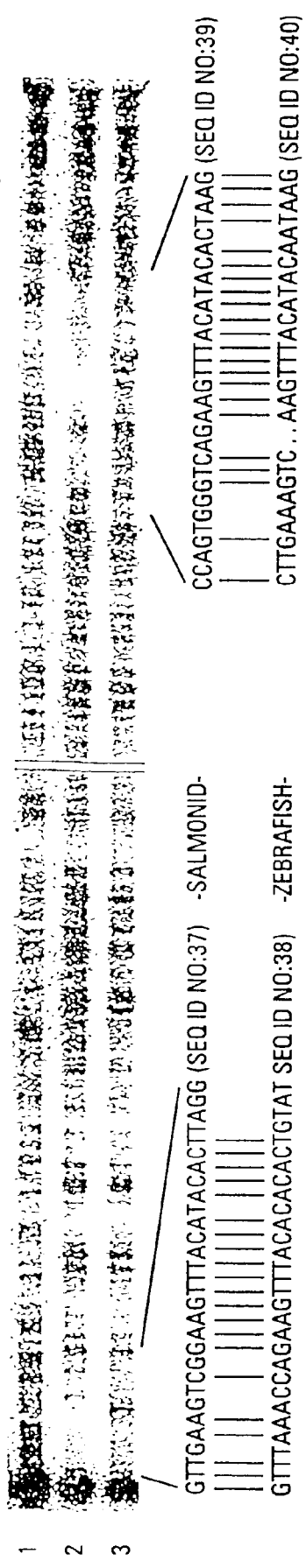
FIG. 4(B) provides a sequence comparison of the salmonid transposase-binding sites illustrated in Panel A with the corresponding sequences (SEQ ID NOS:37–40) in the zebrafish Tdr1 elements.

The number of the deoxyribonucleoprotein complexes detected by the mobility-shift assay at increasingly higher N123 concentrations indicated two protein molecules bound per IR (FIG. 3B, right panel), consistent with either two binding sites for transposase within the IR or a transposase dimer bound to a single site. Transposase-binding sites were further analyzed and mapped in a DNaseI footprinting experiment. Using the same fragment of T as above, two protected regions close to the ends of the IR probe were observed (FIG. 4). The two 30-bp footprints cover the subterminal DR motifs within the IRs. Thus, the DRs are the core sequences for DNA-binding by N123. The DR motifs are almost identical between salmonid- and zebrafish-type TcEs (Ivics et al., 1997). However, the 30-bp transposase binding-sites are longer than the DR motifs and contain 8 base pairs and 7 base pairs in the outer and internal binding sites, respectively, that are different between the zebrafish- and the salmonid-type IRs (FIG. 4B).

Figure 4C:
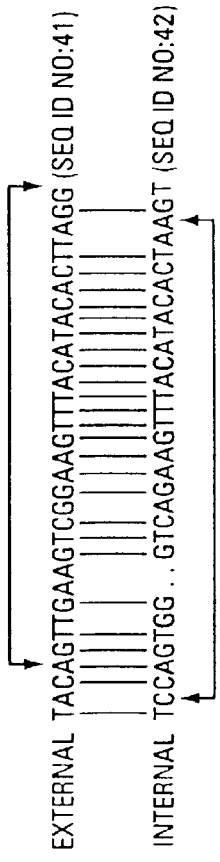
FIG. 4(C) is a sequence comparison (SEQ ID NOS:41–42) between the outer and internal transposase-binding sites in the SB transposons.

Although there are two binding-sites for transposase near the ends of each IR, apparently only the outer sites are utilized for DNA cleavage and thus excision of the transposon. Sequence comparison shows that there is a 3-bp difference in composition and a 2-bp difference in length between the outer and internal transposase-binding sites (FIG. 4C). In summary, our synthetic transposase protein has DNA-binding activity and this binding appears to be specific for salmonid-type IR/DR sequences.

For the expression of an N-terminal derivative of SB transposase, a gene segment of SB8 was PCR-amplified using primers FTC-Start and FTC-8, 5'-phosphorylated with T4 polynucleotide kinase, digested with BamHI, filled in with Klenow, and cloned into the NdeI/EcoRI digested expression vector pET21a (Novagen) after Klenow fill-in. This plasmid, pET21a/N123 expresses the first 123 amino acids of the transposase (N123) with a C-terminal histidine tag.

Example 4

Transposition of DNA by an SB Transposase

The following experiments demonstrate that the synthetic, salmonid-type SB transposase performed all of the complex steps of transposition, i.e., recognized a DNA molecule, excised the substrate DNA and inserted it into the DNA of a cell, such as a cell chromosome. This is in contrast to control samples that did not include the SB transposase and therefore measured integration through non-homologous recombination.

Figure 7A:
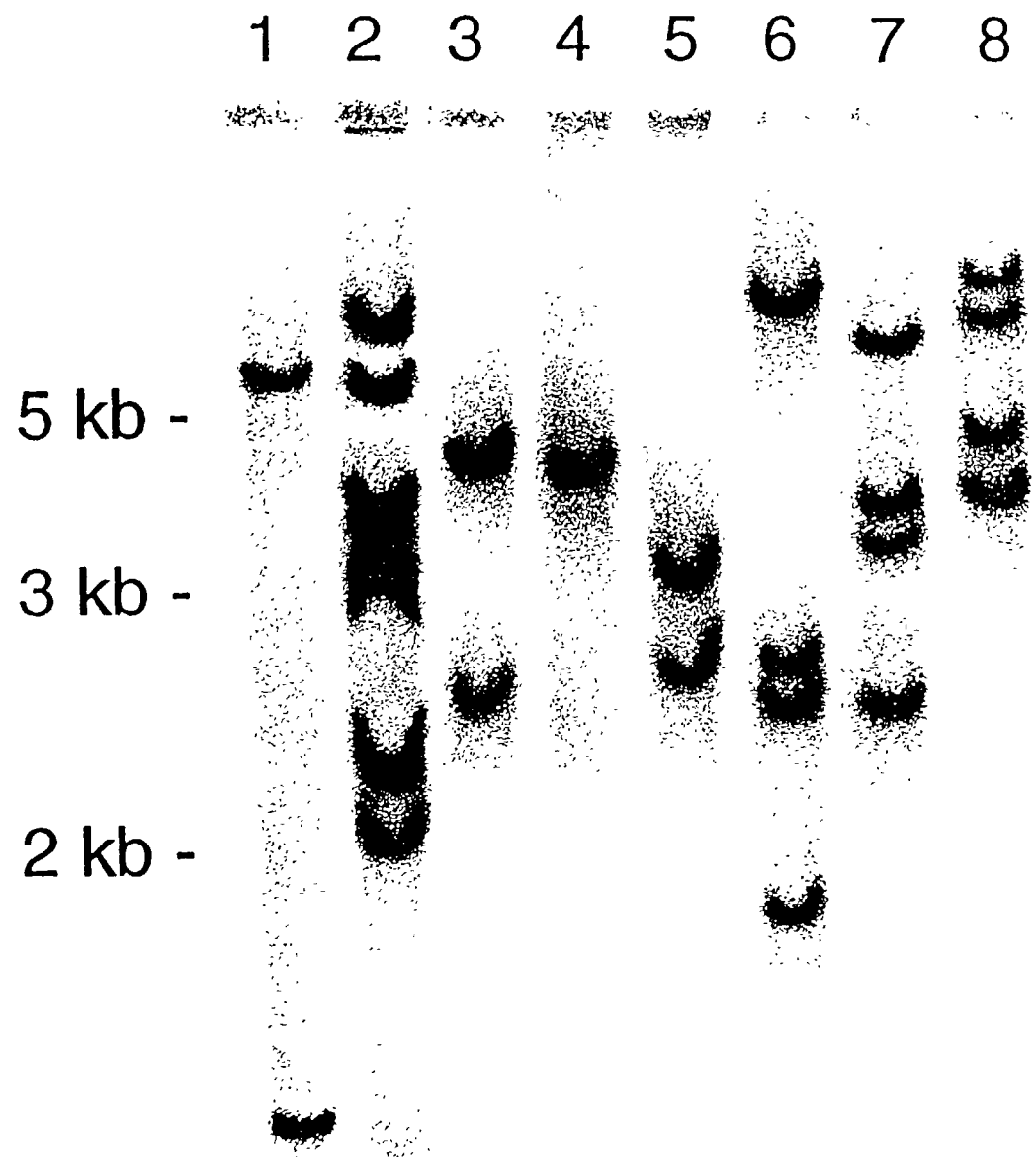
FIG. 7(A) illustrates the results of a southern hybridization of HeLa cell genomic DNA with neomycin-specific radiolabeled probe from 8 individual HeLa cell clones that had been cotransfected with pT/neo and pSB10 and survived G418 selection. Genomic DNA was digested with the restriction enzymes NheI, XhoI, BglII, SpeI and XbaI, enzymes that do not cut within the neo-marked transposon, prior to agarose gel electrophoresis and blotting.

Upon cotransfection of the two-component SB transposon system into cultured vertebrate cells, transposase activity manifested as enhanced integration of the transgene serving as the DNA substrate for transposase. The binding of transposase to a donor construct and subsequent active transport of these nucleoprotein complexes into the nuclei of transfected cells could have resulted in elevated integration rates, as observed for transgenic zebrafish embryos using an SV40 NLS peptide (Collas et al., 1996 Transgenic Res. 5, 451–458). However, DNA-binding and nuclear targeting activities alone did not increase transformation frequency, which occurred only in the presence of full-length transposase. Although not sufficient, these functions are probably necessary for transposase activity. Indeed, a single amino acid replacement in the NLS of mariner is detrimental to overall transposase function (Lohe et al., 1997 Proc. Natl. Acad. Sci. USA 94, 1293–1297). The inability of SB6, a mutated version of the transposase gene, to catalyze transposition demonstrates the importance of the sequences of the conserved motifs. Notably, three of the 11 amino acid substitutions that SB6 contains, F(21), N(28) and H(31) are within the specific DNA-binding domain (FIGS. 1 and 2). Sequence analysis of the paired-like DNA-binding domain of fish TcE transposases indicates that an isoleucine at position 28 is conserved between the transposases and the corresponding positions in the Pax proteins (Ivics et al., 1996, supra). Thus, this motif is probably crucial for DNA-binding activity. SB exhibits substrate-dependence for specific recognition and integration; only those engineered transposons that have both of the terminal inverted repeats can be transposed by SB. Similarly, in P element transformation in *Drosophila,* the transposase-producing helper construct is often a "wings-clipped" transposase gene which lacks one of the inverted repeats of P which prevents the element from jumping (Cooley et al., 1988 Science 239, 1121–1128). In our transient assay, transposition can only occur if both components of the SB system are present in the same cell. Once that happens, multiple integrations can take place as demonstrated by the finding of up to 11 integrated transgenes in neomycin-resistant cell clones (FIG. 7A). In contrast to spontaneous integration of plasmid DNA in cultured mammalian cells that often occurs in the form of concatemeric multimers into a single genomic site (Perucho et al., 1980 Cell 22, 309–317), these multiple insertions appear to have occurred in distinct chromosomal locations.

Integration of the synthetic, salmonid transposons was observed in fish as well as in mouse and human cells. In addition, recombination of genetic markers in a plasmid-to-plasmid transposition assay (Lampe et al., 1996, supra) was significantly enhanced in microinjected zebrafish embryos in the presence of transposase. Consequently, SB apparently does not need any obvious, species-specific factor that would restrict its activity to its original host. Importantly, the most significant enhancement, about 20-fold, of transgene integration was observed in human cells as well as fish embryonic cells.

Integration Activity of SB

In addition to the abilities to enter nuclei and specifically bind to its sites of action within the inverted repeats, a fully active transposase is expected to excise and integrate transposons. In the C-terminal half of the SB transposase, three protein motifs make up the DD(34)E catalytic domain; the two invariable aspartic acid residues, D(153) and D(244), and a glutamic acid residue, E(279), the latter two being separated by 34 amino acids (FIG. 2). An intact DD(34)E box is essential for catalytic functions of Tc1 and Tc3 transposases (van Luenen et al., 1994 Cell 79, 293–301; Vos and Plasterk, 1994, supra).

Figure 5A:
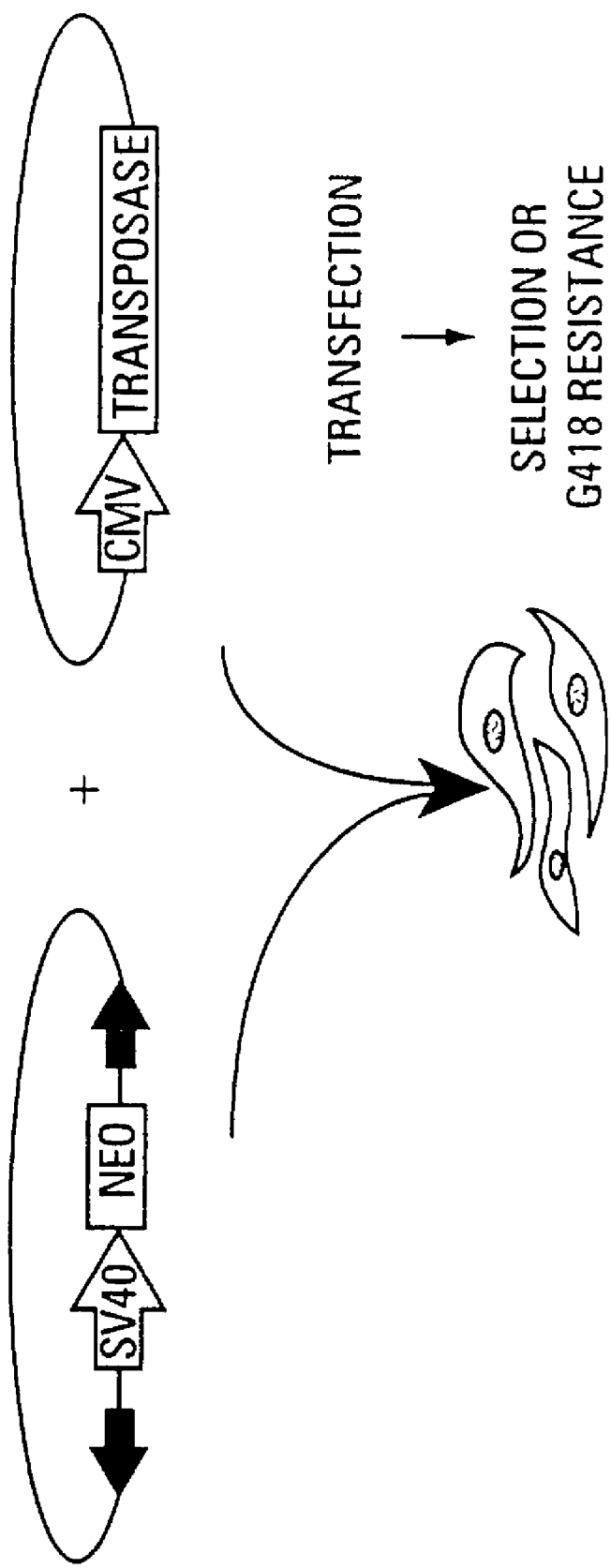
FIG. 5(A) is a schematic illustrating the genetic assay strategy for SB-mediated transgene integration in cultured cells.
Figure 5B:
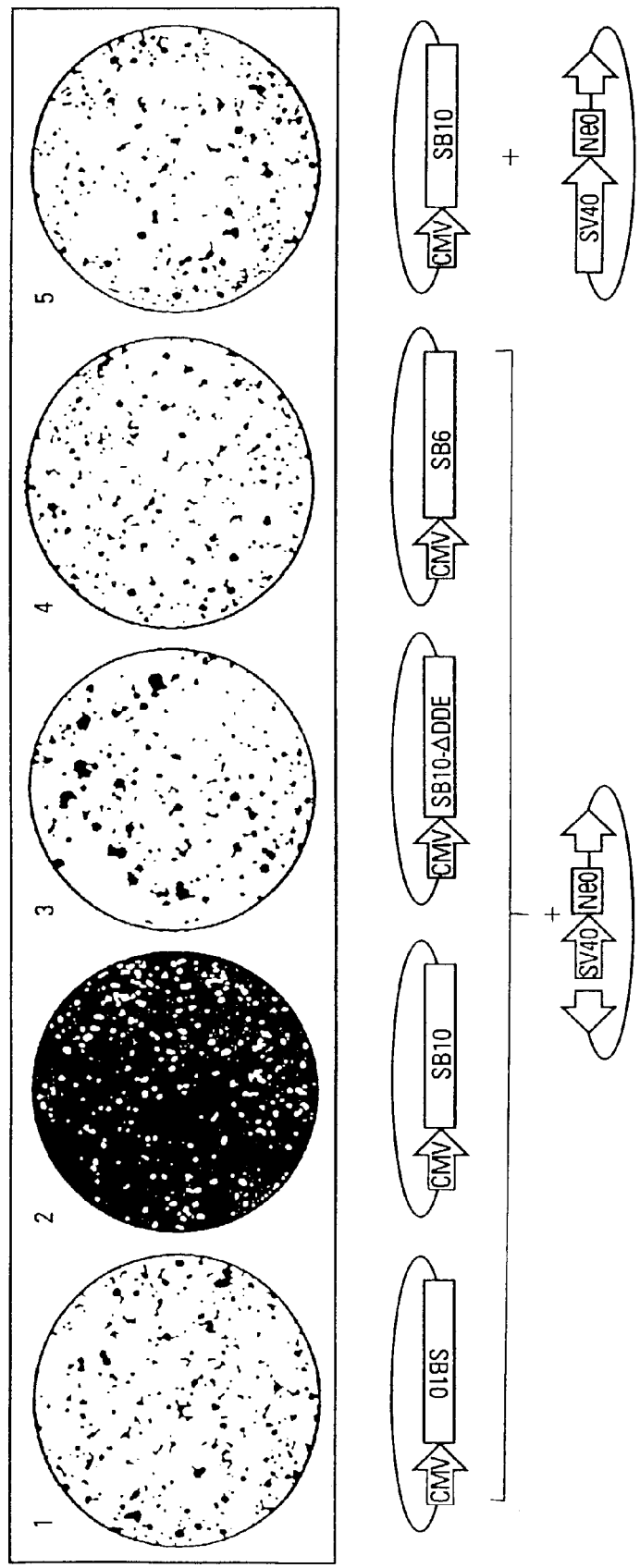
FIG. 5(B) demonstrates HeLa cell integration using Petri dishes of HeLa cells with stained colonies of G418-resistant HeLa cells that were transfected with different combinations of donor and helper plasmids. Plate: 1) pT/neo plus pSB10-AS; 2) pT/neo plus pSB10; 3) pT/neo plus pSB10-ΔDDE; 4) pT/neo plus pSB6; 5) pT/neo-ΔIR plus pSB10.
Figure 6:
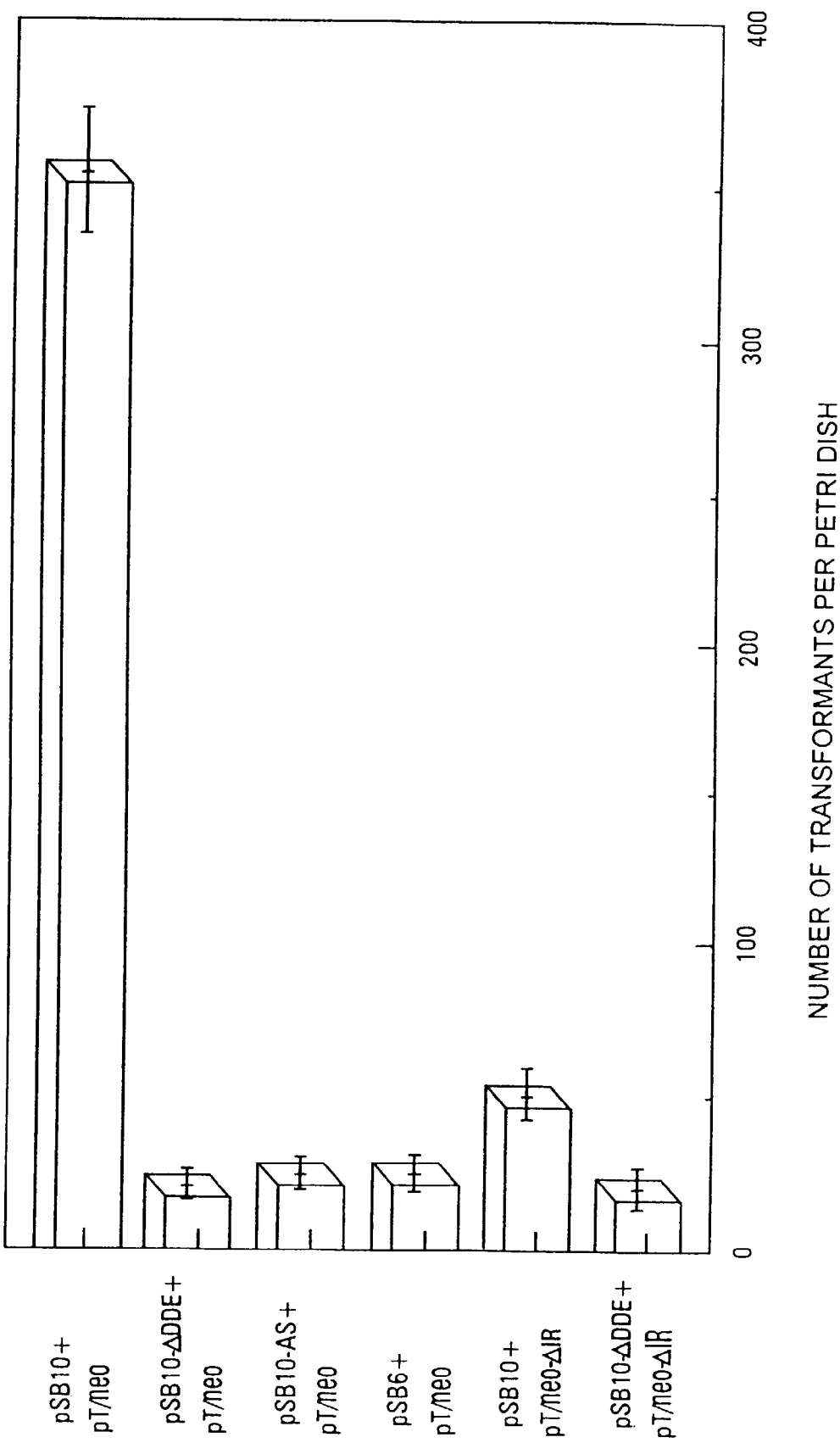
FIG. 6 summarizes the results of transgene integration in human HeLa cells. Integration was dependent on the presence of an active SB transposase and a transgene flanked by transposon inverted repeats. Different combinations of the indicated donor and helper plasmids were cotransfected into cultured HeLa cells and one tenth of the cells, as compared to the experiments shown in FIG. 5, were plated under selection to count transformants. The efficiency of transgene integration was scored as the number of transformants surviving antibiotic selection. Numbers of transformants at right represent the numbers of G418-resistant cell colonies per dish. Each column represents the average obtained from three transfection experiments.

Two different integration assays were used. A first assay was designed to detect chromosomal integration events into the chromosomes of cultured cells. The assay is based on trans-complementation of two nonautonomous transposable elements, one containing a selectable marker gene (donor) and another that expresses the transposase (helper) (FIG. 5A). The donor, pT/neo, is an engineered, T-based element which contains an SV40 promoter-driven neo gene flanked by the terminal IRs of the transposon containing binding sites for the transposase. The helper construct expresses the full-length SB10 transposase gene driven by a human cytomegalovirus (CMV) enhancer/promoter. In the assay, the donor plasmid is cotransfected with the helper or control constructs into cultured vertebrate cells, and the number of cell clones that are resistant to the neomycin analog drug G418 due to chromosomal integration and expression of the neo transgene serves as an indicator of the efficiency of gene transfer. If SB is not strictly host-specific, transposition should also occur in phylogenetically distant vertebrate species. Using the assay system shown in FIG. 5A, enhanced levels of transgene integration were observed in the presence of the helper plasmid; more than 5-fold in mouse LMTK cells and more than 20-fold in human HeLa cells (FIGS. 5B and 6). Consequently, SB appears to be able to increase the efficiency of transgene integration, and this activity is not restricted to fish cells.

To analyze the requirements for enhanced transgene integration, further experiments were conducted. FIG. 5B shows five plates of transfected HeLa cells that were placed under G418 selection, and were stained with methylene blue two weeks post-transfection. The staining patterns clearly demonstrate a significant increase in integration of neo-marked transposons into the chromosomes of HeLa cells when the SB transposase-expressing helper construct was cotransfected (plate 2), as compared to a control cotransfection of the donor plasmid plus the SB transposase gene cloned in an antisense orientation (pSB10-AS; plate 1). This result indicates that the production of transposase protein was essential for enhanced chromosomal integration of the transgene and demonstrates that the transposase is precise even in human cells.

Figure 8:
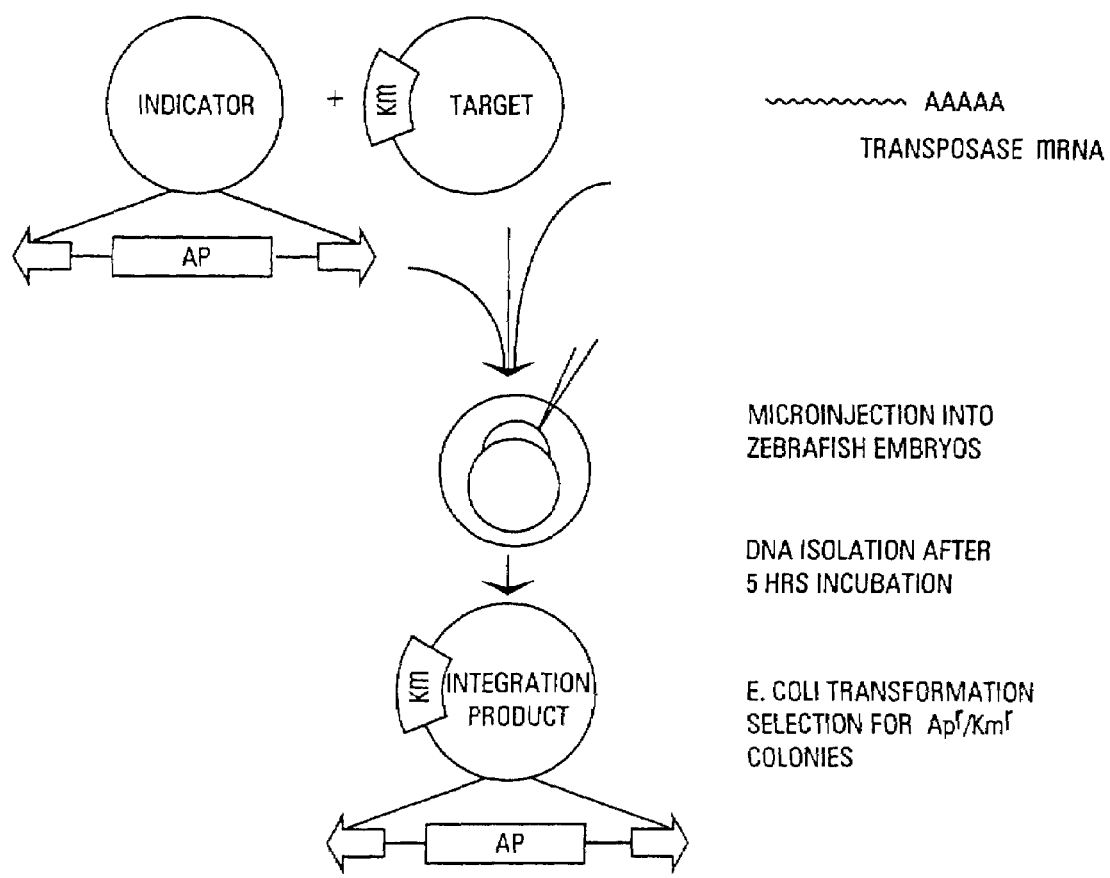
FIG. 8 is a schematic demonstrating an interplasmid assay for excision and integration of a transposon. The assay was used to evaluate transposase activity in zebrafish embryos. Two plasmids plus an RNA encoding an SB transposase protein were coinjected into the one-cell zebrafish embryo. One of the plasmids had an ampicillin resistance gene (Ap) flanked by IR/DR sequences (black arrows) recognizable by the SB transposase. Five hours after fertilization and injection, low molecular weight DNA was isolated from the embryos and used to transform E. coli. The bacteria were grown on media containing ampicillin and kanamycin (Km) to select for bacteria harboring single plasmids containing both the Km and Ap antibiotic-resistance markers. The plasmids from doubly resistant cells were examined to confirm that the Ap-transposon was excised and reintegrated into the Km target plasmid. Ap-transposons that moved into either another indicator Ap-plasmid or into the zebrafish genome were not scored. Because the amount of DNA in injected plasmid was almost equal to that of the genome, the number of integrations of Ap-transposons into target plasmids should approximate the number of integrations into the genome.

In a second assay, an indicator plasmid containing the transposase recognition sequence and a marker gene (ampicillin resistance) was co-injected with a target plasmid containing a kanamycin gene and SB transposase. Resulting plasmids were isolated and used to transform *E. coli*. Colonies were selected for ampicillin and kanamycin resistance (see FIG. 8). While SB transposase was co-microinjected in these assays, mRNA encoding the SB transposase could also be co-microinjected in place of or in addition to, the SB transposase protein.

Cell Transfections

Cells were cultured in DMEM supplemented with 10% fetal bovine serum, seeded onto 6 cm plates one day prior to transfection and transfected with 5 μg Elutip (Schleicher and Schuell)-purified plasmid DNA using Lipofectin from BRL. After 5 hrs of incubation with the DNA-lipid complexes, the cells were "glycerol-shocked" for 30 sec with 15% glycerol in phosphate buffered saline (PBS), washed once with PBS and then refed with serum-containing medium. Two days post-transfection, the transfected cells were trypsinized, resuspended in 2 ml of serum-containing DMEM and either 1 ml or 0.1 ml aliquots of this cell suspension were seeded onto several 10 cm plates in medium containing 600 μg/ml G418 (BRL). After two weeks of selection, cell clones were either picked and expanded into individual cultures or fixed with 10% formaldehyde in PBS for 15 min, stained with methylene blue in PBS for 30 min, washed extensively with deionized water, air dried and photographed.

These assays can also be used to map transposase domains necessary for chromosomal integration. For this assay, a frame shift mutation was introduced into the SB transposase gene which put a translational stop codon behind G(161). This construct, pSB10-ΔDDE, expresses a truncated transposase polypeptide that contains specific DNA-binding and NLS domains, but lacks the catalytic domain. The transformation rates obtained using this construct (plate 3 in FIG. 5B) were similar to those obtained with the antisense control (FIG. 6). This result suggests that the presence of a full-length transposase protein is necessary and that DNA-binding and nuclear transport activities themselves are not sufficient for the observed enhancement of transgene integration.

As a further control of transposase requirement, the integration activity of an earlier version of the SB transposase gene was tested, SB6 which differs from SB10 at 11 residues, FIG. 1B), using the same assay. The number of transformants observed using SB6 (plate 4 in FIG. 5B) was about the same as with the antisense control experiment (FIG. 6), indicating that the amino acid replacements that we introduced into the transposase gene were critical for transposase function. In summary, the three controls shown in plates 1, 3, and 4 of FIG. 5B establish the trans-requirements of enhanced, SB-mediated transgene integration.

True transposition requires a transposon with intact IR sequences. One of the IRs of the neo-marked transposon substrate was removed, and the performance of this construct, pT/neo-ΔIR, was tested for integration. The transformation rates observed with this plasmid (plate 5 in FIG. 5B) were more than 7-fold lower than those with the full-length donor (FIG. 6). These results indicated that both of the IRs flanking the transposon are required for efficient transposition and thereby establish some of the cis-requirements of the two-component SB transposon system.

To examine the structures of integrated transgenes, eleven colonies of cells growing under G418 selection from an experiment similar to that shown in plate 2 in FIG. 5B were picked and their DNAs analyzed using Southern hybridization. Genomic DNA samples of the cell clones were digested with a combination of five restriction enzymes that do not cut within the 2233 bp T/neo marker transposon, and hybridized with a neo-specific probe (FIG. 7). The hybridization patterns indicated that all of the analyzed clones contained integrated transgenes in the range of 1 (lane 4) to 11 (lane 2) copies per transformant. Moreover, many of the multiple insertions appear to have occurred in different locations in the human genome.

Figure 7B:
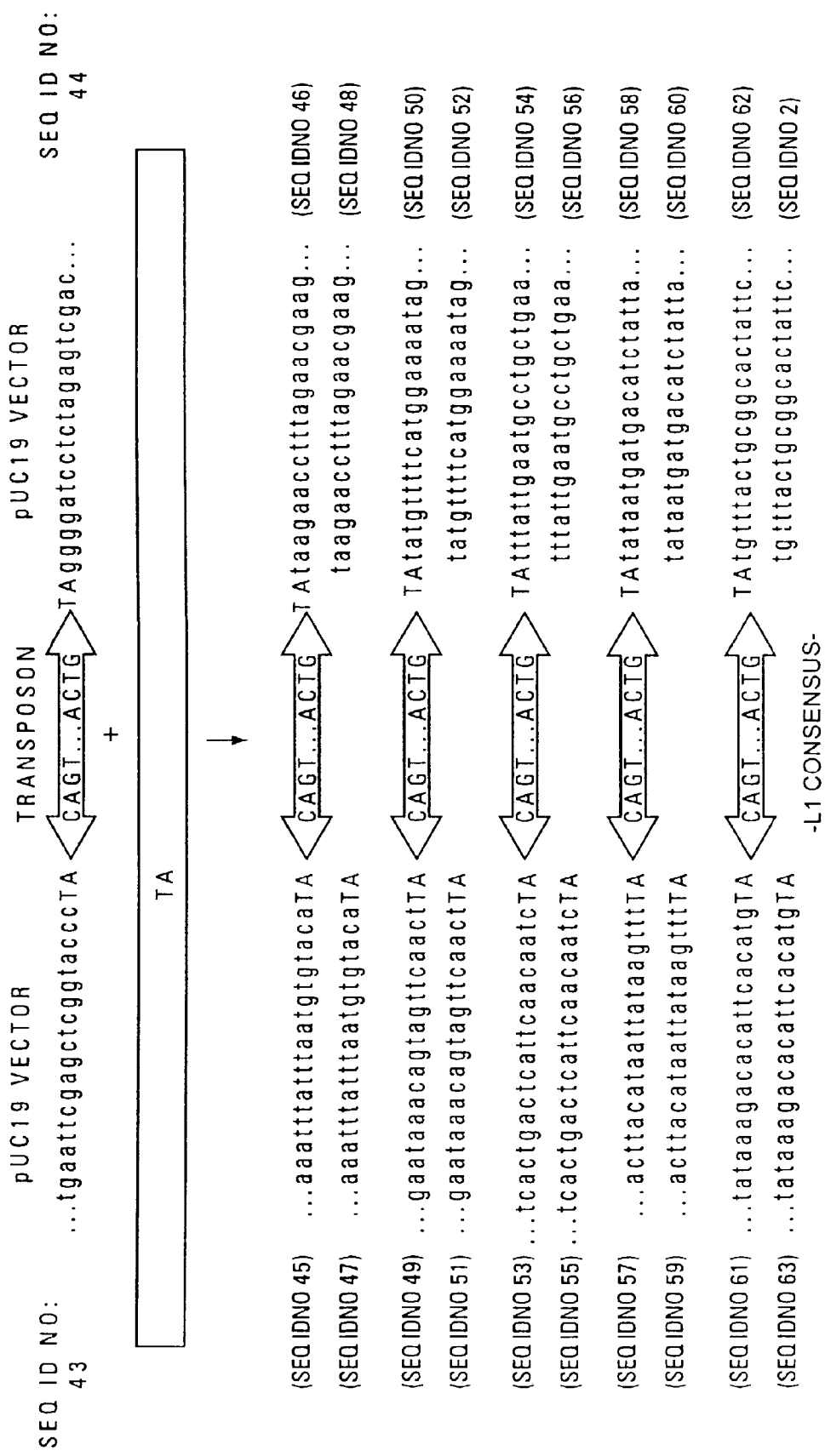
FIG. 7(B) is a diagram of the junction sequences of T/neo transposons integrated into human genomic DNA. The donor site is illustrated on top with plasmid vector sequences that originally flanked the transposon (black arrows) in pT/neo (SEQ ID NOS:43–44). Human genomic DNA serving as target for transposon insertion is illustrated as a white box containing the base pairs TA, i.e., the site of DNA integration mediated by the SB transposase. IR sequences and the flanking TA base pairs are uppercase, and the flanking genomic sequences are in lowercase (SEQ ID NOS:45–63. and SEQ ID NO:2).

The presence of duplicated TA sequences flanking an integrated transposon is a hallmark of TcE transposition. To reveal such sequences, junction fragments of integrated transposons and human genomic DNA were isolated using a ligation-mediated PCR assay (Devon et al., *Nucl. Acids. Res.*, 23, 1644–1645 (1995), Izsvak, et al., *BioTechniques*, 15, 814–816 (1993)). Junction fragments of five integrated transposons were cloned and sequenced. All of them showed the predicted sequences of the IRs which continue with TA dinucleotides and sequences that are different in all of the junctions and different from the plasmid vector sequences originally flanking the transposon in pT/neo (FIG. 7B). The same results were obtained from nine additional junctions containing either the left or the right IR of the transposon (data not shown). These results indicated that the marker transposons had been precisely excised from the donor plasmids and subsequently spliced into various locations in human chromosomes. Next, the junction sequences were compared to the corresponding "empty" chromosomal regions cloned from wild-type HeLa DNA. As shown in FIG. 7B, all of these insertions had occurred into TA target sites, which were subsequently duplicated to result in TA's flanking the integrated transposons. These data demonstrate that SB uses the same, cut-and-paste-type mechanism of transposition as other members of the Tc1/mariner superfamily and that fidelity of the reaction is maintained in heterologous cells. These data also suggest that the frequency of SB-mediated transposition is at least 15-fold higher than random recombination. Since none of the sequenced recombination events were mediated by SB-transposase, the real rate of transposition over random recombination could be many fold higher. If the integration is the result of random integration that was not mediated by the SB protein, the ends of the inserted neo construct would not correspond to the ends of the plasmids; there would have been either missing IR sequences and/or additional plasmid sequences that flank the transposon. Moreover, there would not have been duplicated TA base-pairs at the sites of integration.

Taken together, the dependence of excision and integration, from extra chromosomal plasmids to the chromosomes of vertebrate cells, of a complete transposon with inverted repeats at both ends by a full-length transposase enzyme demonstrates that the gene transfer system is fully functional.

Example 5

Transposition of DNA in Cells from Different Species

Host-requirements of transposase activity were assessed using five different vertebrate cells, N1H 3T3, LMTK and embryonic stem cells from mouse, HeLa cells from human and embryonic cells from the zebrafish.

An assay was designed to demonstrate that the transposase worked in a functioning set of cells (i.e., embryonic cells that were differentiating and growing in a natural environment). The assay involved inter-plasmid transfer where the transposon in one plasmid is removed and inserted into a target plasmid and the transposase construct was injected into 1-cell stage zebrafish embryos. In these experiments the Indicator (donor) plasmids for monitoring transposon excision and/or integration included: 1) a marker gene that when recovered in *E. coli* or in fish cells, could be screened by virtue of either the loss or the gain of a function, and 2) transposase-recognition sequences in the IRs flanking the marker gene. The total size of the marked transposons was kept to about 1.6 kb, the natural size of the TcEs found in teleost genomes. The transposition activity of Ts1 transposase was evaluated by co-microinjecting 200 ng/μl of Ts1 mRNA, made in vitro by T7 RNA polymerase from a Bluescript expression vector, plus about 250 ng/μl each of target and donor plasmids into 1-cell stage zebrafish embryos. Low molecular weight DNA was prepared from the embryos at about 5 hrs post-injection, transformed into *E. coli* cells, and colonies selected by replica plating on agar containing 50 μg/ml kanamycin and/or ampicillin. In these studies there was a transposition frequency into the target plasmid was about 0.041% in experimental cells as compared to 0.002% in control cells. This level did not include transpositions that occurred in the zebrafish genome. In these experiments we found that about 40% to 50% of the embryos did not survive beyond 4 days. Insertional mutagenesis studies in the mouse have suggested that the rate of recessive lethality is about 0.05 (i.e., an average of about 20 insertions will be lethal). Assuming that this rate is applicable to zebrafish, the approximate level of mortality suggests that with the microinjection conditions used in these experiments, about 20 insertions per genome, the mortality can be accounted for.

Example 6

Stable Gene Expression from SB Transposons

A transposon system will be functional for gene transfer, for such purposes as gene therapy and gene delivery to animal chromosomes for bioreactor systems, only if the delivered genes are reliably expressed. To determine the fidelity of gene expression following Sleeping Beauty transposase-mediated delivery, we co-microinjected a transposon containing the GFP (GFP) gene under the direction of an Xenopus eF1α promoter plus in vitro-synthesized mRNA encoding Sleeping Beauty transposase into 1-cell zebrafish embryos. 34 of the injected embryos, that showed some expression of GFP during embryogenesis, were allowed to grow to maturity and were mated with wild-type zebrafish. From these matings we found that 4 of the 34 fish could transfer a GFP gene to their progeny (Table 1). The expression of GFP in the offspring of these four F0 fish, identified as A, B, C, and D, was evaluated and the fish were grown up. From the original four founders, the rate of transmission of the GFP gene ranged from about 2% to 12% (Table 1), with an average of about 7%. The expression of GFP in these fish was nearly the same in all individuals in the same tissue types, suggesting that expression of the GFP gene could be revived following transmission through eggs and sperm. These data suggest that the germ-lines were mosaic for expressing GFP genes and that the expression of the genes was stable. The F1 offspring of Fish D were mated with each other. In this case we would expect about 75% transmission and we found that indeed 69/90 (77%) F2 fish expressed the GFP protein at comparable levels in the same tissues; further testimony of the ability of the SB transposon system to deliver genes that can be reliably expressed through at least two generations of animals.

TABLE 1

Stability of gene expression in zebrafish following injection of a SB transposon containing the GFP gene.

| | Expression of GFP | | |
|---|---|---|---|
| Transgenic Line | F0 | F1 | F2 |
| 34 founders | 34 (of which 4 progeny, A–D, passed on the transgene) | | |
| A | | 25/200 (12%) | |
| B | | 76/863 (9%) | |
| C | | 12/701 (2%) | |
| D | | 86/946 (10%) | 69/90 (77%) |

The numbers in the columns for fish A–D show the numbers of GFP expressing fish followed by the total number of offspring examined. The percentages of GFP-expressing offspring are given in parentheses.

Example 7

SB Transposons for Insertional Mutagenesis and Gene Discovery

Due to their inherent ability to move from one chromosomal location to another within and between genomes, transposable elements have revolutionized genetic manipulation of certain organisms including bacteria (Gonzales et al., 1996 *Vet. Microbiol.* 48, 283–291; Lee and Henk, 1996. *Vet. Microbiol.* 50, 143–148), Drosophila (Ballinger and Benzer, 1989 *Proc. Natl. Acad. Sci. USA* 86, 9402–9406; Bellen et al., 1989 *Genes Dev.* 3, 1288–1300; Spradling et al., 1995 *Proc. Natl. Acad. Sci. USA* 92, 10824–10830), *C. elegans* (Plasterk, 1995. *Meth. Cell. Biol.,* Academic Press, Inc. pp. 59–80) and a variety of plant species (Osborne and Baker, *Curr. Opin. Cell Biol,* 7, 406–413 (1995)). Transposons have been harnessed as useful vectors for transposon-tagging, enhancer trapping and transgenesis. However, the majority, if not all, animals of economic importance lack such a tool. For its simplicity and apparent ability to function in diverse organisms, SB should prove useful as an efficient vector for species in which DNA transposon technology is currently not available.

Figure 9:
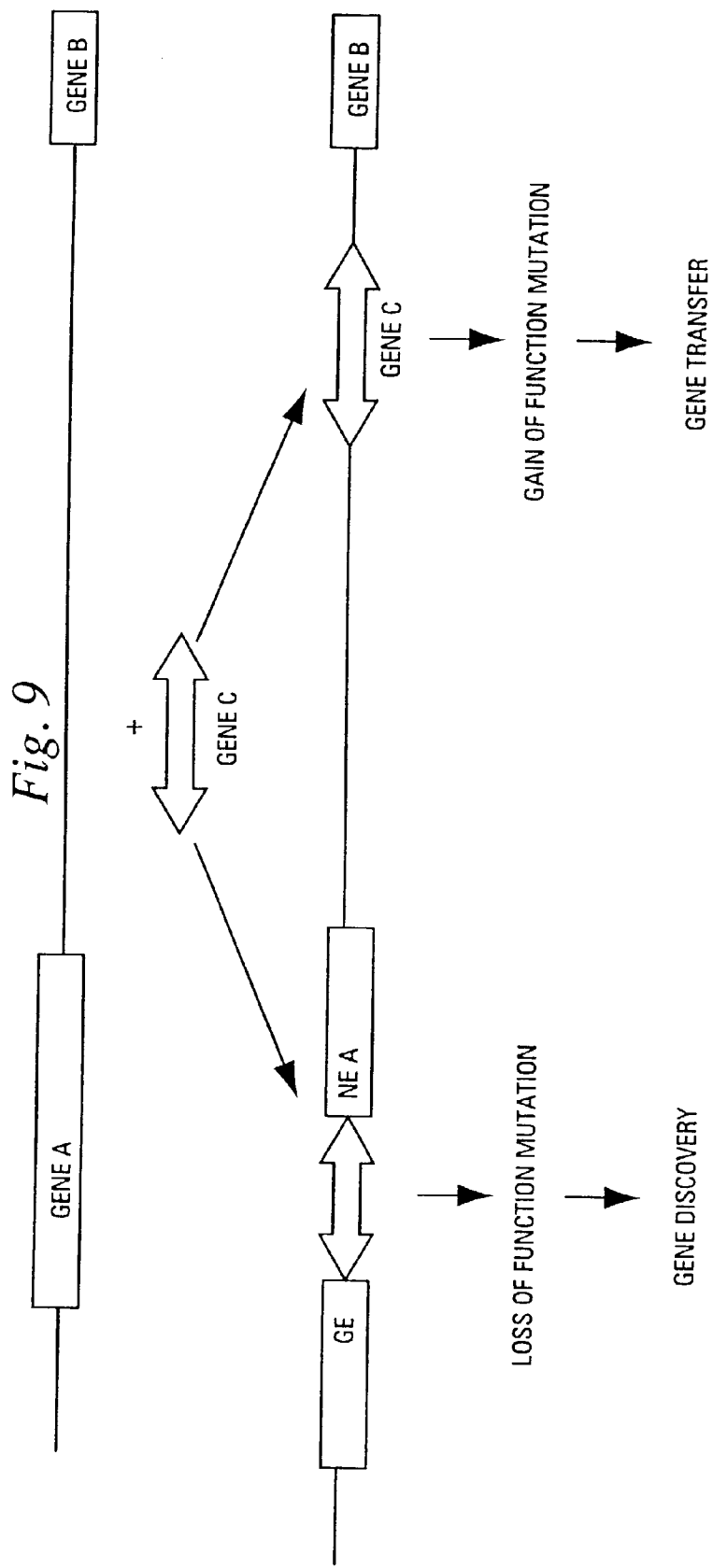
FIG. 9 illustrates two preferred methods for using the gene transfer system of this invention. Depending on the integration site of the nucleic acid fragment of this invention the effect can be either a loss-of-function or a gain-of-function mutation. Integrations, as depicted with functional coding sequences in a transposon, typically result in gain-of-function gene transfer. A subset are also a loss-of-function or gene inactivation event. Both types of activity can be exploited, for example, for gene discovery and/or functional genomics or gene delivery, i.e., human gene therapy.

An SB-type transposable element can integrate into either of two types of chromatin, functional DNA sequences where it may have a deleterious effect due to insertional mutagenesis or non-functional chromatin where it may not have much of a consequence (FIG. 9). This power of "transposon tagging" has been exploited in simpler model systems for nearly two decades (Bingham et al., *Cell,* 25, 693–704 (1981); Bellen et al., 1989, supra). Transposon tagging is an old technique in which transgenic DNA is delivered to cells so that it will integrate into genes, thereby inactivating them by insertional mutagenesis. In the process, the inactivated genes are tagged by the transposable element which then can be used to recover the mutated allele. Insertion of a transposable element may disrupt the function of a gene which can lead to a characteristic phenotype. As illustrated in FIG. 9, because insertion is approximately random, the same procedures that generate insertional, loss-of-function mutants can often be used to deliver genes that will confer new phenotypes to cells. Gain-of-function mutants can be used to understand the roles that gene products play in growth and development as well as the importance of their regulation.

There are several ways of isolating the tagged gene. In all cases genomic DNA is isolated from cells from one or more tissues of the mutated animal by conventional techniques (which vary for different tissues and animals). The DNA is cleaved by a restriction endonuclease that may or may not cut in the transposon tag (more often than not it does cleave at a known site). The resulting fragments can then either be directly cloned into plasmids or phage vectors for identification using probes to the transposon DNA (see Kim et al., 1995 for references in *Mobile Genetic Elements,* IRL Press, D. L. Sheratt eds.). Alternatively, the DNA can be PCR amplified in any of many ways; including the LM-PCR procedure of Izsvak and Ivics (1993, supra) and a modification by Devon et al. (1995, supra) and identified by its hybridization to the transposon probe. An alternative method is inverse-PCR (e.g., Allende et al., *Genes Dev.,* 10, 3141–3155 (1996)). Regardless of method for cloning, the identified clone is then sequenced. The sequences that flank the transposon (or other inserted DNA) can be identified by their non-identity to the insertional element. The sequences can be combined and then used to search the nucleic acid databases for either homology with other previously characterized gene(s), or partial homology to a gene or sequence motif that encodes some function. In some cases the gene has no homology to any known protein. It becomes a new sequence to which others will be compared. The encoded protein will be the center of further investigation of its role in causing the phenotype that induced its recovery. For gene traps and poly(A) traps, mRNA can be used to determine the nucleotide sequence of the genomic DNA flanking the inserted nucleic acid fragment. For instance, the use of sequence-specific primers that hybridize to nucleotide sequences of the inserted nucleic acid fragment that would be present in a resulting mRNA, subsequent reverse transcription and 5' or 3' RACE (rapid amplification of cDNA ends).

Example 8

SB Transposons as Markers for Gene Mapping

Figure 10A:
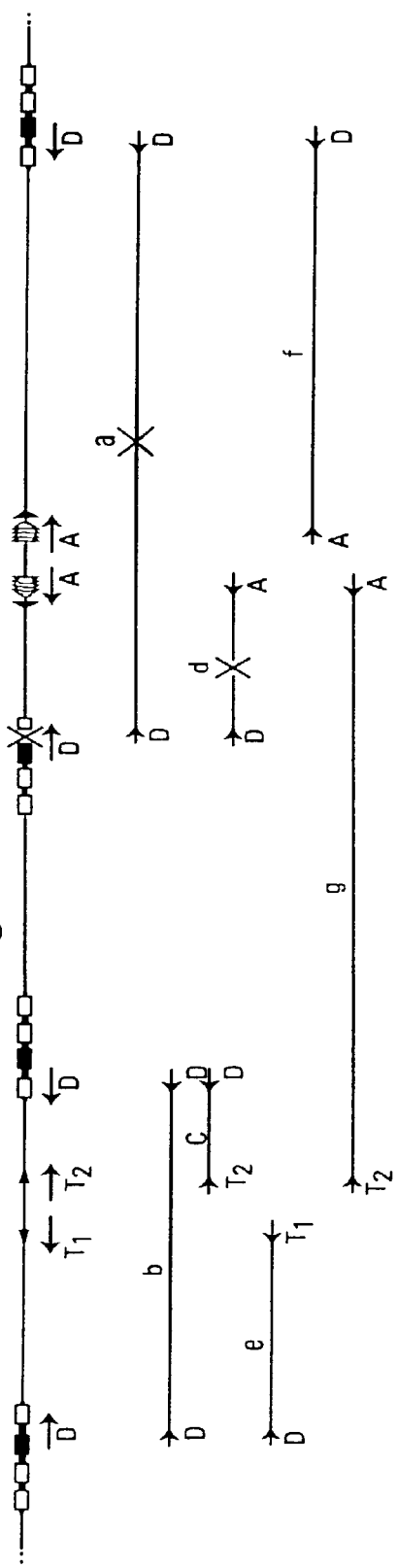
FIG. 10(A) illustrates a chromosomal region in the zebrafish genome containing the retroposon DANA (D), Tdr1 transposons ($T_1$ and $T_2$), and the highly reiterated miniature inverted-repeat transposable element Angel (A). The arrows below the elements represent specific PCR primers.

Repetitive elements for mapping transgenes and other genetic loci have also been identified. DANA is a retroposon with an unusual substructure of distinct cassettes that appears to have been assembled by insertions of short sequences into a progenitor SINE element. DANA has been amplified in the Dalnio lineage to about $4 \times 10^5$ copies/genome. Angel elements, which are nearly as abundant as DANA, are inverted-repeat sequences that are found in the vicinity of fish genes. Both DANA and Angel elements appear to be randomly distributed in the genome, and segregate in a Medelian fashion. PCR amplifications using primers specific to DANA and Angel elements can be used as genetic markers for screening polymorphisms between fish stocks and localization of transgenic sequences. Interspersed repetitive sequence-PCR (IRS-PCR) can be used to detect polymorphic DNA. IRS-PCR amplifies genomic DNA flanked by repetitive elements, using repeat-specific primers to produce polymorphic fragments that are inherited in a Medelian fashion (FIG. 10A). Primers that can be used in IRS-PCR to detect polymorphic DNA include 5'-GGC-GACRCAGTGGCGCAGTRGG (SEQ ID NO:13) where R is G or A and 5'-GAAYRTGCAAACTCCACACAGA (SEQ ID NO:14) where Y is T or C and R is G or A, each of which anneal to nucleotides present in the retroposon DANA (D); 5'-TCCATCAGACCACAGGACAT (SEQ ID NO:15) and 5'-TGTCAGGAGGAATGGGCCAAAATTC (SEQ ID NO:16), each of which anneal to nucleotides present in Tdr1 transposons; and 5'-TTTCAGTTTTGGGTGAACTATCC (SEQ ID NO:12), which anneals to nucleotides present in Angel (A) (a highly reiterated miniature inverted-repeat transposable element). Polymorphic DNA fragments can be generated by DANA or Angel specific primers in IRS-PCR and the number of detectable polymorphic bands can be significantly increased by the combination of various primers to repetitive sequences in the zebrafish genome, including SB-like transposons.

Figure 10B:
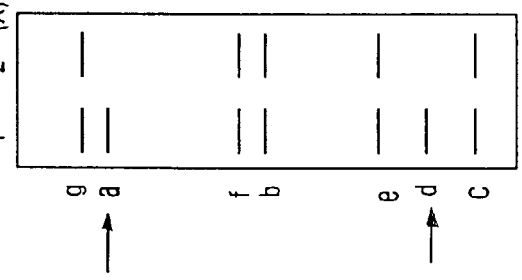
FIG. 10(B) is a schematic of the two sets of DNA amplification products from both genomes with (lane 1) and without (lane 2) the DANA element marked with an X. Note that bands "a" and "d" are missing when the marked DANA sequence is not present.

Polymorphic fragments can be recovered from gels and cloned to provide sequence tagged sites (STSs) for mapping mutations. FIG. 10B illustrates the general principles and constraints for using IRS-PCR to generate STSs. It is estimated that about 0.1% of the zebrafish genome can be directly analyzed by IRS-PCR using only 4 primers. The four conserved (C1–4) regions of DANA seem to have different degrees of conservation and representation in the zebrafish genome and this is taken into account when designing PCR primers.

The same method has a potential application in fingerprinting fish stocks and other animal populations. The method can facilitate obtaining subclones of large DNAs cloned in yeast, bacterial and bacteriophage P1-derived artificial chromosomes (YACs, BACs and PACs respectively) and can be used for the detection of integrated transgenic sequences.

Example 9

SB Transposon for Insertional Mutagenesis and Functional Analysis of Genes

I. Dicistronic Vector Construction

Dicistronic vectors in zebrafish would allow researchers to track the expression of a biological gene of interest in living embryos simply by using a reporter molecule, like GFP. Knowing where and when an introduced DNA or mRNA construct is expressed could greatly facilitate interpretation of over-expression and mutant-rescue experiments. In order for a dicistronic vector to be useful for all of these purposes, it must determined in which cells and tissues, and at what developmental stages, detectable expression of a second cistron encoding a marker gene occurs.

Accordingly, several dicistronic vectors using the EMCV IRES to determine the parameters under which a mammalian IRES could be used for dicistronic technology in zebrafish have been constructed. The EMCV IRES can function in developing zebrafish from early cleavage stages to larval stages. The products of both genes in mRNAs co-localize within the embryo, indicating that both products are made in many cell types within the embryo.

a. Methods phBeL: phBeL was constructed from component fragments of pRC/CMV (Invitrogen), pCMVβ (Clontech), pGem/eLuc, and CMV4 (Andersson et al. 1989). The vector backbone consists of the 3.15 kilobase (kb) fragment obtained after digestion with the restriction endonucleases XhoI and NotI. The XhoI to NotI fragment contains the ColE1 origin of replication, ampicillin resistance gene (amp), and CMV promoter found in the complete pRC/CMV vector. Fused to the NotI site of the pRC/CMV XhoI/NotI fragment is the 3.74-kb fragment obtained after digestion of pCMVβ with the restriction endonuclease NotI. This NotI fragment contains the complete β-galactosidase (βgal) coding region found in pCMVβ. At the NotI site after the βgal coding sequence was fused the 2.34-kb fragment obtained after digestion of pGem/eLuc with the restriction endonucleases NotI and StuI. The NotI/StuI fragment contains the EMCV IRES and luciferase coding regions. A 1.11-kb fragment of CMV4 was obtained after digestion with the restriction endonucleases SmaI and SalI. This SmaI/SalI fragment contains the human growth hormone poly(A) signal, the SV40 origin of replication, and the SV40 early enhancer/promoter region. The SmaI/SalI CMV4 fragment completes the vector since StuI and SmaI create blunt cuts while XhoI and SalI have compatible single-stranded overhangs. The hairpin structure found in the mRNA of this vector is due to the large number of restriction sites upstream of the β-galactosidase coding region due to the incorporation of partial multiple cloning sites from both pRC/CMV and pCMVβ.

pGem/eLuc: pGem/eLuc was created from component fragments of pGem Luc (Promega) and SK/EMCV IRES. The vector pGem Luc was digested with the BamHI; the single-stranded overhang left by digestion with BamHI was removed by treatment with S1 nuclease. The linearized vector was then cut by NotI which cuts within 20 base pairs of the BamHI site. SK/EMCV was digested first with XhoI and the single-stranded overhang left after digestion was removed by treatment with S1 nuclease. The linearized SK/EMCV was then digested by NotI. The 0.64-kb NotI/XhoI (S1 nuclease treated) fragment was then cloned into pGem Luc modified as above.

SK/EMCV IRES: SK/EMCV IRES was created from component fragments of pBluescriptSK- (Stratagene) and pED4 (R. J. Kaufman et al., *Nucleic Acids Res.*, 19(16), 4485–90 (1991)). pBluescriptSK- was digested by the restriction endonucleases EcoRI and XhoI, which both cut within the multiple cloning site of pBluescriptSK-. pED4 was digested with EcoRI and XhoI to obtain the 0.60-kb fragment corresponding to the EMCV IRES. The EcoRI/XhoI fragment was then ligated into pBluescriptSK- modified as above.

pBL: pBL was created from phBeL. phBeL was digested by the restriction endonucleases KpnI and NotI. The single stranded overhangs left by these restriction enzymes was then removed by treatment with S1 nuclease. The two large fragments, the 6.02-kb KpnI/KpnI fragment and the 3.47-kb NotI/NotI fragment, were ligated together. This resulted in a loss of a 70-base pair fragment within the multiple cloning site that disrupted the hairpin structure found in phBeL, and a loss of a 0.51-kb fragment corresponding to the all but 100 base pairs of the EMCV IRES.

pBeL: pBeL was made from phBeL and pBL. Both vectors were cut with the restriction endonucleases ScaI and BssHII. The ScaI recognition site is within the amp resistance gene and the BssHII recognition site is within the β-galactosidase coding region. The 7.03-kb fragment of phBeL was combined with the 2.97-kb fragment of pBL. This resulted in a loss of the hairpin structure of phBeL while maintaining the complete EMCV IRES.

pnBeG: pnBeG was constructed of component fragments of SK/nBeG(afmx) and pBL. Both vectors were digested with the restriction endonucleases SacI and XmaI. SacI cuts within the amp resistance gene and XmaI cuts just upstream of the β-galactosidase gene in either vector. The 6.67-kb XmaI/SacI fragment of SK/nBeG(afmx) was ligated to the 1.35-kb SacI/XmaI fragment of pBL. This regenerated the amp resistance gene and replaced the T7 promoter region of SK/nBeG(afmx) with the CMV/T7 promoters located within pBL. pnBeG was further optimized by PCR mutagenesis of the IRES-GFP junction to GAAAAACACGATTGCTAT <u>A<u>TG</u>GCCACA A<u>CCATGG</u>CTAGC (SEQ ID NO:64). This sequence restored wild-type EMCV IRES spacing from the polypyrimidine tract to the ATG start codon (double underline), as well as restoring the wild-type sequence around the start codon. Incorporation of an NheI restriction endonuclease site (italics) allowed a fusion with the unique NheI restriction site in the Affymax GFP (Affymax, Santa Clara, Calif.). One fusion site is four amino acids downstream of the EMCV IRES initiation codon. The fusion also recreated the NcoI restriction endonuclease site (underlined), which is found in some strains of EMCV. The Affymax GFP is a GFP that has been modified to fluoresce more than GFP. Also, the 0.56-kb MscI/EcoRI fragment of pXex-GM2 (Obtained from Shao Lin, Dept. of Biochemistry and Molecular Biology, Medical College of Georgia, Augusta, Ga.) was used to replace the 0.55-kb MscI/EcoRI fragment of pnBeG. This moved the chromophore and C-terminus of an enhanced GFP (GM2) (B. P. Cormack et al., *Gene*, 173(1 Spec No), 33–8 (1996)) into pnBeG. GM2 is a GFP that has been modified to fluoresce more than Affymax GFP. The construct with the optimal spacing between the EMCV IRES and the GM2 was named pnBeG*.

SK/nBeG(afmx): SK/nBeG(afmx) was constructed from component fragments of SK/eG(afmx) and KS/NCOnlsβgal. SK/eG(afmx) was digested with the restriction endonuclease EcoRV. This linearized the vector upstream of the EMCV IRES and Affymax GFP. KS/NCOnlsβgal was digested with the restriction endonucleases DraI and SpeI. Following this digestion, the single-stranded overhangs created by these enzymes were completely filled by using T4 polymerase. The 3.28-kb SpeI/DraI fragment, which contained a nuclear localized variant of β-galactosidase, was ligated into the EcoRV digested SK/eG(afmx). Recombinants with the β-galactosidase coding region on the same coding strand as the GFP were selected.

SK/eG(afmx): SK/eG(afmx) was created with component fragments of SK/β-globin 3'UTR 2a, SK/EMCV IRES, and pBAD-GFP (A. Crameri et al., *Nat. Biotechnol.*, 14(3), 315–9 (1996), available from Affymax). SK/β-globin 3'UTR 2a was digested with EcoRI. This linearized SK/β-globin 3'UTR 2a 5' of the *Xenopus* β-globin 3'UTR. SK/EMCV IRES was digested first with XhoI. The single-stranded overhang created by the XhoI enzyme was restored to double-stranded DNA by filling in nucleotides with Klenow polymerase. SK/EMCV IRES was then digested with EcoRI. The resultant 0.60-kb EcoRI/XhoI (filled) fragment contained the EMCV IRES. pBAD-GFP was first digested with XbaI. The single-stranded overhang created by XbaI digestion was completely filled using Klenow polymerase. The pBAD-GFP was then digested with EcoRI. The 0.73-kb XbaI/EcoRI fragment contained the complete coding region for the Affymax GFP. Successful recombinants of these three fragments have the EMCV IRES fused to the Affymax GFP upstream of the *Xenopus* β-globin 3'UTR.

SK/β-globin 3'UTR 2a: SK/β-globin 3' UTR 2a was created from component fragments of pBluescriptSK- (Stratagene) and XenB3UTR (a gift of H. Joseph Yost, Huntman Cancer Center, Univeristy of Utah, Salt Lake City, Utah). The XenB3UTR was digested with EcoRI and XbaI. The single-stranded overhang resulting from digestion with these enzymes was completely filled using Klenow polymerase. This fragment containing the Xenopus β-globin 3' UTR cDNA in the orientation from EcoRI to XbaI was cloned into the SmaI site of pBluescriptSK- (Stratagene). The recombinants with the EcoRI/XbaI fragment of the XenB3UTR in the orientation from the T7 to the T3 primer binding sites of pBluescriptSK- were SK/β-globin 3' UTR 2a.

KS/NCOnlsβgal: KS/NCOnlsβgal was constructed from component fragments of pBluescript KS-, pPD1.27 (A. Fire et al., *Gene*, 93(2), 189–98 (1990)), and a short adapter (AGCCATGGCT) (SEQ ID NO:65). pBluescript KS- was cut with XbaI and NotI. Both of these enzymes cut within the multiple cloning site of pBluescript KS- and therefore the digest results in a linearization of the pBluescript KS-. pPD1.27 was also cut with XbaI and NotI. From this digest a 3.61-kb fragment, that contained the complete coding sequence of the nuclear localized β-galactosidase and the SV40 poly(A) signal, was ligated to linearized pBluescript KS-. The resultant plasmid KS/nlsβgal was digested with XbaI. The single-stranded DNA resulting from digestion with XbaI was completely filled in using Klenow polymerase. This linearized fragment of KS/nlsβgal was then religated with the addition of an adapter (AGCCATGGCT) (SEQ ID NO:65) that contained an NcoI restriction site. This also insured a good Kozak context for the initiation codon.

Microinjection of Zebrafish. Embryos from wild-type zebrafish were obtained and maintained as described (M. Westerfield, *The Zebrafish Book*, University of Oregon Press, Eugene, Oreg. (1995)). For dicistronic mRNA injections, capped synthetic mRNA was prepared using Ambion's mMessage machine and diluted to 200 μg/ml with DEPC-treated $H_2O$ prior to injection. Purified supercoiled DNA was diluted to 50 μg/ml with $H_2O$ prior to injection.

One nanoliter of capped mRNA or DNA was injected into or just under the cytoplasm of single-cell embryos. Post-injection embryos were incubated at 28.5° C.

β-galactosidase and Luciferase Expression Levels. Embryos injected with pBeL, pBL, or phBeL mRNAs were collected in groups of five embryos at 0.5, 2, 4, 6, 8, 10, and 12 hours postinjection. The embryos were lysed with 50 µl of 1× reporter lysis buffer (Promega) and a micropestal. Embryonic lysates were stored at −80° C. prior to further analysis. Frozen lysates were thawed by hand, and microfuged at 8,000×g at 4° C. for 5 minutes. Lysates were kept on ice at all times during preparation. One embryonic equivalent (10 µl of lysate) was tested for β-galactosidase and luciferase activity. β-galactosidase and luciferase activity were measured using a Berthold Lumat LB9501 luminometer with Galacto-Light (Tropix, Bedford, Mass.) and luciferase (Promega) assay systems, respectively.

Immunohistochemistry. Embryos at various stages of development were manually dechorinated and fixed overnight at 4° C. with 4% paraformaldehyde in PBST [200 mM phosphate, 0.8% NaCl, 0.02% KCl, and 0.1% Tween-20, pH 7.3]. Batches of no more than 100 embryos were washed 8 times with immunowash solution [1% BSA, 1% DMSO in PBST] for 15 minutes at room temperature. Following washing, the embryos were incubated in immunoblock solution [5% goat serum in immunowash solution] for 3 hours. They were then incubated overnight at 4° C. in 100 µl of immunoblock solution containing a 1:1500 dilution of mouse monoclonal antibody against β-galactosidase (Boehringer-Mannheim, Indianapolis, Ind.) and a 1:40 dilution of rabbit polyclonal antibody to luciferase (Cortex Biochem, San Leandro, Calif.). The embryos were then washed and blocked as above and incubated overnight at 4° C. in 100 µl of immunoblock containing a 1:1500 dilution of FITC-conjugated goat monoclonal antibody to mouse IgG and a 1:1000 dilution of rhodamine-conjugated goat monoclonal antibody to rabbit IgG. The embryos were washed as above and mounted in 50% glycerol in PBST. Imaging was done on a BioRad MRC-1000/1024 laser scanning confocal microscope.

GFP Detection. GFP expression was visualized in manually dechorinated living embryos anesthetized with tricaine as described (Westerfield, M. *The Zebrafish Book.* University of Oregon Press. (1995)). Imaging was done on a BioRad MRC-1000/1024 laser scanning confocal microscope.

b. Results

Dicistronic Vectors and mRNAs. pBeL (FIG. 13) encodes β-galactosidase in the first cistron and luciferase in the second cistron. The two cistrons are separated by the EMCV IRES. β-galactosidase was expected to be translated by standard cap-dependent scanning whereas luciferase is expected to be translated only if the EMCV IRES directs internal initiation in a developing zebrafish. Alternatively, luciferase activity detected from pBeL could be due to leaky scanning through the β-galactosidase initiation codon or reinitiation of ribosomes at the luciferase initiation codon. To prevent these misinterpretations two dicistronic control vectors, phBeL and pBL (FIG. 13), were constructed. In phBeL, an additional sequence in the 5' UTR forms a stable hairpin structure in the mRNA that should prevent ribosomal scanning to the β-galactosidase open reading frame. If the luciferase activity observed in the test vector, pBeL, is due to leaky scanning, the luciferase activity observed in phBeL should be reduced to the same extent as the β-galactosidase expression. However, if the EMCV IRES promotes internal initiation, luciferase expression levels should be unaffected by the incorporation of a hairpin structure in the 5' UTR of phBeL. In pBL, the majority of the EMCV IRES was removed. If the luciferase activity observed in the test vector, pBeL, is from ribosomes that have translated the β-galactosidase open reading frame followed by reinitiation at the luciferase initiation codon, luciferase levels from pBL should be comparable to those in pBeL. However, if the expression of luciferase in pBeL, is due to internal initiation directed by the EMCV IRES, there should be little to no luciferase activity in pBL-injected embryos.

Figure 13:
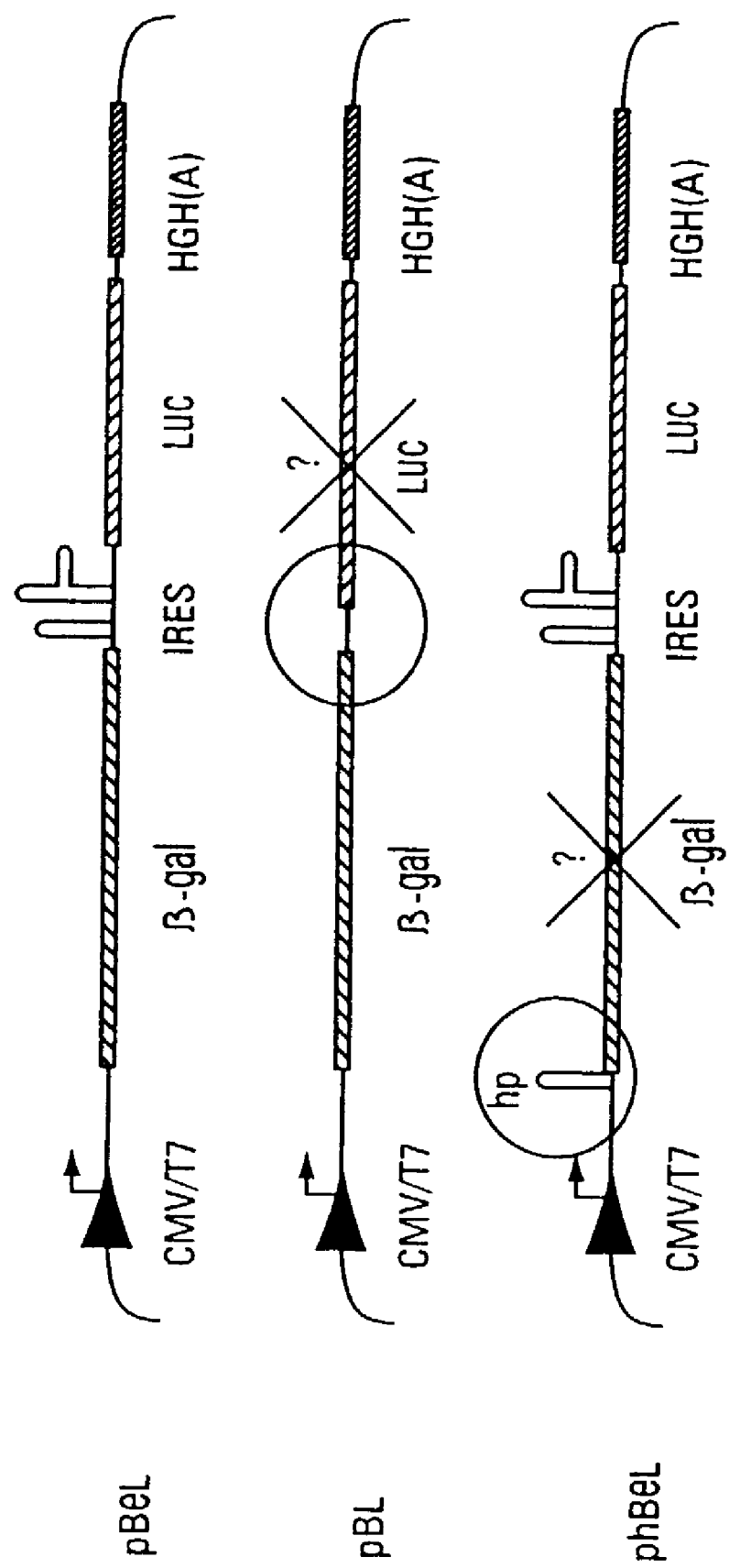
FIG. 13 illustrates the dicitronic vectors pBeL, phBeL, and pBL. The promoters are indicated by the large arrows on the left; the smaller raised arrows indicate the transcriptional initiation sites for the dicisctronic mRNAs. The IRES is depicted by a set of stem-loops. Changes in the control vectors phBeL and pBL are circled. CMV/T7, CMV/T7 promoters; β-gal, β-galactosidase coding sequence; hp, hairpin structure; Luc, luciferase coding sequence; HGH(A), human growth hormone poly(A) signal.
Figure 14:
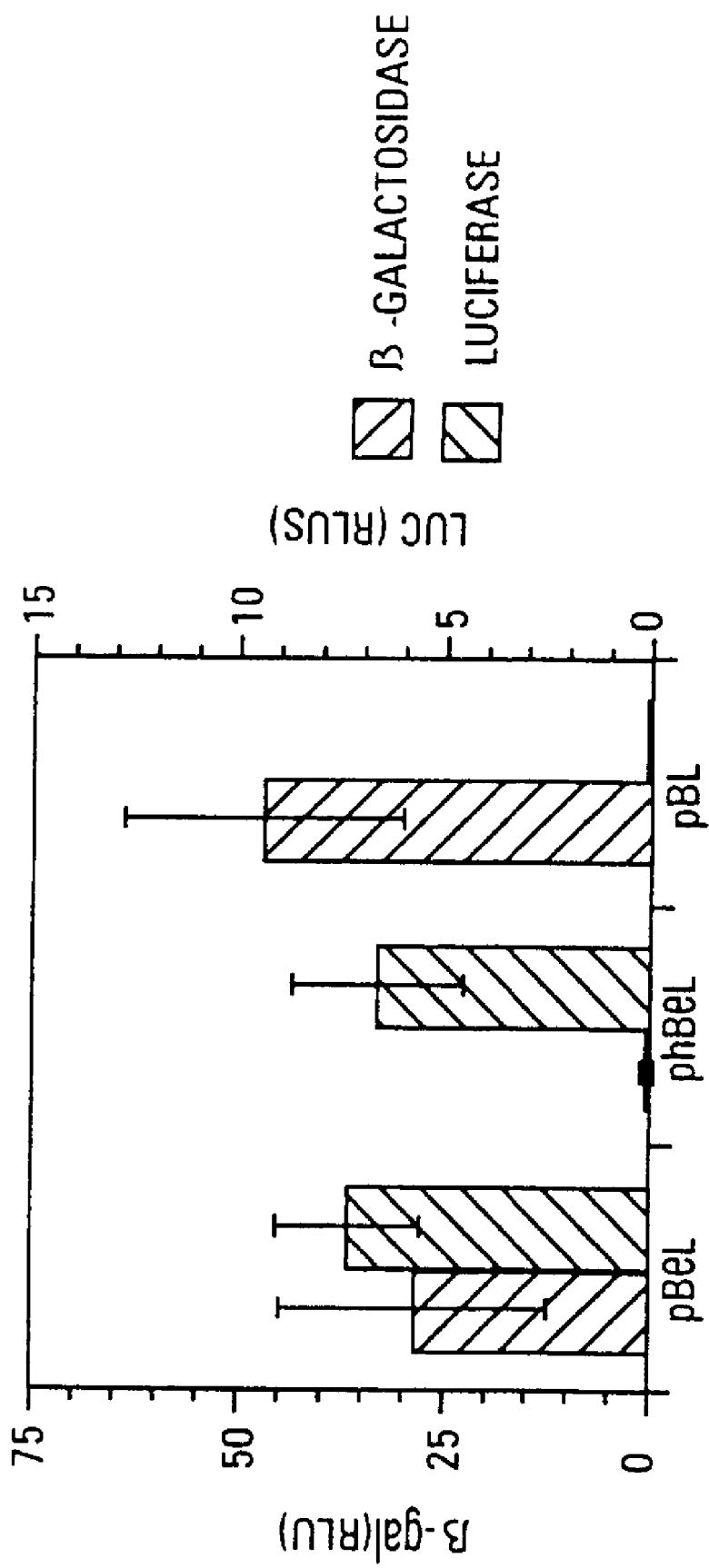
FIG. 14 The expression levels of β-galactosidase and luciferase are shown for embryos at 6 hours after injection with either pBeL, phBeL, and pBL mRNA. The error bars indicate 95% confidence intervals. Abbreviation: RLU, relative light units.

Expression from dicistronic mRNAs in zebrafish. mRNA was transcribed in vitro using the T7 promoter present in pBeL, pBL, and phBeL (FIG. 13). Shown in FIG. 14 are the β-galactosidase and luciferase activities of pBeL, phBeL, or pBL mRNA-injected embryos at 6 hours postinjection. pBeL-injected embryos expressed significant amounts of both β-galactosidase and luciferase. This was the first indication that a dicistronic message could produce protein from both of its open reading frames in developing zebrafish embryos. In phBeL-injected embryos, a hairpin structure in front of the first open reading frame, β-galactosidase, blocked its production but did not affect production of luciferase in the second cistron. Deletion of the EMCV IRES blocked the production of luciferase from the second cistron in pBL-injected embryos, but did not affect β-galactosidase production. Thus, the EMCV IRES is required for translation of luciferase from the dicistronic message pBeL in zebrafish embryos, and translation of the second cistron is not occurring by a leaky scanning or reinitiation mechanism.

Immunolocalization of Dicistronic Reporters. To determine whether or not translation of both cistrons could occur equally well in the various tissues of a developing zebrafish, β-galactosidase and luciferase were localized by immunohistochemistry. pBeL plasmid DNA was injected into or just under the cytoplasm of single cell embryos. The embryos were then fixed and immunostained. The embryos displayed highly mosaic expression patterns characteristic of DNA injections. Cells positive for β-galactosidase also stained for luciferase. Occasionally, weakly expressing cells were observed to express only one of the two reporters. Presumably this is because the luciferase expression in this cell is below the detection limits of our immunohistochemical assay since other myotomes with higher β-galactosidase expression stain quite well for luciferase. Approximately 200 fish embryos of greater than 10,000 cells each have been observed. There has been no observation of a brightly expressing cell for one reporter which did not express the other reporter.

Alternative reporters expressed from the EMCV IRES. In order to increase the functionality of dicistronic vector usage in zebrafish, the ability of the EMCV IRES to express detectable quantities of GFP was examined. GFP is a powerful reporter in the optically clear embryos of the zebrafish because it allows non-invasive analysis of expression in living embryos. Embryos injected with pnBeG DNA were examined for GFP expression at 24 hours postinjection. Although the observed GFP expression was only 5–15% of what is seen when standard monocistronic GFP expression cassettes are injected into zebrafish, its expression was readily detectable. GFP was expressed in a wide variety of cells derived from ectoderm, mesoderm, and endoderm. Expression of GFP was seen in several myotomes and cells in the blood island, which are derived from mesoderm and endoderm respectively. Several cells in the head region of a 24-hour embryo that express GFP were observed, including several ectoderm-derived cells along the dorsal edge of the hindbrain.

II. Gene-trap Vector Construction

A gene-trap transposon vector has been constructed and injected into zebrafish embryos (see, e.g., FIG. 12(A)). At least one specific cell in several embryos at approximately 28 hours post-injection tested positive for the detectable marker encoded by the gene-trap, indicating that the gene-trap had transposed into a coding sequence present in the zebrafish genome.

a. Methods pFGT/eGFP-b: pFGT/eGFP-b was formed from component fragments of pT/HB and pFV/e(nls)G. The parental vector, pT/HB, was cut with the restriction endonucleases BglII and EagI. Prior to the cloning the BglII and EagI recessed ends were completely filled in using Klenow polymerase. pFV/e(nls)G was cut with the restriction endonuclease NaeI and the fragment containing approximately the last 200 nucleotides of the carp β-actin intron 1, the EMCV IRES, GFP, and the Chinook salmon growth hormone (CSGH) poly(A) signal (otained from Dr. Choy Hew, Department of Biochemistry, Hospital for Sick Children, Toronto, Canada) was cloned into the pT/HB vector modified as above. The orientation of pFGT/eGFP-b has IR/DR (R) of the sleeping beauty transposon followed by the remnant BglII site, the 3' end of carp β-actin intron I, the EMCV IRES, GFP, the CSGH poly(A) signal, the remnant EagI site, and the IR/DR(L) of the sleeping beauty transposon.

pT/HB: pT/HB was constructed from components of pBluescript KS- (Stratagene) and pT/SVNeo (Z. Ivics et al. *Cell*, 91(4), 501–10 (1997)). pBluescript KS- was digested with the restriction endonucleases SacI and AccI; this digest removes most of the multiple cloning site found within pBluescript KS-. pT/SVNeo was also cut with SacI and AccI. This digest gave two products one of them being the SVNeo sleeping beauty transposon complete with both IR/DRs. The transposon piece was then cloned into pBluescript KS-. This vector, pT/HindIII-precursor, was then digested with the restriction endonuclease HindIII. This digest removed the internal portion of the transposon containing the SV40 promoter, neomycin resistance gene, and SV40 poly(A) signal. The remaining vector piece was ligated to create the plasmid pT/HindIII, a vector containing a single HindIII site between the IR/DRs of the sleeping beauty transposon system. pT/HindIII was then cut with XbaI. XbaI cut pT/HindIII once, and the recessed ends of this digestion were completely filled in using Klenow polymerase. The resultant fragment was then ligated to form pT/MCS-precursor. pT/MCS-precursor was then cut with HindIII. Into this vector a short double-stranded oligo was ligated to produce a multiple cloning region containing restriction endonuclease sites for HindIII, EcoRV, EcoRI, SpeI, EagI, NotII, XbaI, and BglII. pT/HB has the multiple cloning oligo inserted so that the sites go from HindIII to BglII with respect to the orientation of IR/DR(L) to IR/DR (R).

pFV/e(nls)G: pFV/e(nls)G was formed from components of pFV3 (Caldovic L., et al., *Mol. Mar. Biol. Biotechnol.*, 4, 51–61 (1995)) and pnBeG*. pFV3 was first digested by EcoRI. This linearized pFV3 just 3' of the CSGH poly(A) signal. After digestion with EcoRI, the recessed ends of pFV3 were completely filled in using Klenow polymerase. The resultant fragment was self-ligated to form pFV3ΔRI. A double-stranded oligo, FV7-MCS (CGGGGTACCGAAT-TCCCGGGTACCCCG) (SEQ ID NO:66) containing an EcoRI and SmaI sites within KpnI sites, was digested with KpnI. This oligo was then cloned into pFV3ΔRI cut with KpnI, which cuts once just after the carp β-actin intron 1. There were two products of this ligation, pFV7a and pFV7b. pFV7a has the SmaI site preceding the EcoRI site in relationship to the carp β-actin promoter, carp β-actin exon 1, carp β-actin intron 1, and the CSGH poly(A) signal. pnBeG* was then cut with EcoRI. One of the resulting fragments of this digest contained only the EMCV IRES and GFP. This fragment was then cloned into pFV7a digested with EcoRI. The product that contained the EMCV IRES and GFP in the proper orientation with respect to the fish elements (i.e. promoter, exon, intron, poly(A) signal) was named pFV/eG. pFV/eG was then digested with the restriction endonuclease NheI that cuts just after the initiation codon of GFP. Into this site a short double-stranded oligo, NLS2 (TACTCCACCAAAGAAGAGAAAGGT GGAG-GACG (SEQ ID NO:67) with CTAG 5' end overhangs), was ligated. One of the resulting products of this ligation, pFV/e(nls)G, has an additional 12 amino acids (TPP-KKRKVE DAS) (SEQ ID NO:68) encoding the SV40 nuclear localization signal.

pFGT/etTA: pFGT/etTA was formed from component fragments of pFGT/eGFP-b and pTet-Off (Clontech). The parental vector, pFGT/eGFP-b was cut with NcoI and SpeI. This digest removed the GFP and CSGH poly(A) signal from the remaining pFGT/eGFP-b vector. The tetracycline responsive transcriptional activator (tTA) of pTet-Off was PCR mutagenized to create an NcoI site at the initiator AUG using the sense primer KJC-008 (CATCCATGGCTA-GATTAGATAAAAGTAAAG TAAAG) (SEQ ID NO:69). This allowed in-frame fusion of the tTA behind the first four amino acids (MATT) (SEQ ID NO:70) of the EMCV polypeptide, insuring efficient translation from the IRES. The antisense primer KJC-009 (GCTCTAGACTAGT-GATTTTTTTCTCCATTTTAGC) (SEQ ID NO:71) incorporated a SpeI recognition site just after the SV40 poly(A) signal in the pTet-Off vector. The NcoI-tTA PCR product was cut with the restriction endonucleases NcoI and SpeI and cloned into the pFGT/eGFP-b vector modified as above.

pSBRNAX: The pSBRNAX vector was made with component fragments from SK/β-globin 3'UTR 2a and SB10 transposase (Z. Ivics et al. *Cell*, 91(4), 501–10 (1997)). SK/β-globin 3' UTR 2a was digested with the restriction endonuclease EcoRV. The SB10 transposase was amplified by polymerase chain reaction that incorporated an BamHI restriction site upstream of the SB10-coding sequence and an EcoRI restriction site downstream of the SB10-coding sequence as described by Z. Ivics et al. *Cell*, 91(4), 501–10 (1997). This fragment was digested with BamHI and EcoRI, and the resulting single-strand DNA overhangs were completely filled in using Klenow polymerase. The resulting 1.03-kb fragment was then ligated into the linearized SK/β-globin3'UTR-2a.

Microinjection of Zebrafish. Embryos from wild-type zebrafish were used for all experiments as described (M. Westerfield, *The Zebrafish Book*, University of Oregon Press, Eugene, Oreg. (1995)). For injections of gene trap vectors, 3 µl of 50 µg/ml of pFGT/eGFP-b DNA was mixed with 1 µl of 100 µg/ml Sleeping Beauty mRNA. pFGT/eGFP-b was injected as a supercoiled plasmid or as linear DNA. The linear form of pFGT/eGFP-b was obtained by digestion with the restriction endonuclease BspHI, which has two recognition sites within the vector backbone. The two resultant fragments were separated by gel electrophoresis, and the transposon containing fragment was purified using Qiagen's gel extraction kit. The Sleeping Beauty mRNA was produced using Ambion's mMessage Machine with pSBRNAX digested with NotI as template. One nanoliter of solution [37.5 µg/ml pFGT/eGFP-b and 25 µg/ml sleeping beauty mRNA] was injected into the cytoplasm or within the yolk just below the cytoplasm of 1-cell zebrafish embryos.

b. Results

Embryos were injected with linear pFGT/eGFP-b DNA and Sleeping Beauty mRNA, grown to about the 28-hour stage and illuminated with blue light. Expression of GFP in selective cells (for instance, muscle pioneer cells and myotomes) emitted a green fluorescence, indicating that the transposon had integrated into a gene that was expressed in these cells.

SEQUENCE LISTING FREE TEXT

SEQ ID NO:1; An SB transposase.
SEQ ID NO:2; Junction sequence of T/neo transposon integrated into human genomic DNA.
SEQ ID NO:3; Nucleic acid sequence encoding an SB protein.
SEQ ID NO:4–5; An inverted repeat sequence.
SEQ ID NO:6; 5' outer direct repeat.
SEQ ID NO:7; 5' inner direct repeat.
SEQ ID NO:8; 3' inner direct repeat.
SEQ ID NO:9; 3' outer direct repeat.
SEQ ID NO:10; A consensus direct repeat.
SEQ ID NO:11; A portion of a direct repeat sequence.
SEQ ID NO:12–36; Oligonucleotide primer.
SEQ ID NO:37; Salmonid transposase-binding sites.
SEQ ID NO:38; Zebrafish Tdr1 transposase-binding sites.
SEQ ID NO:39; Salmonid transposase-binding sites.
SEQ ID NO:40; Zebrafish Tdr1 transposase-binding sites.
SEQ ID NO:41; Outer transposase-binding site in SB transposon
SEQ ID NO:42; Internal transposase-binding site in SB transposon.
SEQ ID NO:43–44; Junction sequence of T/neo transposon integrated into pUC19 DNA.
SEQ ID NO:45–63; Junction sequence of T/neo transposon integrated into human genomic DNA.
SEQ ID NO:64; IRES-GFP junction in pnBeG.
SEQ ID NO:65; An adaptor.
SEQ ID NO:66–67; A double stranded oligonucleotide.
SEQ ID NO:68; SV40 nuclear localization signal.
SEQ ID NO:69; Oligonucleotide primer.
SEQ ID NO:70; Amino acids of EMCV polypeptide.
SEQ ID NO:71–75; Oligonucleotide primer.

The complete disclosures of all patents, patent applications, publications, and nucleic acid and protein database entries, including for example GenBank accession numbers and EMBL accession numbers, that are cited herein are hereby incorporated by reference as if individually incorporated. Various modifications and alterations of this invention will become apparent to those skilled in the art without departing from the scope and spirit of this invention, and it should be understood that this invention is not to be unduly limited to the illustrative embodiments set forth herein.

What is claimed is:

1. A method for identifying the function of an analyte coding sequence comprising:

(a) introducing into an isolated or cultured vertebrate cell
  i. a nucleic acid fragment comprising a nucleic acid sequence comprising (i) a detectable marker coding sequence encoding a detectable marker or a selectable marker, (ii) an analyte coding sequence located 5' of the detectable marker coding sequence and (iii) an internal ribosome entry site located therebetween, the internal ribosome entry site being operably linked to the detectable marker coding sequence, the nucleic acid fragment positioned between at least two inverted repeats that can bind to an SB protein, the inverted repeats comprising at least one direct repeat comprising a nucleic acid sequence selected from the group consisting of SEQ ID NO:6, SEQ ID NO:7, SEQ ID NO:8, SEQ ID NO:9 and SEQ ID NO:10, and wherein the SB protein comprises an amino acid sequence having at least 80% identity to SEQ ID NO:1, is capable of binding to the inverted repeat sequence of at least one of SEQ ID NO:4 and SEQ ID NO:5, and is capable of catalyzing the integration of the nucleic acid fragment into DNA in an isolated or cultured vertebrate cell; and ii. a transposase source selected from the group consisting of a transposase and a nucleic acid encoding a transposase, wherein the transposase is an SB protein;

(b) detecting the detectable marker or the selectable marker in the cell or its progeny containing the nucleic acid fragment, wherein the expression of the detectable maker or the selectable marker indicates that the nucleic acid fragment has integrated into the DNA of the cell and that the analyte coding sequence is expressed; and (c) determining whether a phenotype of the cell or its progeny containing the nucleic acid fragment is altered in comparison to a cell that does not comprise the nucleic acid fragment, wherein an altered phenotype indicates that the analyte coding sequence plays a function in the phenotype.

2. The method of claim 1 wherein the vertebrate cell is a pluripotent or totipotent vertebrate cell.

3. The method of claim 2 wherein the pluripotent or totipotent vertebrate cell is selected from the group consisting of an oocyte, a cell isolated from an embryo, an egg cell and a stem cell.

4. The method of claim 1 wherein the detectable marker is green fluorescent protein.

5. The method of claim 1 wherein the selectable marker is neomycin.

6. The method of claim 1 further comprising, prior to (b), growing the cell into an animal.

7. The method of claim 6 wherein step (c) comprises determining the phenotype of an animal.

8. The method of claim 1 wherein the analyte coding sequence is derived from a library of DNA fragments.

9. The method of claim 1 wherein the analyte coding sequence comprises a preselected coding sequence.

10. The method of claim 1 wherein the analyte coding sequence is operably linked to a promoter.

11. The method of claim 1 wherein the vertebrate cell is selected from the group consisting of a fish cell, a human cell and a mouse cell.

12. A nucleic acid fragment comprising a nucleic acid sequence comprising (i) a detectable marker coding sequence that encodes a detectable marker or a selectable marker, (ii) an analyte coding sequence located 5' of the detectable marker coding sequence and (iii) an internal ribosome entry site located therebetween and operably linked to the detectable marker coding sequence, the nucleic acid sequence positioned between at least two inverted repeats capable of binding to an SB protein, the inverted repeats comprising at least one direct repeat comprising a nucleic acid sequence selected from the group consisting of SEQ ID NO:6, SEQ ID NO:7, SEQ ID NO:8, SEQ ID NO:9 and SEQ ID NO:10, wherein the SB protein comprises an amino acid sequence having at least 80% identity to SEQ ID NO:1, is capable of binding to the inverted repeat sequence of at least one of SEQ ID NO:4 and SEQ ID NO:5, and is capable of catalyzing the integration of the nucleic acid fragment into DNA in an isolated or cultured vertebrate cell.

13. The fragment of claim 12 wherein the analyte coding sequence is derived from a library of DNA fragments.

14. The fragment of claim 12 wherein the analyte coding sequence comprises a preselected coding sequence.

15. The fragment of claim 12 wherein the analyte coding sequence is operably linked to a promoter.

16. A gene transfer system to introduce a nucleic acid sequence into the DNA of an isolated or cultured vertebrate cell comprising:
  (a) a nucleic acid fragment comprising a nucleic acid sequence comprising (i) a detectable marker coding sequence that encodes a detectable marker or a selectable marker, (ii) an analyte coding sequence located 5' of the detectable marker coding sequence and (iii) an internal ribosome entry site located therebetween and operably linked to the detectable marker coding sequence, the nucleic acid sequence positioned between at least two inverted repeats capable of binding to an SB protein, the inverted repeats comprising at least one direct repeat comprising a nucleic acid sequence selected from the group consisting of SEQ ID NO:6, SEQ ID NO:7, SEQ ID NO:8, SEQ ID NO:9 and SEQ ID NO:10, wherein the SB protein comprises an amino acid sequence having at least 80% identity to SEQ ID NO:1, is capable of binding to the inverted repeat sequence of at least one of SEQ ID NO:4 and SEQ ID NO:5, and is capable of catalyzing the integration of the nucleic acid fragment into DNA in an isolated or cultured vertebrate cell; and
  (b) a transposase source selected from the group consisting of a transposase and nucleic acid encoding a transposase, wherein the transposase is an SB protein.

17. The gene transfer system of claim 16 wherein the analyte coding sequence is derived from a library of DNA fragments.

18. The gene transfer system of claim 16 wherein the analyte coding sequence comprises a preselected coding sequence.

19. The gene transfer system of claim 16 wherein the analyte coding sequence is operably linked to a promoter.

20. The gene transfer system of claim 16, wherein the vertebrate cell is a pluripotent or totipotent vertebrate cell.

21. The gene transfer system of claim 20 wherein the pluripotent or totipotent vertebrate cell is selected from the group consisting of an oocyte, a cell isolated from an embryo, an egg cell and a stem cell.

22. The gene transfer system of claim 16, wherein the transposase source is an mRNA.

23. The gene transfer system of claim 16, wherein the transposase source is an SB transposase.

24. The gene transfer system of claim 16 or 17, wherein the transposase source is a nucleic acid encoding the transposase that is integrated into the genome of the vertebrate cell.

25. The gene transfer system of claim 16 or 17, wherein the nucleic acid fragment is part of a plasmid or a recombinant viral vector.

26. The gene transfer system of claim 16, wherein the vertebrate cell is a selected from the group consisting of a fish cell, a human cell and a mouse cell.

27. A gene transfer system to introduce a nucleic acid sequence into the DNA of a fish comprising a nucleic acid fragment comprising a nucleic acid sequence comprising an internal ribosome entry site, the nucleic acid sequence positioned between at least two inverted repeats capable of binding to an SB protein, wherein the nucleic acid fragment is capable of integrating into the genomic DNA of a fish.

28. The gene transfer system of claim 27 wherein the nucleic acid sequence further comprises a coding sequence located 3' to and operably linked to the internal ribosome entry site.

29. The gene transfer system of claim 28 wherein the coding sequence is a first coding sequence, the nucleic acid sequence further comprising a second coding sequence located 5' to both the first coding sequence and the internal ribosome entry site.

* * * * *

UNITED STATES PATENT AND TRADEMARK OFFICE
CERTIFICATE OF CORRECTION

| | |
|---|---|
| PATENT NO. | : 7,160,682 B2 |
| APPLICATION NO. | : 10/191698 |
| DATED | : January 9, 2007 |
| INVENTOR(S) | : Hackett et al. |

It is certified that error appears in the above-identified patent and that said Letters Patent is hereby corrected as shown below:

Column 1, Line 14
Delete "2RO1-RR06625-05" and insert --2R01-RR06625-05--

Signed and Sealed this

Twenty-seventh Day of March, 2007

JON W. DUDAS
*Director of the United States Patent and Trademark Office*

```
                        SEQUENCE LISTING

<160> NUMBER OF SEQ ID NOS: 75

<210> SEQ ID NO 1
<211> LENGTH: 340
<212> TYPE: PRT
<213> ORGANISM: Artificial Sequence
<220> FEATURE:
<223> OTHER INFORMATION: Description of Artificial Sequence: An SB
      transposase

<400> SEQUENCE: 1

Met Gly Lys Ser Lys Glu Ile Ser Gln Asp Leu Arg Lys Lys Ile Val
 1               5                  10                  15

Asp Leu His Lys Ser Gly Ser Ser Leu Gly Ala Ile Ser Lys Arg Leu
                20                  25                  30

Lys Val Pro Arg Ser Ser Val Gln Thr Ile Val Arg Lys Tyr Lys His
            35                  40                  45

His Gly Thr Thr Gln Pro Ser Tyr Arg Ser Gly Arg Arg Val Leu
        50                  55                  60

Ser Pro Arg Asp Glu Arg Thr Leu Val Arg Lys Val Gln Ile Asn Pro
65                  70                  75                  80

Arg Thr Thr Ala Lys Asp Leu Val Lys Met Leu Glu Glu Thr Gly Thr
                85                  90                  95

Lys Val Ser Ile Ser Thr Val Lys Arg Val Leu Tyr Arg His Asn Leu
            100                 105                 110

Lys Gly Arg Ser Ala Arg Lys Lys Pro Leu Leu Gln Asn Arg His Lys
        115                 120                 125

Lys Ala Arg Leu Arg Phe Ala Thr Ala His Gly Asp Lys Asp Arg Thr
    130                 135                 140
```

-continued

```
Phe Trp Arg Asn Val Leu Trp Ser Asp Glu Thr Lys Ile Glu Leu Phe
145                 150                 155                 160
Gly His Asn Asp His Arg Tyr Val Trp Arg Lys Gly Glu Ala Cys
                165                 170                 175
Lys Pro Lys Asn Thr Ile Pro Thr Val Lys His Gly Gly Ser Ile
            180                 185                 190
Met Leu Trp Gly Cys Phe Ala Ala Gly Gly Thr Gly Ala Leu His Lys
        195                 200                 205
Ile Asp Gly Ile Met Arg Lys Glu Asn Tyr Val Asp Ile Leu Lys Gln
    210                 215                 220
His Leu Lys Thr Ser Val Arg Lys Leu Lys Leu Gly Arg Lys Trp Val
225                 230                 235                 240
Phe Gln Met Asp Asn Asp Pro Lys His Thr Ser Lys Val Val Ala Lys
                245                 250                 255
Trp Leu Lys Asp Asn Lys Val Lys Val Leu Glu Trp Pro Ser Gln Ser
            260                 265                 270
Pro Asp Leu Asn Pro Ile Glu Asn Leu Trp Ala Glu Leu Lys Lys Arg
        275                 280                 285
Val Arg Ala Arg Arg Pro Thr Asn Leu Thr Gln Leu His Gln Leu Cys
    290                 295                 300
Gln Glu Glu Trp Ala Lys Ile His Pro Thr Tyr Cys Gly Lys Leu Val
305                 310                 315                 320
Glu Gly Tyr Pro Lys Arg Leu Thr Gln Val Lys Gln Phe Lys Gly Asn
                325                 330                 335
Ala Thr Lys Tyr
            340

<210> SEQ ID NO 2
<211> LENGTH: 20
<212> TYPE: DNA
<213> ORGANISM: Artificial Sequence
<220> FEATURE:
<223> OTHER INFORMATION: Description of Artificial Sequence: Junction
      sequence of T/neo transposon integrated into human
      genomic DNA

<400> SEQUENCE: 2
tgtttattgc ggcactattc                                              20

<210> SEQ ID NO 3
<211> LENGTH: 1023
<212> TYPE: DNA
<213> ORGANISM: Artificial Sequence
<220> FEATURE:
<223> OTHER INFORMATION: Description of Artificial Sequence: Nucleic
      acid sequence encoding an SB protein

<400> SEQUENCE: 3
atgggaaaat caaaagaaat cagccaagac ctcagaaaaa aaattgtaga cctccacaag      60
tctggttcat ccttgggagc aatttccaaa cgcctgaaag taccacgttc atctgtacaa     120
acaatagtac gcaagtataa acaccatggg accacgcagc cgtcataccg ctcaggaagg     180
agacgcgttc tgtctcctag agatgaacgt actttggtgc gaaaagtgca atcaatccc      240 agaacaacag caaaggacct tgtgaagatg ctggagaaa caggtacaaa agtatctata     300
tccacagtaa acgagtcct atatcgacat aacctgaaag gccgctcagc aaggaagaag     360
ccactgctcc aaaaccgaca taagaaagcc agactacggt ttgcaactgc acatggggac     420
aaagatcgta cttttttggag aaatgtcctc tggtctgatg aaacaaaaat agaactgttt     480
```

```
ggccataatg accatcgtta tgtttggagg aagaaggggg aggcttgcaa gccgaagaac      540
accatcccaa ccgtgaagca cggggtggc agcatcatgt tgtgggggtg ctttgctgca       600
ggagggactg gtgcacttca caaaatagat ggcatcatga ggaaggaaaa ttatgtggat      660
atattgaagc aacatctcaa gacatcagtc aggaagttaa agcttggtcg caaatgggtc     720
ttccaaatgg acaatgaccc caagcatact tccaaagttg tggcaaaatg gcttaaggac     780
aacaaagtca aggtattgga gtggccatca caaagccctg acctcaatcc tatagaaaat     840
ttgtgggcag aactgaaaaa gcgtgtgcga gcaaggaggc ctacaaacct gactcagtta     900
caccagctct gtcaggagga atgggccaaa attcacccaa cttattgtgg gaagcttgtg     960
gaaggctacc cgaaacgttt gacccaagtt aaacaattta aggcaatgc taccaaatac     1020 tag                                                                  1023

<210> SEQ ID NO 4
<211> LENGTH: 226
<212> TYPE: DNA
<213> ORGANISM: Artificial Sequence
<220> FEATURE:
<223> OTHER INFORMATION: Description of Artificial Sequence: An inverted
      repeat sequence

<400> SEQUENCE: 4
agttgaagtc ggaagtttac atacacttaa gttggagtca ttaaaactcg tttttcaact      60
acaccacaaa tttcttgtta acaaacaata gttttggcaa gtcagttagg acatctactt    120
tgtgcatgac acaagtcatt tttccaacaa ttgtttacag acagattatt tcacttataa    180
ttcactgtat cacaattcca gtgggtcaga agtttacata cactaa                    226

<210> SEQ ID NO 5
<211> LENGTH: 229
<212> TYPE: DNA
<213> ORGANISM: Artificial Sequence
<220> FEATURE:
<223> OTHER INFORMATION: Description of Artificial Sequence: An inverted
      repeat sequence

<400> SEQUENCE: 5
ttgagtgtat gttaacttct gacccactgg gaatgtgatg aaagaaataa aagctgaaat      60
gaatcattct ctctactatt attctgatat ttcacattct taaaataaag tggtgatcct    120
aactgacctt aagacaggga atctttactc ggattaaatg tcaggaattg tgaaaaagtg    180
agtttaaatg tatttggcta aggtgtatgt aaacttccga cttcaactg                 229

<210> SEQ ID NO 6
<211> LENGTH: 30
<212> TYPE: DNA
<213> ORGANISM: Artificial Sequence
<220> FEATURE:
<223> OTHER INFORMATION: Description of Artificial Sequence: 5' outer
      direct repeat

<400> SEQUENCE: 6
gttgaagtcg gaagtttaca tacacttaag                                       30

<210> SEQ ID NO 7
<211> LENGTH: 30
<212> TYPE: DNA
<213> ORGANISM: Artificial Sequence
<220> FEATURE:
<223> OTHER INFORMATION: Description of Artificial Sequence: 5' inner
```

```
                        direct repeat

<400> SEQUENCE: 7
cagtgggtca gaagtttaca tacactaagg                                        30

<210> SEQ ID NO 8
<211> LENGTH: 31
<212> TYPE: DNA
<213> ORGANISM: Artificial Sequence
<220> FEATURE:
<223> OTHER INFORMATION: Description of Artificial Sequence: 3' inner
      direct repeat

<400> SEQUENCE: 8
cagtgggtca gaagttaaca tacactcaat t                                      31

<210> SEQ ID NO 9
<211> LENGTH: 31
<212> TYPE: DNA
<213> ORGANISM: Artificial Sequence
<220> FEATURE:
<223> OTHER INFORMATION: Description of Artificial Sequence: 3' outer
      direct repeat

<400> SEQUENCE: 9
agttgaagtc ggaagtttac atacacctta g                                      31

<210> SEQ ID NO 10
<211> LENGTH: 30
<212> TYPE: DNA
<213> ORGANISM: Artificial Sequence
<220> FEATURE:
<223> OTHER INFORMATION: Description of Artificial Sequence: A consensus
      direct repeat

<400> SEQUENCE: 10
caktgrgtcr gaagtttaca tacacttaag                                        30

<210> SEQ ID NO 11
<211> LENGTH: 8
<212> TYPE: DNA
<213> ORGANISM: Artificial Sequence
<220> FEATURE:
<223> OTHER INFORMATION: Description of Artificial Sequence: A portion
      of a direct repeat sequence

<400> SEQUENCE: 11 acatacac                                                                 8

<210> SEQ ID NO 12
<211> LENGTH: 23
<212> TYPE: DNA
<213> ORGANISM: Artificial Sequence
<220> FEATURE:
<223> OTHER INFORMATION: Description of Artificial Sequence:
      Oligonucleotide primer

<400> SEQUENCE: 12
tttcagtttt gggtgaacta tcc                                               23

<210> SEQ ID NO 13
<211> LENGTH: 22
<212> TYPE: DNA
<213> ORGANISM: Artificial Sequence
<220> FEATURE:
<223> OTHER INFORMATION: Description of Artificial Sequence:
      Oligonucleotide primer
```

<400> SEQUENCE: 13
ggcgacrcag tggcgcagtr gg                                    22

<210> SEQ ID NO 14
<211> LENGTH: 22
<212> TYPE: DNA
<213> ORGANISM: Artificial Sequence
<220> FEATURE:
<223> OTHER INFORMATION: Description of Artificial Sequence:
      Oligonucleotide primer

<400> SEQUENCE: 14
gaayrtgcaa actccacaca ga                                    22

<210> SEQ ID NO 15
<211> LENGTH: 20
<212> TYPE: DNA
<213> ORGANISM: Artificial Sequence
<220> FEATURE:
<223> OTHER INFORMATION: Description of Artificial Sequence:
      Oligonucleotide primer

<400> SEQUENCE: 15
tccatcagac cacaggacat                                       20

<210> SEQ ID NO 16
<211> LENGTH: 25
<212> TYPE: DNA
<213> ORGANISM: Artificial Sequence
<220> FEATURE:
<223> OTHER INFORMATION: Description of Artificial Sequence:
      Oligonucleotide primer

<400> SEQUENCE: 16
tgtcaggagg aatgggccaa aattc                                 25

<210> SEQ ID NO 17
<211> LENGTH: 21
<212> TYPE: DNA
<213> ORGANISM: Artificial Sequence
<220> FEATURE:
<223> OTHER INFORMATION: Description of Artificial Sequence:
      Oligonucleotide primer

<400> SEQUENCE: 17
cctctaggat ccgacatcat g                                     21

<210> SEQ ID NO 18
<211> LENGTH: 28
<212> TYPE: DNA
<213> ORGANISM: Artificial Sequence
<220> FEATURE:
<223> OTHER INFORMATION: Description of Artificial Sequence:
      Oligonucleotide primer

<400> SEQUENCE: 18
tctagaattc tagtatttgg tagcattg                              28

<210> SEQ ID NO 19
<211> LENGTH: 26
<212> TYPE: DNA
<213> ORGANISM: Artificial Sequence
<220> FEATURE:
<223> OTHER INFORMATION: Description of Artificial Sequence:
      Oligonucleotide primer

```
<400> SEQUENCE: 19
aacaccatgg gaccacgcag ccgtca                                          26

<210> SEQ ID NO 20
<211> LENGTH: 30
<212> TYPE: DNA
<213> ORGANISM: Artificial Sequence
<220> FEATURE:
<223> OTHER INFORMATION: Description of Artificial Sequence:
      Oligonucleotide primer

<400> SEQUENCE: 20
caggttatgt cgatatagga ctcgttttac                                      30

<210> SEQ ID NO 21
<211> LENGTH: 30
<212> TYPE: DNA
<213> ORGANISM: Artificial Sequence
<220> FEATURE:
<223> OTHER INFORMATION: Description of Artificial Sequence:
      Oligonucleotide primer

<400> SEQUENCE: 21
ccttgctgag cggcctttca ggttatgtcg                                      30

<210> SEQ ID NO 22
<211> LENGTH: 18
<212> TYPE: DNA
<213> ORGANISM: Artificial Sequence
<220> FEATURE:
<223> OTHER INFORMATION: Description of Artificial Sequence:
      Oligonucleotide primer

<400> SEQUENCE: 22
ttgcactttt cgcaccaa                                                   18

<210> SEQ ID NO 23
<211> LENGTH: 21
<212> TYPE: DNA
<213> ORGANISM: Artificial Sequence
<220> FEATURE:
<223> OTHER INFORMATION: Description of Artificial Sequence:
      Oligonucleotide primer

<400> SEQUENCE: 23
gtacctgttt cctccagcat c                                               21

<210> SEQ ID NO 24
<211> LENGTH: 18
<212> TYPE: DNA
<213> ORGANISM: Artificial Sequence
<220> FEATURE:
<223> OTHER INFORMATION: Description of Artificial Sequence:
      Oligonucleotide primer

<400> SEQUENCE: 24
gagcagtggc ttcttcct                                                   18

<210> SEQ ID NO 25
<211> LENGTH: 18
<212> TYPE: DNA
<213> ORGANISM: Artificial Sequence
<220> FEATURE:
<223> OTHER INFORMATION: Description of Artificial Sequence:
      Oligonucleotide primer

<400> SEQUENCE: 25
```
ccacaacatg atgctgcc                                                18

<210> SEQ ID NO 26
<211> LENGTH: 21
<212> TYPE: DNA
<213> ORGANISM: Artificial Sequence
<220> FEATURE:
<223> OTHER INFORMATION: Description of Artificial Sequence:
      Oligonucleotide primer

<400> SEQUENCE: 26
tggccactcc aataccttga c                                            21

<210> SEQ ID NO 27
<211> LENGTH: 31
<212> TYPE: DNA
<213> ORGANISM: Artificial Sequence
<220> FEATURE:
<223> OTHER INFORMATION: Description of Artificial Sequence:
      Oligonucleotide primer

<400> SEQUENCE: 27
acactctaga ctagtatttg gtagcattgc c                                 31

<210> SEQ ID NO 28
<211> LENGTH: 22
<212> TYPE: DNA
<213> ORGANISM: Artificial Sequence
<220> FEATURE:
<223> OTHER INFORMATION: Description of Artificial Sequence:
      Oligonucleotide primer

<400> SEQUENCE: 28
gtgcttcacg gttgggatgg tg                                           22

<210> SEQ ID NO 29
<211> LENGTH: 26
<212> TYPE: DNA
<213> ORGANISM: Artificial Sequence
<220> FEATURE:
<223> OTHER INFORMATION: Description of Artificial Sequence:
      Oligonucleotide primer

<400> SEQUENCE: 29
attttctata ggattgaggt cagggc                                       26

<210> SEQ ID NO 30
<211> LENGTH: 35
<212> TYPE: DNA
<213> ORGANISM: Artificial Sequence
<220> FEATURE:
<223> OTHER INFORMATION: Description of Artificial Sequence:
      Oligonucleotide primer

<400> SEQUENCE: 30
gtctggttca tccttgggag caatttccaa acgcc                             35

<210> SEQ ID NO 31
<211> LENGTH: 30
<212> TYPE: DNA
<213> ORGANISM: Artificial Sequence
<220> FEATURE:
<223> OTHER INFORMATION: Description of Artificial Sequence:
      Oligonucleotide primer

<400> SEQUENCE: 31
caaaaccgac ataagaaagc cagactacgg                                    30

<210> SEQ ID NO 32
<211> LENGTH: 44
<212> TYPE: DNA
<213> ORGANISM: Artificial Sequence
<220> FEATURE:
<223> OTHER INFORMATION: Description of Artificial Sequence:
      Oligonucleotide primer

<400> SEQUENCE: 32
accatcgtta tgtttggagg aagaaggggg aggcttgcaa gccg                    44

<210> SEQ ID NO 33
<211> LENGTH: 36
<212> TYPE: DNA
<213> ORGANISM: Artificial Sequence
<220> FEATURE:
<223> OTHER INFORMATION: Description of Artificial Sequence:
      Oligonucleotide primer

<400> SEQUENCE: 33
ggcatcatga ggaaggaaaa ttatgtggat atattg                             36

<210> SEQ ID NO 34
<211> LENGTH: 29
<212> TYPE: DNA
<213> ORGANISM: Artificial Sequence
<220> FEATURE:
<223> OTHER INFORMATION: Description of Artificial Sequence:
      Oligonucleotide primer

<400> SEQUENCE: 34
ctgaaaaagc gtgtgcgagc aaggaggcc                                     29

<210> SEQ ID NO 35
<211> LENGTH: 27
<212> TYPE: DNA
<213> ORGANISM: Artificial Sequence
<220> FEATURE:
<223> OTHER INFORMATION: Description of Artificial Sequence:
      Oligonucleotide primer

<400> SEQUENCE: 35
gtggaaggct acccgaaacg tttgacc                                       27

<210> SEQ ID NO 36
<211> LENGTH: 30
<212> TYPE: DNA
<213> ORGANISM: Artificial Sequence
<220> FEATURE:
<223> OTHER INFORMATION: Description of Artificial Sequence:
      Oligonucleotide primer

<400> SEQUENCE: 36
gacaaagatc gtactttttg gagaaatgtc                                    30

<210> SEQ ID NO 37
<211> LENGTH: 30
<212> TYPE: DNA
<213> ORGANISM: Artificial Sequence
<220> FEATURE:
<223> OTHER INFORMATION: Description of Artificial Sequence: Salmonid
      transposase-binding sites

<400> SEQUENCE: 37
gttgaagtcg gaagtttaca tacacttagg                                    30

<210> SEQ ID NO 38
<211> LENGTH: 30
<212> TYPE: DNA
<213> ORGANISM: Artificial Sequence
<220> FEATURE:
<223> OTHER INFORMATION: Description of Artificial Sequence: Zebrafish
      Tdr1 transposase-binding sites

<400> SEQUENCE: 38
gtttaaacca gaagtttaca cacactgtat                                     30

<210> SEQ ID NO 39
<211> LENGTH: 30
<212> TYPE: DNA
<213> ORGANISM: Artificial Sequence
<220> FEATURE:
<223> OTHER INFORMATION: Description of Artificial Sequence:  Salmonid
      transposase-binding sites

<400> SEQUENCE: 39
ccagtgggtc agaagtttac atacactaag                                     30

<210> SEQ ID NO 40
<211> LENGTH: 28
<212> TYPE: DNA
<213> ORGANISM: Artificial Sequence
<220> FEATURE:
<223> OTHER INFORMATION: Description of Artificial Sequence: Zebrafish
      Tdr1 transposase-binding sites

<400> SEQUENCE: 40
cttgaaagtc aagtttacat acaataag                                       28

<210> SEQ ID NO 41
<211> LENGTH: 34
<212> TYPE: DNA
<213> ORGANISM: Artificial Sequence
<220> FEATURE:
<223> OTHER INFORMATION: Description of Artificial Sequence: Outer
      transposase-binding site in SB transposon

<400> SEQUENCE: 41
tacagttgaa gtcggaagtt tacatacact tagg                                34

<210> SEQ ID NO 42
<211> LENGTH: 32
<212> TYPE: DNA
<213> ORGANISM: Artificial Sequence
<220> FEATURE:
<223> OTHER INFORMATION: Description of Artificial Sequence: Internal
      transposase-binding site in SB transposon

<400> SEQUENCE: 42
tccagtgggt cagaagttta catacactaa gt                                  32

<210> SEQ ID NO 43
<211> LENGTH: 26
<212> TYPE: DNA
<213> ORGANISM: Artificial Sequence
<220> FEATURE:
<223> OTHER INFORMATION: Description of Artificial Sequence: Junction
      sequence of T/neo transposon integrated into pUC19
      DNA

<400> SEQUENCE: 43
tgaattcgag ctcggtaccc tacagt                                         26

<210> SEQ ID NO 44
<211> LENGTH: 26
<212> TYPE: DNA
<213> ORGANISM: Artificial Sequence
<220> FEATURE:
<223> OTHER INFORMATION: Description of Artificial Sequence: Junction
      sequence of T/neo transposon integrated into pUC19
      DNA

<400> SEQUENCE: 44
actgtagggg atcctctaga gtcgac                                    26

<210> SEQ ID NO 45
<211> LENGTH: 26
<212> TYPE: DNA
<213> ORGANISM: Artificial Sequence
<220> FEATURE:
<223> OTHER INFORMATION: Description of Artificial Sequence: Junction
      sequence of T/neo transposon integrated into human
      genomic DNA

<400> SEQUENCE: 45
aaatttattt aatgtgtaca tacagt                                    26

<210> SEQ ID NO 46
<211> LENGTH: 26
<212> TYPE: DNA
<213> ORGANISM: Artificial Sequence
<220> FEATURE:
<223> OTHER INFORMATION: Description of Artificial Sequence: Junction
      sequence of T/neo transposon integrated into human
      genomic DNA

<400> SEQUENCE: 46
actgtataag aacctttaga acgaag                                    26

<210> SEQ ID NO 47
<211> LENGTH: 22
<212> TYPE: DNA
<213> ORGANISM: Artificial Sequence
<220> FEATURE:
<223> OTHER INFORMATION: Description of Artificial Sequence: Junction
      sequence of T/neo transposon integrated into human
      genomic DNA

<400> SEQUENCE: 47
aaatttattt aatgtgtaca ta                                        22

<210> SEQ ID NO 48
<211> LENGTH: 20
<212> TYPE: DNA
<213> ORGANISM: Artificial Sequence
<220> FEATURE:
<223> OTHER INFORMATION: Description of Artificial Sequence: Junction
      sequence of T/neo transposon integrated into human
      genomic DNA

<400> SEQUENCE: 48
taagaacctt tagaacgaag                                           20

<210> SEQ ID NO 49
<211> LENGTH: 26
<212> TYPE: DNA
<213> ORGANISM: Artificial Sequence
<220> FEATURE:
<223> OTHER INFORMATION: Description of Artificial Sequence: Junction
      sequence of T/neo transposon integrated into human genomic DNA

<400> SEQUENCE: 49
gaataaacag tagttcaact tacagt                                          26

<210> SEQ ID NO 50
<211> LENGTH: 26
<212> TYPE: DNA
<213> ORGANISM: Artificial Sequence
<220> FEATURE:
<223> OTHER INFORMATION: Description of Artificial Sequence: Junction
      sequence of T/neo transposon integrated into human
      genomic DNA

<400> SEQUENCE: 50
actgtatatg ttttcatgga aaatag                                          26

<210> SEQ ID NO 51
<211> LENGTH: 22
<212> TYPE: DNA
<213> ORGANISM: Artificial Sequence
<220> FEATURE:
<223> OTHER INFORMATION: Description of Artificial Sequence: Junction
      sequence of T/neo transposon integrated into human
      genomic DNA

<400> SEQUENCE: 51
gaataaacag tagttcaact ta                                              22

<210> SEQ ID NO 52
<211> LENGTH: 20
<212> TYPE: DNA
<213> ORGANISM: Artificial Sequence
<220> FEATURE:
<223> OTHER INFORMATION: Description of Artificial Sequence: Junction
      sequence of T/neo transposon integrated into human
      genomic DNA

<400> SEQUENCE: 52
tatgttttca tggaaaatag                                                 20

<210> SEQ ID NO 53
<211> LENGTH: 26
<212> TYPE: DNA
<213> ORGANISM: Artificial Sequence
<220> FEATURE:
<223> OTHER INFORMATION: Description of Artificial Sequence: Junction
      sequence of T/neo transposon integrated into human
      genomic DNA

<400> SEQUENCE: 53
tcactgactc attcaacatc tacagt                                          26

<210> SEQ ID NO 54
<211> LENGTH: 26
<212> TYPE: DNA
<213> ORGANISM: Artificial Sequence
<220> FEATURE:
<223> OTHER INFORMATION: Description of Artificial Sequence: Junction
      sequence of T/neo transposon integrated into human
      genomic DNA

<400> SEQUENCE: 54
actgtattta ttgaatgcct gctgaa                                          26

<210> SEQ ID NO 55
<211> LENGTH: 22

```
<212> TYPE: DNA
<213> ORGANISM: Artificial Sequence
<220> FEATURE:
<223> OTHER INFORMATION: Description of Artificial Sequence: Junction
      sequence of T/neo transposon integrated into human
      genomic DNA

<400> SEQUENCE: 55
tcactgactc attcaacatc ta                                           22

<210> SEQ ID NO 56
<211> LENGTH: 20
<212> TYPE: DNA
<213> ORGANISM: Artificial Sequence
<220> FEATURE:
<223> OTHER INFORMATION: Description of Artificial Sequence: Junction
      sequence of T/neo transposon integrated into human
      genomic DNA

<400> SEQUENCE: 56
tttattgaat gcctgctgaa                                              20

<210> SEQ ID NO 57
<211> LENGTH: 26
<212> TYPE: DNA
<213> ORGANISM: Artificial Sequence
<220> FEATURE:
<223> OTHER INFORMATION: Description of Artificial Sequence: Junction
      sequence of T/neo transposon integrated into human
      genomic DNA

<400> SEQUENCE: 57
acttacataa ttataagttt tacagt                                       26

<210> SEQ ID NO 58
<211> LENGTH: 26
<212> TYPE: DNA
<213> ORGANISM: Artificial Sequence
<220> FEATURE:
<223> OTHER INFORMATION: Description of Artificial Sequence: Junction
      sequence of T/neo transposon integrated into human
      genomic DNA

<400> SEQUENCE: 58
actgtatata atgatgacat ctatta                                       26

<210> SEQ ID NO 59
<211> LENGTH: 22
<212> TYPE: DNA
<213> ORGANISM: Artificial Sequence
<220> FEATURE:
<223> OTHER INFORMATION: Description of Artificial Sequence: Junction
      sequence of T/neo transposon integrated into human
      genomic DNA

<400> SEQUENCE: 59
acttacataa ttataagttt ta                                           22

<210> SEQ ID NO 60
<211> LENGTH: 20
<212> TYPE: DNA
<213> ORGANISM: Artificial Sequence
<220> FEATURE:
<223> OTHER INFORMATION: Description of Artificial Sequence: Junction
      sequence of T/neo transposon integrated into human
      genomic DNA

<400> SEQUENCE: 60
```
tataatgatg acatctatta                                              20

<210> SEQ ID NO 61
<211> LENGTH: 26
<212> TYPE: DNA
<213> ORGANISM: Artificial Sequence
<220> FEATURE:
<223> OTHER INFORMATION: Description of Artificial Sequence: Junction
      sequence of T/neo transposon integrated into human
      genomic DNA

<400> SEQUENCE: 61
tataaagaca cattcacatg tacagt                                       26

<210> SEQ ID NO 62
<211> LENGTH: 26
<212> TYPE: DNA
<213> ORGANISM: Artificial Sequence
<220> FEATURE:
<223> OTHER INFORMATION: Description of Artificial Sequence: Junction
      sequence of T/neo transposon integrated into human
      genomic DNA

<400> SEQUENCE: 62
actgtatgtt tactgcggca ctattc                                       26

<210> SEQ ID NO 63
<211> LENGTH: 22
<212> TYPE: DNA
<213> ORGANISM: Artificial Sequence
<220> FEATURE:
<223> OTHER INFORMATION: Description of Artificial Sequence: Junction
      sequence of T/neo transposon integrated into human
      genomic DNA

<400> SEQUENCE: 63
tataaagaca catgcacacg ta                                           22

<210> SEQ ID NO 64
<211> LENGTH: 39
<212> TYPE: DNA
<213> ORGANISM: Artificial Sequence
<220> FEATURE:
<223> OTHER INFORMATION: Description of Artificial Sequence: IRES-GFP
      junction in pnBeG

<400> SEQUENCE: 64
gaaaaacacg attgctatat ggccacaacc atggctagc                         39

<210> SEQ ID NO 65
<211> LENGTH: 10
<212> TYPE: DNA
<213> ORGANISM: Artificial Sequence
<220> FEATURE:
<223> OTHER INFORMATION: Description of Artificial Sequence: An adaptor

<400> SEQUENCE: 65
agccatggct                                                         10

<210> SEQ ID NO 66
<211> LENGTH: 27
<212> TYPE: DNA
<213> ORGANISM: Artificial Sequence
<220> FEATURE:
<223> OTHER INFORMATION: Description of Artificial Sequence: A double
      standed oligonucleotide

<400> SEQUENCE: 66

```
cggggtaccg aattcccggg tacccccg                                      27
```

<210> SEQ ID NO 67
<211> LENGTH: 36
<212> TYPE: DNA
<213> ORGANISM: Artificial Sequence
<220> FEATURE:
<223> OTHER INFORMATION: Description of Artificial Sequence: A double
      standed oligonucleotide

<400> SEQUENCE: 67

```
ctagtactcc accaaagaag agaaaggtgg aggacg                             36
```

<210> SEQ ID NO 68
<211> LENGTH: 12
<212> TYPE: PRT
<213> ORGANISM: Artificial Sequence
<220> FEATURE:
<223> OTHER INFORMATION: Description of Artificial Sequence: SV40
      nuclear localization signal

<400> SEQUENCE: 68

```
Thr Pro Pro Lys Lys Arg Lys Val Glu Asp Ala Ser
 1               5                  10
```

<210> SEQ ID NO 69
<211> LENGTH: 35
<212> TYPE: DNA
<213> ORGANISM: Artificial Sequence
<220> FEATURE:
<223> OTHER INFORMATION: Description of Artificial Sequence:
      Oligonucleotide primer

<400> SEQUENCE: 69

```
catccatggc tagattagat aaaagtaaag taaag                              35
```

<210> SEQ ID NO 70
<211> LENGTH: 4
<212> TYPE: PRT
<213> ORGANISM: Artificial Sequence
<220> FEATURE:
<223> OTHER INFORMATION: Description of Artificial Sequence: Amino Acids
      of EMCV polypeptide

<400> SEQUENCE: 70

```
Met Ala Thr Thr
 1
```

<210> SEQ ID NO 71
<211> LENGTH: 34
<212> TYPE: DNA
<213> ORGANISM: Artificial Sequence
<220> FEATURE:
<223> OTHER INFORMATION: Description of Artificial Sequence:
      Oligonucleotide primer

<400> SEQUENCE: 71

```
gctctagact agtgattttt ttctccattt tagc                               34
```

<210> SEQ ID NO 72
<211> LENGTH: 25
<212> TYPE: DNA
<213> ORGANISM: Artificial Sequence
<220> FEATURE:
<223> OTHER INFORMATION: Description of Artificial Sequence:
      Oligonucleotide primer -continued

```
<400> SEQUENCE: 72
ccacaggtac acctccaatt gactc                                              25

<210> SEQ ID NO 73
<211> LENGTH: 26
<212> TYPE: DNA
<213> ORGANISM: Artificial Sequence
<220> FEATURE:
<223> OTHER INFORMATION: Description of Artificial Sequence:
      Oligonucleotide primer

<400> SEQUENCE: 73
gtggtgatcc taactgacct taagac                                             26

<210> SEQ ID NO 74
<211> LENGTH: 24
<212> TYPE: DNA
<213> ORGANISM: Artificial Sequence
<220> FEATURE:
<223> OTHER INFORMATION: Description of Artificial Sequence:
      Oligonucleotide primer

<400> SEQUENCE: 74
gtgtcatgca caaagtagat gtcc                                               24

<210> SEQ ID NO 75
<211> LENGTH: 25
<212> TYPE: DNA
<213> ORGANISM: Artificial Sequence
<220> FEATURE:
<223> OTHER INFORMATION: Description of Artificial Sequence:
      Oligonucleotide primer

<400> SEQUENCE: 75
ctcggattaa atgtcaggaa ttgtg                                              25
```